US011667978B2

(12) United States Patent
Bres et al.

(10) Patent No.: US 11,667,978 B2
(45) Date of Patent: Jun. 6, 2023

(54) **DETECTING *BABESIA* SPECIES NUCLEIC ACID IN A SAMPLE**

(71) Applicant: Gen-Probe Incorporated, San Diego, CA (US)

(72) Inventors: Vanessa Bres, San Diego, CA (US); Deanna Self, Escondido, CA (US); Jeffrey M. Linnen, Poway, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 16/611,806

(22) PCT Filed: Jun. 6, 2018

(86) PCT No.: PCT/US2018/036214
§ 371 (c)(1),
(2) Date: Nov. 7, 2019

(87) PCT Pub. No.: WO2018/226798
PCT Pub. Date: Dec. 13, 2018

(65) Prior Publication Data

US 2021/0079485 A1 Mar. 18, 2021

Related U.S. Application Data

(60) Provisional application No. 62/520,793, filed on Jun. 16, 2017, provisional application No. 62/516,530, filed on Jun. 7, 2017.

(51) Int. Cl.

| | |
|---|---|
| ***C07H 21/04*** | (2006.01) |
| ***C12Q 1/68*** | (2018.01) |
| ***C12Q 1/6893*** | (2018.01) |
| ***C12Q 1/6806*** | (2018.01) |

(52) U.S. Cl.
CPC ......... *C12Q 1/6893* (2013.01); *C12Q 1/6806* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | | | |
|---|---|---|---|---|
| 2013/0157874 A1 | 6/2013 | Dowd | | |
| 2016/0201144 A1* | 7/2016 | Chelliserry | .......... | C12Q 1/6806 435/6.11 |

FOREIGN PATENT DOCUMENTS

| | | | | |
|---|---|---|---|---|
| CN | 102181556 A | 9/2011 | | |
| CN | 102230008 A | 11/2011 | | |
| CN | 103103286 A | 5/2013 | | |
| WO | 1999/60009 A1 | 11/1999 | | |
| WO | 2014/071946 A1 | 5/2014 | | |
| WO | 2014/197607 A1 | 12/2014 | | |
| WO | 2016/064887 A1 | 4/2016 | | |
| WO | 2016/183282 A1 | 11/2016 | | |
| WO | WO-2016183282 A1 * | 11/2016 | ............... | C12Q 1/70 |

OTHER PUBLICATIONS

Bloch et al., Development of a real-time polymerase chain reaction assay for sensitive detection and quantitation of Babesia microti infection. Transfusion; 2013; 53:2299-2306. (Year: 2013).*

Eshoo et al. Vector-Borne and Zoonotic Diseases; 2014; 14: 584-591. (Year: 2014).*

Blaschitz et al. Applied and Environmental Microbiology; 2008: 4841-4846. (Year: 2008).*

Bloch et al., "Development of a real-time polymerase chain reaction assay for sensitive detection and quantitation of Babesia microti infection." Transfusion, 2013, vol. 53, Issue 10.

(Continued)

*Primary Examiner* — Jeanine A Goldberg
(74) *Attorney, Agent, or Firm* — Nicholas V. Sherbina; Jeffrey E. Landes

(57) ABSTRACT

There is described herein a method for specifically detecting *Babesia* species nucleic acid in a sample, which in one aspect comprises: (1) contacting a sample, said sample suspected of containing *Babesia* species nucleic acid, with at least two oligomers for amplifying a target region of a *Babesia* species target nucleic acid, wherein the at least two amplification oligomers comprise: (a) a first amplification oligomer comprising a first target-hybridizing sequence (i) that is from about 15 to about 33 contiguous nucleotides in length, is contained in the sequence of SEQ ID NO:66 and comprises SEQ ID NO:56 or 57; or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises or consists of SEQ ID NO:8; (v) comprises or consists of SEQ ID NO:83 and (b) a second amplification oligomer comprising a second target-hybridizing sequence that is from about 15 to about 33 contiguous nucleotides in length, and (i) is contained in SEQ ID NO:68 and comprises SEQ ID NO:52, SEQ ID NO:53, SEQ ID NO:54, SEQ ID NO:55, or SEQ ID NO:85; or (ii) is contained in SEQ ID NO:67 and comprises SEQ ID NO:45 or SEQ ID NO:52; or (iii) is contained in SEQ ID NO:70 and comprises SEQ ID NO:46, SEQ ID NO:47, SEQ ID NO:48, SEQ ID NO:49, SEQ ID NO:50, or SEQ ID NO:51; (2) performing an in vitro nucleic acid amplification reaction, wherein any *Babesia* target nucleic acid present in said sample is used as a template for generating an amplification product; and (3) detecting the presence or absence of the amplification product, thereby indicating the presence or absence of *Babesia* species target nucleic acid in said sample.

14 Claims, No Drawings

Specification includes a Sequence Listing.

(56) References Cited

OTHER PUBLICATIONS

Cornillot et al., "Sequencing of the smallest Apicomplexan genome from the human pathogen Babesia microti." Nucleic Acids Research, 2012, vol. 40, No. 18.

Teal et al., "A new real-time PCR assay for improved detection of the parasite Babesia microti." Journal of Clinical Microbiology, 2012, vol. 50, No. 3, pp. 903-908.

Tonnetti et al., "Transfusion-transmitted Babesia microti identified through hemovigilance." Transfusion, 2009 vol. 49, pp. 2557-2563.

International Search Report and Written Opinion dated Aug. 9, 2018 in corresponding PCT Application No. PCT/US2018/036214 (31 pages).

Examination Report dated Dec. 21, 2020 in corresponding European Application No. 18734394.2 (6 pages).

Examination Report dated Apr. 20, 2021 in corresponding Australian Application No. 2018281196 (5 pages).

Criado-Fornelio, "A review of nucleic acid-based diagnostic tests for Babesia and Theileria, with emphasis on bovine piroplasms," Parasitologia 49 (Suppl. 1):39-44, 2007.

* cited by examiner

DETECTING *BABESIA* SPECIES NUCLEIC ACID IN A SAMPLE

CROSS-REFERENCE TO RELATED APPLICATIONS

This application is a national stage entry of International Application No. PCT/US2018/036214, filed Jun. 6, 2018, which claims the benefit under 35 U.S.C. § 119(e) of U.S. Provisional Application Nos. 62/516,530, filed Jun. 7, 2017, and 62/520,793, filed Jun. 16, 2017. The entire contents of each of the foregoing applications are incorporated herein by reference in their entirety.

REFERENCE TO SEQUENCE LISTING

The instant application contains a Sequence Listing which has been submitted in ASCII format via EFS-Web and is hereby incorporated by reference in its entirety. Said ASCII Copy, created on Mar. 1, 2022, is named "DIA-0033-04_ST25.txt" and is 43,884 bytes in size.

BACKGROUND

Babesiosis is caused by infection of red blood cells by species of protozoan parasites of the genus *Babesia*. The species *Babesia microti* is responsible for most human babesiosis infections reported in the United States. Infections are typically asymptomatic in human individuals but can lead to severe illness or death, especially in elderly or immunosuppressed individuals. The parasite is transmitted to humans by exposure to deer ticks in endemic areas or by blood transfusion (transfusion-transmitted babesiosis (TTB)). Over 100 cases of transfusion-transmitted babesiosis have been reported to the FDA since 1979. Despite being reported as the most unaddressed infectious risk to the United States blood supply, there is still no licensed test for screening for *B. microti* in donated blood (*N Engl J Med.* (2016) 8, 375(23):2236-2245). The threat of TTB has led to a consensus by the Food and Drug Administration (FDA) and the American Association of Blood Banks (AABB) that screening of blood donations for *Babesia* is urgently required for blood safety. Initiation of blood donor screening to prevent TTB should be given high priority (*Curr Opin Hematol.* (2016) 23(6):573-580).

Therefore a specific and sensitive assay for detecting *Babesia* species in a sample is needed.

SUMMARY

In one aspect, there is provided a method for specifically detecting *Babesia* species nucleic acid in a sample, said method comprising: (1) contacting a sample, said sample suspected of containing *Babesia* species nucleic acid, with at least two oligomers for amplifying a target region of a *Babesia* species target nucleic acid, wherein the at least two amplification oligomers comprise: (a) a first amplification oligomer comprising a first target-hybridizing sequence (i) that is from about 15 to about 33 contiguous nucleotides in length, is contained in the sequence of SEQ ID NO:66 and comprises SEQ ID NO:56 or 57; or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises or consists of SEQ ID NO:8; (v) comprises or consists of SEQ ID NO:83 and (b) a second amplification oligomer comprising a second target-hybridizing sequence that is from about 15 to about 33 contiguous nucleotides in length, and (i) is contained in SEQ ID NO:68 and comprises SEQ ID NO:52, SEQ ID NO:53, SEQ ID NO:54, SEQ ID NO:55, or SEQ ID NO:85; or (ii) is contained in SEQ ID NO:67 and comprises SEQ ID NO:45 or SEQ ID NO:52; (iii) is contained in SEQ ID NO:70 and comprises SEQ ID NO:46, SEQ ID NO:47, SEQ ID NO:48, SEQ ID NO:49, SEQ ID NO:50, or SEQ ID NO:51, or (iv) comprises or consists of SEQ ID NO:84; (2) performing an in vitro nucleic acid amplification reaction, wherein any *Babesia* target nucleic acid present in said sample is used as a template for generating an amplification product; and (3) detecting the presence or absence of the amplification product, thereby indicating the presence or absence of *Babesia* species target nucleic acid in said sample.

Suitably, the first target-hybridizing sequence comprises or consists of a sequence selected from the group consisting of: SEQ ID NOs:2, and 4 and 6 and 8, suitably, wherein the first target-hybridizing sequence comprises or consists of a sequence selected from the group consisting of: SEQ ID NOs:2, and 4 and 8.

Suitably, the second amplification oligomer comprises or consists of the sequence selected from the group consisting of: SEQ ID NOs:13, 16, 17, 18, 19, 20, 21, 27, 28, 29, 31, 32, 33, 34, 35, 36, 84 and 86.

Suitably, the second amplification oligomer sequence comprises or consists of SEQ ID NO:21 or SEQ ID NO:27 or SEQ ID NO:34 or SEQ ID NO:84 or SEQ ID NO:86.

Suitably, the first amplification oligomer is a promoter primer or promoter provider further comprising a promoter sequence located 5' to the first target-hybridizing sequence. Suitably, the promoter sequence is a T7 promoter sequence. Suitably, the T7 promoter sequence comprises or consists of SEQ ID NO:58.

Suitably, the first amplification oligomer comprises or consists of a sequence selected from the group consisting of SEQ ID NOs:1 and 3 and 5 and 7 and 82, suitably, wherein the first amplification oligomer comprises or consists of a sequence selected from the group consisting of SEQ ID NOs:1 and 3 and 7 and 82.

Suitably, the first and second target-hybridizing sequences respectively comprise or consist of the nucleotide sequences of: (a) SEQ ID NO:SEQ ID NO:2 or 6 and SEQ ID NO:11; (b) SEQ ID NO:4 or 6 and SEQ ID NO:13; (c) SEQ ID NO:4 and SEQ ID NO:16 or SEQ ID NO:17; (d) SEQ ID NO:4 and SEQ ID NO:18 or SEQ ID NO:19; (e) SEQ ID NO:4 and SEQ ID NO:20; (f) SEQ ID NO:4 or 6 or 8 and SEQ ID NO:21; (g) SEQ ID NO:2 or 4 or 8 and SEQ ID NO:27; (h) SEQ ID NO:4 and SEQ ID NO:28; (i) SEQ ID NO:4 and SEQ ID NO:29; (j) SEQ ID NO:4 and SEQ ID NO:31; (k) SEQ ID NO:8 and SEQ ID NO:32; (1) SEQ ID NO:8 and SEQ ID NO:33; (m) SEQ ID NO:8 and SEQ ID NO:34; (n) SEQ ID NO:8 and SEQ ID NO:35; (o) SEQ ID NO:8 and SEQ ID NO:36; (p) SEQ ID NO:8 and SEQ ID NO:84; (q) SEQ ID NO:8 and SEQ ID NO:86; (r) SEQ ID NO:83 and SEQ ID NO:34; (s) SEQ ID NO:83 and SEQ ID NO:35; (t) SEQ ID NO:83 and SEQ ID NO:36; (u) SEQ ID NO:83 and SEQ ID NO:84; (v) SEQ ID NO:83 and SEQ ID NO:86.

Suitably, the first and second target-hybridizing sequences respectively comprise or consist of the nucleotide sequences of: (a) SEQ ID NO:2 and SEQ ID NO:27; (b) SEQ ID NO:4 and SEQ ID NO:21; (c) SEQ ID NO:8 and SEQ ID NO:21; (d) SEQ ID NO:8 and SEQ ID NO:34; (e) SEQ ID NO:8 and SEQ ID NO:84; (f) SEQ ID NO:8 and SEQ ID NO:86; (g)

SEQ ID NO:83 and SEQ ID NO:34; (h) SEQ ID NO:83 and SEQ ID NO:84; (i) SEQ ID NO:83 and SEQ ID NO:86.

Suitably, the method further comprises purifying the target nucleic acid from other components in the sample before step (1).

Suitably, the purifying step comprises contacting the sample with at least one capture probe oligomer comprising a target-hybridizing sequence covalently attached to a sequence or moiety that binds to an immobilized probe, wherein said target-hybridizing sequence (i) is from about 15 to 21 contiguous nucleotides contained in the sequence of SEQ ID NO:78; or (ii) is from about 21 to 30 contiguous nucleotides comprising the sequence of SEQ ID NO:78; or (iii) is the sequence is SEQ ID NO:44. Suitably, the capture probe oligomer sequence comprises or consists of SEQ ID NO:43.

Suitably, the detecting step (3) comprises contacting said in vitro nucleic acid amplification reaction with a detection probe oligomer configured to specifically hybridize to the amplification product under conditions whereby the presence or absence of the amplification product is determined, thereby indicating the presence or absence of *Babesia* species in said sample.

Suitably, the detection probe oligomer comprises a target-hybridizing sequence that is from about 14 to about 40 nucleotides in length and is configured to specifically hybridize to a target sequence comprising or consisting of SEQ ID NO:59, the RNA equivalent of SEQ ID NO:59, the complement of SEQ ID NO:59, the RNA equivalent of the complement of SEQ ID NO:59, or SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence is contained in the sequence of SEQ ID NO:65 and includes at least the sequence of SEQ ID NO:37 or SEQ ID NO:42.

Suitably, the detection probe target-hybridizing sequence is contained in the sequence of SEQ ID NO:41 and includes at least the sequence of SEQ ID NO:38 or SEQ ID NO:39.

Suitably, the detection probe consists of the sequence selected from the group consisting of: SEQ ID NO:37, 38, 39, 41, 42, 91, 92, 94, or 99.

Suitably, the detection probe comprises or consists of a nucleotide sequence selected from the group consisting of SEQ ID NOs:37, 38, 39, 40, 41, 42, 59, 60, 91, 92, 93, 94, 98 and 99.

Suitably, the detection probe oligomer further comprises a 2' methoxy modification on at least one nucleotide residue member of the nucleotide sequence.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:11 and SEQ ID NO:39 or SEQ ID NO:37; (b) SEQ ID NO:2 and SEQ ID NO:27 and SEQ ID NO:38 or SEQ ID NO:39; (c) SEQ ID NO:4 and SEQ ID NO:13 and SEQ ID NO:39 or SEQ ID NO:37; (d) SEQ ID NO:4 and SEQ ID NO:16 or SEQ ID NO:17 and SEQ ID NO:39; (e) SEQ ID NO:4 and SEQ ID NO:18 or SEQ ID NO:19 and SEQ ID NO:39 or SEQ ID NO:37; (f) SEQ ID NO:4 and SEQ ID NO:20 and SEQ ID NO:39 or SEQ ID NO:37; (g) SEQ ID NO:4 and SEQ ID NO:21 and SEQ ID NO:39 or SEQ ID NO:37; (h) SEQ ID NO:4 and SEQ ID NO:27 and SEQ ID NO:39 or SEQ ID NO:38; (i) SEQ ID NO:4 and SEQ ID NO:28 and SEQ ID NO:39; (j) SEQ ID NO:4 and SEQ ID NO:29 and SEQ ID NO:39 or SEQ ID NO:37; (k) SEQ ID NO:4 and SEQ ID NO:31 and SEQ ID NO:39; (1) SEQ ID NO:6 and SEQ ID NO:11 and SEQ ID NO:37; (m) SEQ ID NO:6 and SEQ ID NO:13 and SEQ ID NO:37; (n) SEQ ID NO:6 and SEQ ID NO:21 and SEQ ID NO:37; (o) SEQ ID NO:8 and SEQ ID NO:21 and SEQ ID NO:39 or SEQ ID NO:37 or SEQ ID NO:42; (p) SEQ ID NO:8 and SEQ ID NO:27 and SEQ ID NO:39; (q) SEQ ID NO:8 and SEQ ID NO:32 and SEQ ID NO:37 or SEQ ID NO:42; (r) SEQ ID NO:8 and SEQ ID NO:33 and SEQ ID NO:37 or SEQ ID NO:42; (s) SEQ ID NO:8 and SEQ ID NO:34 and SEQ ID NO:37 or SEQ ID NO:42; (t) SEQ ID NO:8 and SEQ ID NO:35 and SEQ ID NO:37 or SEQ ID NO:42; (u) SEQ ID NO:8 and SEQ ID NO:36 and SEQ ID NO:37 or SEQ ID NO:42; (v) SEQ ID NO:8, and SEQ ID NO:34, 84, or 86, and SEQ ID NO:91, 92, or 93; (v) SEQ ID NO:8, and SEQ ID NO:34, 84, or 86, and SEQ ID NO:37, 38, 39, 40, 41, 42, 59, 60, 91, 92, 93, 94, 98 or 99; or (x) SEQ ID NO:83, and SEQ ID NO:34, 84, or, 86, and SEQ ID NO:91, 92, or 93.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:27 and SEQ ID NO:38; (b) SEQ ID NO:4 and SEQ ID NO:21 and SEQ ID NO:39; (c) SEQ ID NO:8 and SEQ ID NO:21 and SEQ ID NO:37 or SEQ ID NO:39; (d) SEQ ID NO:8 and SEQ ID NO:34 and SEQ ID NO:37, 42, 91, 92 or 93; (e) SEQ ID NO:8 and SEQ ID NO:34, or 84 or 86 and SEQ ID NO:37, 42, 91, 92 or 93; (f) SEQ ID NO:83 and SEQ ID NO:34, 84 or 86 and SEQ ID NO:37, 42, 91, 92 or 93; (g) SEQ ID NO:8 and SEQ ID NO:34, 84 or 86 and SEQ ID NO:37, 42, 91, 92 or 93; (h) SEQ ID NO:83 and SEQ ID NO:34, 84 or 86 and SEQ ID NO:37, 38, 39, 40, 41, 42, 59, 60, 91, 92, 93, 94, 98 or 99; or (i) SEQ ID NO:83 and SEQ ID NO:34, 84 or 86 and SEQ ID NO:37, 42, 91, 92 or 93.

Suitably, the detection probe comprises a label. Suitably, the label is a chemiluminescent label or a fluorescent label. Suitably, the detecting step (3) occurs during the amplifying step (2). Suitably, the detection probe comprises a fluorescent label and a quencher. Suitably, the detection probe is selected from the group consisting of a molecular torch, a molecular beacon, and a TaqMan detection probe. Suitably, the detection probe further comprises a non-target-hybridizing sequence. Suitably, the detection probe is a molecular torch or a molecular beacon.

Suitably, the amplification reaction at step (2) is an isothermal amplification reaction. Suitably, the amplification reaction is a transcription-mediated amplification (TMA) reaction. Suitably, the amplification reaction is a real-time amplification reaction.

Suitably, the sample is a clinical sample. Suitably, the sample is a blood sample. Suitably, the sample is a lysed blood cell sample. Suitably, the lysed blood cell sample is a lysed red blood cell sample.

Suitably, the amplification product has a length of from 180 to 220 contiguous nucleotides and contains SEQ ID NO:65 or the complement thereof.

In a further aspect, there is described a method for specifically detecting *Babesia* species nucleic acid in a sample, said method comprising: (1) contacting a sample, said sample suspected of containing *Babesia* species nucleic acid, with at least two oligomers for amplifying a target region of a *Babesia* species target nucleic acid, wherein two of said at least two amplification oligomers are selected from the group consisting of: (a) a first amplification oligomer and a second amplification oligomer, wherein the first amplification oligomer comprises a first target-hybridizing sequence (i) that is from 15 to 33 contiguous nucleobases in length, is contained in SEQ ID NO:66 and contains SEQ ID NO:56 or SEQ ID NO:57, or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises/consists of SEQ ID NO:8; (v) comprises or consists of SEQ ID NO:83; or (b) a first amplification oligomer and a second amplification oligomer, wherein the second amplification oligomer comprises a second target-hybridizing sequence that is from about 15 to about 33 contiguous nucleotides in length, and (i) is contained in SEQ ID NO:68 and contains SEQ ID NO:52, SEQ ID NO:53 SEQ ID NO:54, SEQ ID NO:55, or SEQ ID NO:85, or (ii) is contained in SEQ ID NO:67 and contains SEQ ID NO:45 or SEQ ID NO:69, or (iii) is contained in SEQ ID NO:70 and contains SEQ ID NO:46, SEQ ID NO:47, SEQ ID NO:48, SEQ ID NO:49, SEQ ID NO:50, or SEQ ID NO:51, or (iv) comprises or consists of SEQ ID NO:84; (2) performing an in vitro nucleic acid amplification reaction, wherein any *Babesia* target nucleic acid present in said sample is used as a template for generating an amplification product, wherein said amplification product has a length of from 180 to 220 contiguous nucleotides and contains SEQ ID NO:65 or the complement thereof; and (3) detecting the presence or absence of the amplification product, thereby indicating the presence or absence of *Babesia* species target nucleic acid in said sample.

Suitably, the first target-hybridizing sequence comprises or consists of a sequence selected from the group consisting of: SEQ ID NOs:2, and 4 and 6 and 8, suitably, wherein the first target-hybridizing sequence comprises or consists of a sequence selected from the group consisting of: SEQ ID NOs:2, and 4 and 8.

Suitably, the second amplification oligomer comprises or consists of the sequence selected from the group consisting of: SEQ ID NOs:13, 16, 17, 18, 19, 20, 21, 27, 28, 29, 31, 32, 33, 34, 35, 36, 84, and 86.

Suitably, the second amplification oligomer sequence comprises or consists of SEQ ID NO:21 or SEQ ID NO:27 or SEQ ID NO:34 or SEQ ID NO:84 or SEQ ID NO:86.

Suitably, the first amplification oligomer is a promoter primer or promoter provider further comprising a promoter sequence located 5' to the first target-hybridizing sequence. Suitably, the promoter sequence is a T7 promoter sequence. Suitably, the T7 promoter sequence comprises or consists of SEQ ID NO:58. Suitably, the first amplification oligomer comprises or consists of a sequence selected from the group consisting of SEQ ID NOs:1 and 3 and 5 and 7 and 82, suitably, wherein the first amplification oligomer comprises or consists of a sequence selected from the group consisting of SEQ ID NOs:1 and 3 and 7 and 82.

Suitably, the first and second target-hybridizing sequences respectively comprise or consist of the nucleotide sequences of: (a) SEQ ID NO:2 or 6 and SEQ ID NO:11; (b) SEQ ID NO:4 or 6 and SEQ ID NO:13; (c) SEQ ID NO:4 and SEQ ID NO:16 or SEQ ID NO:17; (d) SEQ ID NO:4 and SEQ ID NO:18 or SEQ ID NO:19; (e) SEQ ID NO:4 and SEQ ID NO:20; (1) SEQ ID NO:4 or 6 or 8 and SEQ ID NO:21; (g) SEQ ID NO:2 or 4 or 8 and SEQ ID NO:27; (h) SEQ ID NO:4 and SEQ ID NO:28; (i) SEQ ID NO:4 and SEQ ID NO:29; (j) SEQ ID NO:4 and SEQ ID NO:31; (k) SEQ ID NO:8 and SEQ ID NO:32; (1) SEQ ID NO:8 and SEQ ID NO:33; (m) SEQ ID NO:8 and SEQ ID NO:34; (n) SEQ ID NO:8 and SEQ ID NO:35; (o) SEQ ID NO:8 and SEQ ID NO:36; (p) SEQ ID NO:8 and SEQ ID NO:84; (q) SEQ ID NO:8 and SEQ ID NO:86; (r) SEQ ID NO:83 and SEQ ID NO:34; (s) SEQ ID NO:83 and SEQ ID NO:84; (t) SEQ ID NOs:83 and SEQ ID NO:86.

Suitably, the first and second target-hybridizing sequences respectively comprise or consist of the nucleotide sequences of: (a) SEQ ID NO:2 and SEQ ID NO:27; (b) SEQ ID NO:4 and SEQ ID NO:21; (c) SEQ ID NO:8 and SEQ ID NO:21; (d) SEQ ID NO:8 and SEQ ID NO:34; (e) SEQ ID NO:8 and SEQ ID NO:84; (f) SEQ ID NO:8 and SEQ ID NO:86; (g) SEQ ID NO:83 and SEQ ID NO:34; (h) SEQ ID NO:83 and SEQ ID NO:84; (i) SEQ ID NO:83 and SEQ ID NO:86.

Suitably, the method further comprises purifying the target nucleic acid from other components in the sample before step (1).

Suitably, the purifying step comprises contacting the sample with at least one capture probe oligomer comprising a target-hybridizing sequence covalently attached to a sequence or moiety that binds to an immobilized probe, wherein said target-hybridizing sequence (i) is from about 15 to 21 contiguous nucleotides contained in the sequence of SEQ ID NO:78; or (ii) is from about 21 to about 30 contiguous nucleotides comprising the sequence of SEQ ID NO:78; or (iii) the sequence consists of SEQ ID NO:44.

Suitably, the capture probe oligomer sequence comprises or consists of SEQ ID NO:43.

Suitably, the detecting step (3) comprises contacting said in vitro nucleic acid amplification reaction with a detection probe oligomer configured to specifically hybridize to the amplification product under conditions whereby the presence or absence of the amplification product is determined, thereby indicating the presence or absence of *Babesia* species in said sample.

Suitably, the detection probe oligomer comprises a target-hybridizing sequence that is from about 14 to about 40 nucleotides in length and is configured to specifically hybridize to a target sequence comprising or consisting of SEQ ID NO:59, the RNA equivalent of SEQ ID NO:59, the complement of SEQ ID NO:59, the RNA equivalent of the complement of SEQ ID NO:59, SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence is contained in the sequence of SEQ ID NO:59 and includes at least the sequence of SEQ ID NO:42, 92, 94, or 99.

Suitably, the detection probe target-hybridizing sequence is contained in the sequence of SEQ ID NO:41 and includes at least the sequence of SEQ ID NO:38 or SEQ ID NO:60.

Suitably, the detection probe oligomer comprises a nucleotide sequence that is from 16 to 25 contiguous nucleotides in length and specifically hybridizes to SEQ ID NO:65, or the DNA equivalent thereof; or specifically hybridizes to the complement of SEQ ID NO:65, or the DNA equivalent thereof.

Suitably, the detection probe oligomer sequence further comprises a nucleotide sequence containing SEQ ID NO:59 or SEQ ID NO:60.

Suitably, the detection probe oligomer further comprises a nucleotide sequence consisting of SEQ ID NO:37, 38, 39, 42, or 99.

Suitably, the detection probe target-hybridizing sequence consists of the sequence selected from the group consisting of: SEQ ID NOs:37, 38, 39, 40, 41, 42, 59, 60, 91, 92, 93, 94, 98 and 99.

Suitably, the detection probe oligomer further comprises a 2' methoxy modification on at least one nucleotide residue member of the nucleotide sequence.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:11 and SEQ ID NO:39 or SEQ ID NO:37; (b) SEQ ID NO:2 and SEQ ID NO:27 and SEQ ID NO:38 or SEQ ID NO:39; (c) SEQ ID NO:4 and SEQ ID NO:13 and SEQ ID NO:39 or SEQ ID NO:37; (d) SEQ ID NO:4 and SEQ ID NO:16 or SEQ ID NO:17 and SEQ ID NO:39; (e) SEQ ID NO:4 and SEQ ID NO:18 or SEQ ID NO:19 and SEQ ID NO:39 or SEQ ID NO:37; (f) SEQ ID NO:4 and SEQ ID NO:20 and SEQ ID NO:39 or SEQ ID NO:37; (g) SEQ ID NO:4 and SEQ ID NO:21 and SEQ ID NO:39 or SEQ ID NO:37; (h) SEQ ID NO:4 and SEQ ID NO:27 and SEQ ID NO:39 or SEQ ID NO:38; (i) SEQ ID NO:4 and SEQ ID NO:28 and SEQ ID NO:39; (j) SEQ ID NO:4 and SEQ ID NO:29 and SEQ ID NO:39 or SEQ ID NO:37; (k) SEQ ID NO:4 and SEQ ID NO:31 and SEQ ID NO:39; (1) SEQ ID NO:6 and SEQ ID NO:11 and SEQ ID NO:37; (m) SEQ ID NO:6 and SEQ ID NO:13 and SEQ ID NO:37; (n) SEQ ID NO:6 and SEQ ID NO:21 and SEQ ID NO:37; (o) SEQ ID NO:8 and SEQ ID NO:21 and SEQ ID NO:39 or SEQ ID NO:37 or SEQ ID NO:42; (p) SEQ ID NO:8 and SEQ ID NO:27 and SEQ ID NO:39; (q) SEQ ID NO:8 and SEQ ID NO:32 and SEQ ID NO:37 or SEQ ID NO:42; (r) SEQ ID NO:8 and SEQ ID NO:33 and SEQ ID NO:37 or SEQ ID NO:42; (s) SEQ ID NO:8 and SEQ ID NO:34 and SEQ ID NO:37 or SEQ ID NO:42; (t) SEQ ID NO:8 and SEQ ID NO:35 and SEQ ID NO:37 or SEQ ID NO:42; or (u) SEQ ID NO:8 and SEQ ID NO:36 and SEQ ID NO:37 or SEQ ID NO:42; (v) SEQ ID NO:8, and SEQ ID NO:84, and SEQ ID NOs:91, 92 and/or 93; (w) SEQ ID NO:8, and SEQ ID NO:86, and SEQ ID NOs:91, 92 and/or 93; (x) SEQ ID NO:83, and SEQ ID NO:34, and SEQ ID NOs:91, 92 and/or 93; (y) SEQ ID NOs:83, and SEQ ID NO:84, and SEQ ID NOs:91, 92 and/or 93; (z) SEQ ID NOs:83, and SEQ ID NO:86, and SEQ ID NOs:91, 92 and/or 93; or (aa) SEQ ID NO:8 or 83, SEQ ID NO:34, 84 or 86, and SEQ ID NO:37, 38, 39, 40, 41, 42, 59, 60, 91, 92, 93, 94, 98 or 99.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:27 and SEQ ID NO:38; (b)SEQ ID NO:4 and SEQ ID NO:21 and SEQ ID NO:39; (c)SEQ ID NO:8 and SEQ ID NO:21 and SEQ ID NO:37 or SEQ ID NO:39; or (d) SEQ ID NO:8 and SEQ ID NO:34 and SEQ ID NO:37 or SEQ ID NO:42; (e) SEQ ID NO:8, and SEQ ID NO:84, and SEQ ID NOs:91, 92 and/or 93; (f) SEQ ID NO:8, and SEQ ID NO:86, and SEQ ID NOs:91, 92 and/or 93; (g) SEQ ID NO:83, and SEQ ID NO:34, and SEQ ID NOs:91, 92 and/or 93; (h) SEQ ID NOs:83, and SEQ ID NO:84, and SEQ ID NOs:91, 92 and/or 93; (i) SEQ ID NOs:83, and SEQ ID NO:86, and SEQ ID NOs:91, 92 and/or 93; or (j) SEQ ID NO:8 or 83, SEQ ID NO:34, 84 or 86, and SEQ ID NO:37, 38, 39, 40, 41, 42, 59, 60, 91, 92, 93, 94, 98 or 99.

Suitably, the detection probe comprises a label. Suitably, the label is a chemiluminescent label or a fluorescent label. Suitably, the detecting step (3) occurs during the amplifying step (2). Suitably, the detection probe comprises a fluorescent label and a quencher. Suitably, the detection probe is selected from the group consisting of a molecular torch, a molecular beacon, and a TaqMan detection probe. Suitably, the detection probe further comprises a non-target-hybridizing sequence. Suitably, the detection probe is a molecular torch or a molecular beacon.

Suitably, the amplification reaction at step (2) is an isothermal amplification reaction. Suitably, the amplification reaction is a transcription-mediated amplification (TMA) reaction. Suitably, the amplification reaction is a real-time amplification reaction.

Suitably, the sample is a clinical sample. Suitably, the sample is a blood sample. Suitably, the sample is a lysed blood cell sample.

Suitably, the lysed blood cell sample is a lysed red blood cell sample.

In a further aspect, there is described a combination of at least two oligomers for determining the presence or absence of *Babesia* in a sample, said oligomer combination comprising first and second amplification oligomers for amplifying a target region of *Babesia* target nucleic acid, wherein (a) the first amplification oligomer comprises a first target-hybridizing sequence (i) that is from about 15 to about 33 contiguous nucleotides in length, is contained in the sequence of SEQ ID NO:66 and comprises SEQ ID NO:56 or 57; or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises or consists of SEQ ID NO:8; (v) comprises or consists of SEQ ID NO:83 and (b) the second amplification oligomer comprises a second target-hybridizing sequence that is from about 15 to about 33 contiguous nucleotides in length, and (i) is contained in SEQ ID NO:68 and comprises SEQ ID NO:52, SEQ ID NO:53, SEQ ID NO:54, SEQ ID NO:55, or SEQ ID NO:85; or (ii) is contained in SEQ ID NO:67 and comprises SEQ ID NO:45 or SEQ ID NO:52; or (iii) is contained in SEQ ID NO:70 and comprises SEQ ID NO:46, SEQ ID NO:47, SEQ ID NO:48, SEQ ID NO:49, SEQ ID NO:50, or SEQ ID NO:51; or (iv) comprises or consists of SEQ ID NO:84.

Suitably, the first amplification comprises or consists of the sequence selected from the group consisting of: SEQ ID NOs:2 and 4 and 6 and 8 and 83, suitably, wherein the first amplification comprises or consists of the sequence selected from the group consisting of: SEQ ID NOs:2 and 4 and 8 and 83.

Suitably, the second amplification oligomer comprises or consists of the sequence selected from the group consisting of: SEQ ID NOs:13, 16, 17, 18, 19, 20, 21, 27, 28, 29, 31, 32, 33, 34, 35, 36, 84, and 86.

Suitably, the second amplification oligomer sequence comprises or consists of SEQ ID NO:21 or SEQ ID NO:27 or SEQ ID NO:34 or SEQ ID NO:84 or SEQ ID NO:86.

Suitably, the first amplification oligomer is a promoter primer or promoter provider further comprising a promoter sequence located 5' to the first target-hybridizing sequence. Suitably, the promoter sequence is a T7 promoter sequence. Suitably, the T7 promoter sequence comprises or consists of SEQ ID NO:58.

Suitably, the first amplification oligomer comprises or consists of a sequence selected from the group consisting of SEQ ID NOs:1 and 3 and 5 and 7 and 82, suitably, wherein the first amplification oligomer comprises or consists of a sequence selected from the group consisting of SEQ ID NOs:1 and 3 and 7 and 82.

Suitably, the first and second target-hybridizing sequences respectively comprise or consist of the nucleotide sequences of: (a) SEQ ID NO:2 or 6 and SEQ ID NO:11; (b) SEQ ID NO:4 or 6 and SEQ ID NO:13; (c) SEQ ID NO:4 and SEQ ID NO:16 or SEQ ID NO:17; (d) SEQ ID NO:4 and SEQ ID NO:18 or SEQ ID NO:19; (e) SEQ ID NO:4 and SEQ ID NO:20; (1) SEQ ID NO:4 or 6 or 8 and SEQ ID NO:21; (g) SEQ ID NO:2 or 4 or 8 and SEQ ID NO:27; (h) SEQ ID NO:4 and SEQ ID NO:28; (i) SEQ ID NO:4 and SEQ ID NO:29; (j) SEQ ID NO:4 and SEQ ID NO:31; (k) SEQ ID NO:8 and SEQ ID NO:32; (1)SEQ ID NO:8 and SEQ ID NO:33; (m) SEQ ID NO:8 and SEQ ID NO:34; (n) SEQ ID NO:8 and SEQ ID NO:35; (o) SEQ ID NO:8 and SEQ ID NO:36; (p) SEQ ID NO:8 and SEQ ID NO:84; (q) SEQ ID NO:8 and SEQ ID NO:86; (r) SEQ ID NO:83 and SEQ ID NO:34; (s) SEQ ID NO:83 and SEQ ID NO:84; or (t) SEQ ID NO:83 and SEQ ID NO:86.

Suitably, the first and second target-hybridizing sequences respectively comprise or consist of the nucleotide sequences of: (a) SEQ ID NO:2 and SEQ ID NO:27; (b) SEQ ID NO:4 and SEQ ID NO:21; (c) SEQ ID NO:8 and SEQ ID NO:21; (d) SEQ ID NO:8 and SEQ ID NO:34; (e) SEQ ID NO:8 and SEQ ID NO:84; (f) SEQ ID NO:8 and SEQ ID NO:86; (g) SEQ ID NO:83 and SEQ ID NO:34; (h) SEQ ID NO:83 and SEQ ID NO:84; or (i) SEQ ID NO:83 and SEQ ID NO:86.

Suitably, the combination further comprises at least one capture probe oligomer.

Suitably, the at least one capture probe oligomer comprises a target-hybridizing sequence covalently attached to a sequence or moiety that binds to an immobilized probe, wherein said target-hybridizing sequence (i) is from about 15 to about 21 contiguous nucleotides contained in the sequence of SEQ ID NO:78, or (ii) is about 21 to 30 contiguous nucleotides comprising the sequence of SEQ ID NO:78; or (iii) the sequence consists of SEQ ID NO:44.

Suitably, the capture probe oligomer sequence comprises or consists of SEQ ID NO:43.

Suitably, the combination further comprises a detection probe oligomer.

Suitably, the detection probe oligomer comprises a target-hybridizing sequence that is from about 14 to about 40 nucleotides in length and is configured to specifically hybridize to a target sequence contained in SEQ ID NO:59, the RNA equivalent of SEQ ID NO:59, the complement of SEQ ID NO:59, the RNA equivalent of the complement of SEQ ID NO:59, SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence contains the sequence of SEQ ID NO:59 and includes at least the sequence of SEQ ID NO:42, 92, 94, or 99.

Suitably, the detection probe target-hybridizing sequence contains the sequence of SEQ ID NO:60 and includes at least the sequence of SEQ ID NO:38 or SEQ ID NO:39.

Suitably, the detection probe target hybridising sequence consists of the sequence selected from the group consisting of: SEQ ID NO:37, 38, 39, 40, 41, 42, 59, 60, 91, 92, 93, 94, 98 or 99.

Suitably, the detection probe oligomer comprises a nucleotide sequence that is from 16 to 25 contiguous nucleotides in length and specifically hybridizes to SEQ ID NO:65, or the DNA equivalent thereof; or specifically hybridizes to the complement of SEQ ID NO:65, or the DNA equivalent thereof.

Suitably, the detection probe oligomer sequence further comprises a nucleotide sequence containing SEQ ID NO:59 or SEQ ID NO:60.

Suitably, the detection probe oligomer further comprises a nucleotide sequence consisting of SEQ ID NO:37, 38, 39, 40, 41, 42, 59, 60, 91, 92, 93, 94, 98 or 99.

Suitably, the detection probe oligomer further comprises a 2' methoxy modification on at least one nucleotide residue member of the nucleotide sequence.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:11 and SEQ ID NO:39 or SEQ ID NO:37; (b) SEQ ID NO:2 and SEQ ID NO:27 and SEQ ID NO:38 or SEQ ID NO:39; (c) SEQ ID NO:4 and SEQ ID NO:13 and SEQ ID NO:39 or SEQ ID NO:37; (d) SEQ ID NO:4 and SEQ ID NO:16 or SEQ ID NO:17 and SEQ ID NO:39; (e) SEQ ID NO:4 and SEQ ID NO:18 or SEQ ID NO:19 and SEQ ID NO:39 or SEQ ID NO:37; (f) SEQ ID NO:4 and SEQ ID NO:20 and SEQ ID NO:39 or SEQ ID NO:37; (g) SEQ ID NO:4 and SEQ ID NO:21 and SEQ ID NO:39 or SEQ ID NO:37; (h) SEQ ID NO:4 and SEQ ID NO:27 and SEQ ID NO:39 or SEQ ID NO:38; (i) SEQ ID NO:4 and SEQ ID NO:28 and SEQ ID NO:39; (j) SEQ ID NO:4 and SEQ ID NO:29 and SEQ ID NO:39 or SEQ ID NO:37; (k) SEQ ID NO:4 and SEQ ID NO:31 and SEQ ID NO:39; (1) SEQ ID NO:6 and SEQ ID NO:11 and SEQ ID NO:37; (m) SEQ ID NO:6 and SEQ ID NO:13 and SEQ ID NO:37; (n) SEQ ID NO:6 and SEQ ID NO:21 and SEQ ID NO:37; (o) SEQ ID NO:8 and SEQ ID NO:21 and SEQ ID NO:39 or SEQ ID NO:37 or SEQ ID NO:42; (p) SEQ ID NO:8 and SEQ ID NO:27 and SEQ ID NO:39; (q) SEQ ID NO:8 and SEQ ID NO:32 and SEQ ID NO:37 or SEQ ID NO:42; (r) SEQ ID NO:8 and SEQ ID NO:33 and SEQ ID NO:37 or SEQ ID NO:42; (s) SEQ ID NO:8 and SEQ ID NO:34 and SEQ ID NO:37 or SEQ ID NO:42; (t) SEQ ID NO:8 and SEQ ID NO:35 and SEQ ID NO:37 or SEQ ID NO:42; (u) SEQ ID NO:8 and SEQ ID NO:36 and SEQ ID NO:37 or SEQ ID NO:42; (v) SEQ ID NO:8, and SEQ ID NO:84, and SEQ ID NOs:91, 92 and/or 93; (w) SEQ ID NO:8, and SEQ ID NO:86, and SEQ ID NOs:91, 92 and/or 93; (x) SEQ ID NO:83, and SEQ ID NO:34, and SEQ ID NOs:91, 92 and/or 93; (y) SEQ ID NOs:83, and SEQ ID NO:84, and SEQ ID NOs:91, 92 and/or 93; (z) SEQ ID NOs:83, and SEQ ID NO:86, and SEQ ID NOs:91, 92 and/or 93; or (aa) SEQ ID NO:8 or 83, SEQ ID NO:34, 84 or 86, and SEQ ID NO:37, 38, 39, 40, 41, 42, 59, 60, 91, 92, 93, 94, 98 or 99.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:27 and SEQ ID NO:38; (b) SEQ ID NO:4 and SEQ ID NO:21 and SEQ ID NO:39; (c) SEQ ID NO:8 and SEQ ID NO:21 and SEQ ID NO:37 or SEQ ID NO:39; (d) SEQ ID NO:8 and SEQ ID NO:34 and SEQ ID NO:37 or SEQ ID NO:42; (e) SEQ ID NO:8, and SEQ ID NO:84, and SEQ ID NOs:91, 92 and/or 93; (f) SEQ ID NO:8, and SEQ ID NO:86, and SEQ ID NOs:91, 92 and/or 93; (g) SEQ ID NO:83, and SEQ ID NO:34, and SEQ ID NOs:91, 92 and/or 93; (h) SEQ ID NOs:83, and SEQ ID NO:84, and SEQ ID NOs:91, 92 and/or 93; (i) SEQ ID NOs:83, and SEQ ID NO:86, and SEQ ID NOs:91, 92 and/or 93; or (j) SEQ ID NO:8 or 83, SEQ ID NO:34, 84 or 86, and SEQ ID NO:37, 38, 39, 40, 41, 42, 59, 60, 91, 92, 93, 94, 98 or 99.

Suitably, the detection probe comprises a label. Suitably, the label is a chemiluminescent label or a fluorescent label. Suitably, the detection probe comprises a fluorescent label and a quencher. Suitably, the detection probe is selected from the group consisting of a molecular torch, a molecular beacon, and a TaqMan detection probe. Suitably, the detection probe further comprises a non-target-hybridizing sequence. Suitably, the detection probe is a molecular torch or a molecular beacon.

In a further aspect, there is described a detection probe oligomer comprising a target-hybridizing sequence that is from about 14 to about 40 nucleotides in length and is configured to specifically hybridize to a target sequence contained in SEQ ID NO:59, the RNA equivalent of SEQ ID NO:59, the complement of SEQ ID NO:59, the RNA equivalent of the complement of SEQ ID NO:59, SEQ ID NO:65, the RNA equivalent of SEQ ID NO:65, the complement of SEQ ID NO:65, or the RNA equivalent of the complement of SEQ ID NO:65.

Suitably, the detection probe target-hybridizing sequence is contained in the sequence of SEQ ID NO:59 and includes at least the sequence of SEQ ID NO:42, 92, 94 or 99.

Suitably, the detection probe target-hybridizing sequence is contained in the sequence of SEQ ID NO:65 and includes at least the sequence of SEQ ID NO:59 or SEQ ID NO:94.

Suitably, the detection probe target hybridising sequence consists of the sequence selected from the group consisting of: SEQ ID NOs:37, 38, 39, 40, 41, 42, 59, 60, 91, 92, 93, 94, 98 and 99.

Suitably, the detection probe oligomer further comprises a 2' methoxy modification on at least one nucleotide residue member of the nucleotide sequence.

Suitably, the detection probe comprises a label. Suitably, the label is a chemiluminescent label or a fluorescent label. Suitably, the detection probe comprises a fluorescent label and a quencher. Suitably, the detection probe is selected from the group consisting of a molecular torch, a molecular beacon, and a TaqMan detection probe.

Suitably, the detection probe further comprises a non-target-hybridizing sequence.

Suitably, the detection probe is a molecular torch or a molecular beacon.

In a further aspect, there is described a capture probe oligomer for specifically isolating *Babesia* species nucleic acid from a sample, said capture probe oligomer comprising a target-hybridizing sequence covalently attached to a sequence or moiety that binds to an immobilized probe, wherein said target-hybridizing sequence is from about 15 to about 30 contiguous nucleotides contained in the sequence of SEQ ID NO:78.

Suitably, the capture probe oligomer sequence comprises or consists of SEQ ID NO:43.

In a further aspect, there is described a kit comprising the combination of at least two oligomers according to any of claims 78 to 107.

In a further aspect, there is described a reaction mixture comprising the combination of at least two oligomers according to any of claims 78 to 107.

In a further aspect, there is described the use of the combination of at least two oligomers according to any of claims 78 to 107 for specifically amplifying *Babesia* species nucleic acid in a sample.

In a further aspect, there is described the use of the detection probe oligomer according to any of claims 108 to 121 for specifically detecting *Babesia* species nucleic acid in a sample.

In a further aspect, there is described the use of the capture probe oligomer according to claim 112 or 123 for specifically capturing *Babesia* species nucleic acid from a sample.

Suitably, *Babesia microti* and/or *Babesia divergens* and/or *Babesia duncani* and/or *Babesia venatorum* are detected.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

"Sample" includes any specimen that may contain, or is suspected of containing, *Babesia* nucleic acid or components thereof, such as nucleic acids or fragments of *Babesia* nucleic acids. The sample may be an isolated sample. Samples include "biological samples" which include any tissue or material derived from a living or dead human that may contain the *Babesia* parasite or components thereof (e.g., a target nucleic acid derived therefrom), including, e.g., blood, peripheral blood and red blood cells. The use of other sample types that may contain the *Babesia* parasite or components thereof (e.g., a target nucleic acid derived therefrom)—such as plasma, serum, lymph node, gastrointestinal tissue, faeces, urine, semen or other body fluids or materials—is also contemplated. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see WO95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; The Biochemistry of the Nucleic Acids 5-36, Adams et al, ed., 11th ed., 1992, BioTechniques (2007) 43: 617-24), which include derivatives of purine or pyrimidine bases (e.g., N4-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, 06-methylguanine, 4-thio-pyrimidines, 4-amino-pyrimidines, 4-dimethylhydrazine-pyrimidines, and 04-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Biochemistry (2004) 43: 13233-41). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

The term "polynucleotide," as used herein, denotes a nucleic acid chain. Throughout this application, nucleic acids are designated by the 5'-terminus to the 3'-terminus. Standard nucleic acids, e.g., DNA and RNA, are typically synthesized "5'-to-3'," i.e., by the addition of nucleotides to the 3'-terminus of a growing nucleic acid.

A "nucleotide," as used herein, is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-0-Me).

A "nucleic-acid-based detection assay," as used herein, is an assay for the detection of a target sequence within a target nucleic acid and utilizing one more oligonucleotides that specifically hybridize to the target sequence.

In certain embodiments, a nucleic-acid-based detection assay is an "amplification-based assay," i.e., an assay that utilizes one or more steps for amplifying a nucleic acid target sequence. Various amplification methods for use in detection assays are known in the art, several of which are summarized further herein. For the sake of clarity, an amplification-based assay may include one or more steps that do not amplify a target sequence, such as, for example, steps used in non-amplification-based assay methods (e.g., a hybridization assay or a cleavage-based assay).

In other embodiments, a nucleic-acid-based detection assay is a "non-amplification-based assay," i.e., an assay that does not rely on any step for amplifying a nucleic acid target sequence. For the sake of clarity, a nucleic-acid-based detection assay that includes a reaction for extension of a primer in the absence of any corresponding downstream amplification oligomer (e.g., extension of a primer by a reverse transcriptase to generate an RNA:DNA duplex followed by an RNase digestion of the RNA, resulting in a single-stranded cDNA complementary to an RNA target but without generating copies of the cDNA) is understood to be a non-amplification-based assay.

An exemplary non-amplification-based assay is a "cleavage-based assay," which is an assay that relies on the specific cleavage, by a flap endonuclease, of a linear duplex cleavage structure formed by the specific hybridization of overlapping oligonucleotides to a target nucleic acid. In these assays, a probe oligonucleotide containing a non-target-hybridizing flap region is cleaved in an overlap-dependent manner by the flap endonuclease to release a cleavage product that is then detected. The principles of cleavage-based assays are well-known in the art, and exemplary assays are described in, for example, Nat. Biotechnol. (1999) 17:292-296, Mol. Diagn. (1999) 4: 135-144, J. Clin. Microbiol. (2006) 44:3443-3447, and U.S. Pat. Nos. 5,846,717, 6,706,471 and 5,614,402. Cleavage-based assays include, e.g., the commercially available Invader® assays (Hologic, Inc., Madison, Wis.).

A "target nucleic acid," as used herein, is a nucleic acid comprising a target sequence to be detected. Target nucleic acids may be DNA or RNA as described herein, and may be either single-stranded or double-stranded. The target nucleic acid may include other sequences besides the target sequence.

By "isolated" it is meant that a sample containing a target nucleic acid is taken from its natural milieu, but the term does not connote any degree of purification.

The term "target sequence," as used herein, refers to the particular nucleotide sequence of a target nucleic acid that is to be detected. The "target sequence" includes the complexing sequences to which oligonucleotides (e.g., probe oligonucleotide, priming oligonucleotides and/or promoter oligonucleotides) complex during a detection process (e.g., an amplification-based detection assay such as, for example, TMA or PCR, or a non-amplification-based detection assay such as, for example, a cleavage-based assay). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various strains of *Babesia*. It is understood that other reasons exist for configuring a target-hybridizing sequence to have less than 100% complementarity to a target nucleic acid.

The term "targets a sequence," as used herein in reference to a region of *Babesia* sp. nucleic acid, refers to a process whereby an oligonucleotide hybridizes to the target sequence in a manner that allows for detection as described herein. In one embodiment, the oligonucleotide is complementary with the targeted *Babesia* sp. nucleic acid sequence and contains no mismatches. In another embodiment, the oligonucleotide is complementary but contains 1, 2, 3, 4, or 5 mismatches with the targeted *Babesia* sp. nucleic acid sequence. Preferably, the oligonucleotide that hybridizes to the target nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an oligonucleotide is designed to have a polynucleotide sequence that could target a sequence of the referenced *Babesia* sp. target region. Such an oligonucleotide is not limited to targeting that sequence only, but is rather useful as a composition, in a kit or in a method for targeting a *Babesia* sp. target nucleic acid. The oligonucleotide is designed to function as a component of an assay for detection of *Babesia* sp. from a sample, and therefore is designed to target *Babesia* sp. in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the oligonucleotide target-hybridizing sequence.

The term "fragment," as used herein in reference to a *Babesia* sp. targeted nucleic acid, refers to a piece of contiguous nucleic acid.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. As a non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound).

As used herein, an oligonucleotide can "substantially correspond to" a specified reference nucleic acid sequence, which means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide—such as a first amplification oligomer as described herein—may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

"Amplification" refers to any known procedure for obtaining multiple copies of a target nucleic acid sequence or its complement or fragments thereof. The multiple copies may be referred to as amplicons or amplification products. Known amplification methods include both thermal cycling and isothermal amplification methods. In some embodiments, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252; 5,547,861; and 5,648,211). Preferred embodiments use an amplification method suitable for the amplification of RNA target nucleic acids, such as transcription-mediated amplification (TMA) or NASBA, but it will be apparent to persons of ordinary skill in the art that oligomers disclosed herein may be readily used as primers in other amplification methods.

"Transcription-associated amplification," also referred to herein as "transcription-mediated amplification" (TMA), refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting HSV target sequences as described herein. Variations of transcription-associated amplification are well-known in the art as previously disclosed in detail (e.g., US Pat. Nos. 4,868, 105; 5,124,246; 5,130,238; 5,437,990; 5,554,516; and 7,374,885; and PCT Pub. Nos. WO 88/01302, WO 88/10315, and WO 95/03430). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon," which is used interchangeably with "amplification product," refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

"Probe," "detection probe," "detection oligonucleotide," and "detection probe oligomer" are used interchangeably herein to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417). In a preferred embodiment, the detection probe comprises a 2' methoxy backbone which can result in a higher signal being obtained.

The term "TaqMan® probe" refers to detection oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TaqMan probe to separate the fluorophore from the quencher, thereby allowing an unquenched signal to be emitted from the fluorophore as an indicator of amplification.

As used herein, a "label" refers to a moiety or compound joined directly or indirectly to a probe that is detected or leads to a detectable signal. Direct labelling can occur through bonds or interactions that link the label to the probe, including covalent bonds or non-covalent interactions, e.g., hydrogen bonds, hydrophobic and ionic interactions, or formation of chelates or coordination complexes. Indirect labelling can occur through use of a bridging moiety or "linker" such as a binding pair member, an antibody or additional oligomer, which is either directly or indirectly labeled, and which may amplify the detectable signal.

Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., US Pat. Nos. 5,283, 174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., Molecular Cloning, A Laboratory Manual, 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283, 174, and 4,581,333). More than one label, and more than one type of label, may be present on a particular probe, or detection may use a mixture of probes in which each probe is labeled with a compound that produces a detectable signal (e.g., US Pat. Nos. 6, 180,340 and 6,350,579).

As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

"Capture probe," "capture oligonucleotide," "target capture oligonucleotide," and "capture probe oligomer" are used interchangeably herein to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-GU, poly-GT, or poly U sequences to bind non-specifically to a target nucleic acid and link it to an immobilized probe on a support (see, e.g., WO 2008/016988). The immobilized probe binding region can be a nucleic acid sequence, referred to as a tail. Tails include a substantially homopolymeric tail of about 10 to 40 nucleotides (e.g., Aio to A40), or of about 14 to 33 nt (e.g., T3A14 to T3A30), that bind to a complementary immobilized sequence attached to the support particle or support matrix. Thus, a non-limiting example of preferred nucleic acid tails can in some embodiments include T0-4A1040 sequences. Another example of a capture oligomer comprises two regions, a target hybridizing sequence and a binding pair member that is not a nucleic acid sequence.

As used herein, an "immobilized oligonucleotide," "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size+ 5%), to which an immobilized probe is joined directly (via covalent linkage, chelation, or ionic interaction), or indirectly (via one or more linkers), where the linkage or interaction between the probe and support is stable during hybridization conditions.

DESCRIPTION

The present disclosure is generally directed to methods and compositions for determining the presence or absence of the protozoan parasite *Babesia* sp. in a sample—such as a blood sample. Suitably, the methods and compositions described herein are able to detect the presence of *Babesia microti* and/or *Babesia divergens* and/or *Babesia duncani* and/or *Babesia venatorum*. In some embodiments, the present disclosure provides methods and compositions for diagnosing Babesiosis in a subject. In other, non-mutually exclusive embodiments, the present disclosure provides methods for the detection of *Babesia* sp. in a sample, where the method includes performing amplification-based detection of a target nucleic from *Babesia* sp. The present disclosure further provides compositions (including reaction mixtures) and kits comprising a combination of oligomers for detecting *Babesia* sp.— including *Babesia microti* and/or *Babesia divergens* and/or *Babesia duncani* and/or *Babesia venatorum*—in a sample. The oligomer combination generally includes at least two amplification oligomers for detecting *Babesia* sp.—including *Babesia microti* and/or *Babesia divergens* and/or *Babesia duncani* and/or *Babesia* venatorum—in a sample, and may further include one or more additional oligomers as described herein for performing amplification-based detection of *Babesia* sp.—including *Babesia microti* and/or *Babesia divergens* and/or *Babesia duncani* and/or *Babesia venatorum*—such as, for example, a capture probe and/or a detection probe.

The methods for diagnosing Babesiosis sp. generally include detecting the presence or absence of *Babesia* sp. in a sample from a subject. The sample may be suspected of being infected with or containing *Babesia* sp. The subject may be suspected of being infected with *Babesia* sp. or having Babesiosis. In particular, an assay is performed for the specific detection in the sample of *Babesia* sp. nucleic acid. Based on the results from the detection assay, a status of either positive or negative is assigned for the *Babesia* sp. The presence or absence of Babesiosis in the subject can be determined based on the *Babesia* sp. status.

While *Babesia* sp. nucleic acid may be detected using any suitable method, it is preferred that these protozoan parasites are detected using a nucleic-acid-based detection assay. Nucleic-acid-based detection assays generally utilize oligonucleotides that specifically hybridize to a target nucleic acid of *Babesia* sp. with minimal cross-reactivity to other nucleic acids suspected of being in a sample. Accordingly, oligonucleotides for nucleic-acid-based detection of *Babesia* sp. will have minimal cross-reactivity to other nucleic acids including, for example, *P. falciparum.*

A positive signal from a nucleic-acid-based detection assay in accordance with the present disclosure is indicative of the presence of one or more of *Babesia microti, Babesia divergens, Babesia duncani* and/or *Babesia venatorum* in a sample.

In some embodiments of a method comprising the use of a nucleic-acid-base detection assay—such as an amplification-based assay—is used to detect *Babesia* sp. Such methods generally include amplifying a target sequence within a target nucleic acid utilizing an in vitro nucleic acid amplification reaction and detecting the amplified product by, for example, specifically hybridizing the amplified product with a nucleic acid detection probe that provides a signal to indicate the presence of a target in the sample. The amplification step includes contacting the sample with two or more amplification oligomers specific for a target sequence in a target nucleic acid to produce an amplified product if the target nucleic acid is present in the sample. Amplification synthesizes additional copies of the target sequence or its complement such as, e.g., by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected amplification oligomers. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art (see, e.g., discussion of amplification methods in Definitions section, supra) and are readily used in accordance with the methods of the present disclosure.

For example, some amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configure to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5 '-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

In one aspect, there is provided a method for specifically detecting *Babesia* species nucleic acid in a sample, which comprises the use of at least two amplification oligomers comprising (a) a first amplification oligomer comprising a first target-hybridizing sequence (i) that is from about 15 to about 33 contiguous nucleotides in length, is contained in the sequence of SEQ ID NO:66 and comprises SEQ ID NO:56 or 57; or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises or consists of SEQ ID NO:8; (v) comprises or consists of SEQ ID NO:83 and (b) a second amplification oligomer comprising a second target-hybridizing sequence that is from about 15 to about 33 contiguous nucleotides in length, and (i) is contained in SEQ ID NO:68 and comprises SEQ ID NO:52, SEQ ID NO:53, SEQ ID NO:54, SEQ ID NO:55, or SEQ ID NO:85; or (ii) is contained in SEQ ID NO:67 and comprises SEQ ID NO:45 or SEQ ID NO:52; or (iii) is contained in SEQ ID NO:70 and comprises SEQ ID NO:46, SEQ ID NO:47, SEQ ID NO:48, SEQ ID NO:49, SEQ ID NO:50, or SEQ ID NO:51; or (iv) comprises or consists of SEQ ID NO:84. In certain embodiments comprising an amplification-based detection assay, a combination of at least two amplification oligomers is therefore utilized for the detection of a *Babesia* sp. nucleic acid.

Suitably, the first amplification oligomer comprises or consists of a sequence selected from the group consisting of: SEQ ID NOs:2 and 4 and 6 and 8 and 83, more suitably, wherein the first amplification oligomer comprises or consists of the sequence selected from the group consisting of: SEQ ID NOs:2 and 4 and 8 and 83.

The first amplification oligomer of the combination may be a promoter primer or promoter provider further comprising a promoter sequence located 5' to the first target-hybridizing sequence. Suitably, the promoter sequence is a T7 promoter sequence which optionally comprises or consists of SEQ ID NO:58. According to this embodiment, the first amplification oligomer may comprise or consist of a sequence selected from the group consisting of SEQ ID NOs:1 and 3 and 5 and 7 and 82, suitably, wherein the first amplification oligomer comprises or consists of a sequence selected from the group consisting of SEQ ID NOs:1 and 3 and 7 and 82.

Suitably, the second amplification oligomer comprises or consists of a sequence selected from the group consisting of: SEQ ID NOs:13, 16, 17, 18, 19, 20, 21, 27, 28, 29, 31, 32, 33, 34, 35,36, 84, and 86. More suitably, the second amplification oligomer sequence comprises or consists of SEQ ID NO:21 or SEQ ID NO:27 or SEQ ID NO:34 or SEQ ID NO:84 or SEQ ID NO:86.

In one embodiment, the first and second target-hybridizing sequences respectively comprise or consist of the nucleotide sequences of: (a) SEQ ID NO:2 or 6 and SEQ ID NO:11; (b) SEQ ID NO:4 or 6 and SEQ ID NO:13; (c) SEQ ID NO:4 and SEQ ID NO:16 or SEQ ID NO:17; (d) SEQ ID NO:4 and SEQ ID NO:18 or SEQ ID NO:19; (e) SEQ ID NO:4 and SEQ ID NO:20; (1) SEQ ID NO:4 or 6 or 8 and SEQ ID NO:21; (g) SEQ ID NO:2 or 4 or 8 and SEQ ID NO:27; (h) SEQ ID NO:4 and SEQ ID NO:28; (i) SEQ ID NO:4 and SEQ ID NO:29; (j) SEQ ID NO:4 and SEQ ID NO:31; (k) SEQ ID NO:8 and SEQ ID NO:32; (1) SEQ ID NO:8 and SEQ ID NO:33; (m) SEQ ID NO:8 and SEQ ID NO:34; (n) SEQ ID NO:8 and SEQ ID NO:35; (o) SEQ ID NO:8 and SEQ ID NO:36; (p) SEQ ID NO:8 and SEQ ID NO:84; (q) SEQ ID NO:8 and SEQ ID NO:86; (r) SEQ ID NO:83 and SEQ ID NO:34; (s) SEQ ID NO:83 and SEQ ID NO:84; or (t) SEQ ID NO:83 and SEQ ID NO:86.

In another embodiment, the first and second target-hybridizing sequences respectively comprise or consist of the nucleotide sequences of: (a) SEQ ID NO:2 and SEQ ID NO:27; (b) SEQ ID NO:4 and SEQ ID NO:21; (c) SEQ ID NO:8 and SEQ ID NO:21; (d) SEQ ID NO:8 and SEQ ID NO:34; (e) SEQ ID NO:8 and SEQ ID NO:84; (f) SEQ ID NO:8 and SEQ ID NO:86; (g) SEQ ID NO:83 and SEQ ID NO:34; (h) SEQ ID NO:83 and SEQ ID NO:84; or (i) SEQ ID NO:83 and SEQ ID NO:86.

In embodiments where the combination further includes one or more detection probe oligomers, the first and second amplification oligomer target-hybridizing sequences and the detection probe oligomer target-hybridizing sequences respectively may comprise or consist of the nucleotide sequences of: (a) SEQ ID NO:2 and SEQ ID NO:11 and SEQ ID NO:39 or SEQ ID NO:37; (b) SEQ ID NO:2 and SEQ ID NO:27 and SEQ ID NO:38 or SEQ ID NO:39; (c) SEQ ID NO:4 and SEQ ID NO:13 and SEQ ID NO:39 or SEQ ID NO:37; (d) SEQ ID NO:4 and SEQ ID NO:16 or SEQ ID NO:17 and SEQ ID NO:39; (e) SEQ ID NO:4 and SEQ ID NO:18 or SEQ ID NO:19 and SEQ ID NO:39 or SEQ ID NO:37; (f) SEQ ID NO:4 and SEQ ID NO:20 and SEQ ID NO:39 or SEQ ID NO:37; (g) SEQ ID NO:4 and SEQ ID NO:21 and SEQ ID NO:39 or SEQ ID NO:37; (h) SEQ ID NO:4 and SEQ ID NO:27 and SEQ ID NO:39 or SEQ ID NO:38; (i) SEQ ID NO:4 and SEQ ID NO:28 and SEQ ID NO:39; (j) SEQ ID NO:4 and SEQ ID NO:29 and SEQ ID NO:39 or SEQ ID NO:37; (k) SEQ ID NO:4 and SEQ ID NO:31 and SEQ ID NO:39; (1) SEQ ID NO:6 and SEQ ID NO:11 and SEQ ID NO:37; (m) SEQ ID NO:6 and SEQ ID NO:13 and SEQ ID NO:37; (n) SEQ ID NO:6 and SEQ ID NO:21 and SEQ ID NO:37; (o) SEQ ID NO:8 and SEQ ID NO:21 and SEQ ID NO:39 or SEQ ID NO:37 or SEQ ID NO:42; (p) SEQ ID NO:8 and SEQ ID NO:27 and SEQ ID NO:39; (q) SEQ ID NO:8 and SEQ ID NO:32 and SEQ ID NO:37 or SEQ ID NO:42; (r) SEQ ID NO:8 and SEQ ID NO:33 and SEQ ID NO:37 or SEQ ID NO:42; (s) SEQ ID NO:8 and SEQ ID NO:34 and SEQ ID NO:37 or SEQ ID NO:42; (t) SEQ ID NO:8 and SEQ ID NO:35 and SEQ ID NO:37 or SEQ ID NO:42; (u) SEQ ID NO:8 and SEQ ID NO:36 and SEQ ID NO:37 or SEQ ID NO:42; (v) SEQ ID NO:8, and SEQ ID NO:84, and SEQ ID NOs:91, 92 and/or 93; (w) SEQ ID NO:8, and SEQ ID NO:86, and SEQ ID NOs:91, 92 and/or 93; (x) SEQ ID NO:83, and SEQ ID NO:34, and SEQ ID NOs:91, 92 and/or 93; (y) SEQ ID NOs:83, and SEQ ID NO:84, and SEQ ID NOs:91, 92 and/or 93; (z) SEQ ID NOs:83, and SEQ ID NO:86, and SEQ ID NOs:91, 92 and/or 93; or (aa) SEQ ID NO:8 or 83, SEQ ID NO:34, 84 or 86, and SEQ ID NO:37, 38, 39, 40, 41, 42, 59, 60, 91, 92, 93, 94, 98 or 99.

In other embodiments where the combination further include one or more detection probe oligomers, the first and second amplification oligomer target-hybridizing sequences and the detection probe oligomer target-hybridizing sequences respectively may comprise or consist of the nucleotide sequences of: (a) SEQ ID NO:2 and SEQ ID NO:27 and SEQ ID NO:38; (b) SEQ ID NO:4 and SEQ ID NO:21 and SEQ ID NO:39; (c) SEQ ID NO:8 and SEQ ID NO:21 and SEQ ID NO:37 or SEQ ID NO:39; (d) SEQ ID NO:8 and SEQ ID NO:34 and SEQ ID NO:37 or SEQ ID NO:42; (e) SEQ ID NO:8, and SEQ ID NO:84, and SEQ ID NOs:91, 92 and/or 93; (1) SEQ ID NO:8, and SEQ ID NO:86, and SEQ ID NOs:91, 92 and/or 93; (g) SEQ ID NO:83, and SEQ ID NO:34, and SEQ ID NOs:91, 92 and/or 93; (h) SEQ ID NOs:83, and SEQ ID NO:84, and SEQ ID NOs:91, 92 and/or 93; (i) SEQ ID NOs:83, and SEQ ID NO:86, and SEQ ID NOs:91, 92 and/or 93; or (j) SEQ ID NO:8 or 83, SEQ ID NO:34, 84 or 86, and SEQ ID NO:37, 38, 39, 40, 41, 42, 59, 60, 91, 92, 93, 94, 98 or 99.

As will be appreciated, the present disclosure contemplates the use of various combinations of first and second amplification oligomers, including: a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:52; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:53; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:54; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:55; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:85; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:67 and comprises SEQ ID NO:45; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:67 and comprises SEQ ID NO:52; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:46; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:47; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:48; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:49; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:50; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:51; and a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising or consisting of SEQ ID NO:84.

Further combinations of first and second amplification oligomers, include: a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:52; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:53; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:54; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:55; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:85; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:67 and comprises SEQ ID NO:45; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:67 and comprises SEQ ID NO:52; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:46; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:47; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:48; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:49; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:50; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:51; and a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising or consisting of SEQ ID NO:84.

Further combinations of first and second amplification oligomers, include: a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:52; a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:53; a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:54; a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:55; a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:85; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:67 and comprises SEQ ID NO:45; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:67 and comprises SEQ ID NO:52; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:46; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:47; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:48; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:49; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:50; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:51; and a first amplification oligomer comprising or consisting of SEQ ID NO:8 or 83 and a second amplification oligomer comprising or consisting of SEQ ID NO:84.

The present disclosure also contemplates the use of other combinations of first and second amplification oligomers, including amplification oligomers in which: the first target-hybridizing sequence comprises or consists of SEQ ID NO:2 and the second target-hybridizing sequence comprises or consists of SEQ ID NO:13; the first target-hybridizing sequence comprises or consists of SEQ ID NO:2 and the second target-hybridizing sequence comprises or consists of SEQ ID NO:16; the first target-hybridizing sequence comprises or consists of SEQ ID NO:2 and the second target-hybridizing sequence comprises or consists of SEQ ID NO:17; the first target-hybridizing sequence comprises or consists of SEQ ID NO:2 and the second target-hybridizing sequence comprises or consists of SEQ ID NO:18; the first target-hybridizing sequence comprises or consists of SEQ ID NO:2 and the second target-hybridizing sequence comprises or consists of SEQ ID NO:19; the first target-hybridizing sequence comprises or consists of SEQ ID NO:2 and the second target-hybridizing sequence comprises or consists of SEQ ID NO:20; the first target-hybridizing sequence comprises or consists of SEQ ID NO:2 and the second target-hybridizing sequence comprises or consists of SEQ ID NO:21; the first target-hybridizing sequence comprises or consists of SEQ ID NO:2 and the second target-hybridizing sequence comprises or consists of SEQ ID NO:27; the first target-hybridizing sequence comprises or consists of SEQ ID NO:2 and the second target-hybridizing sequence comprises or consists of SEQ ID NO:28; the first target-hybridizing sequence comprises or consists of SEQ ID NO:2 and the second target-hybridizing sequence comprises or consists of SEQ ID NO:29; the first target-hybridizing sequence comprises or consists of SEQ ID NO:2 and the second target-hybridizing sequence comprises or consists of SEQ ID NO:31; the first target-hybridizing sequence comprises or consists of SEQ ID NO:2 and the second target-hybridizing sequence comprises or consists of SEQ ID NO:32; the first target-hybridizing sequence comprises or consists of SEQ ID NO:2 and the second target-hybridizing sequence comprises or consists of SEQ ID NO:33; the first target-hybridizing sequence comprises or consists of SEQ ID NO:2 and the second target-hybridizing sequence comprises or consists of SEQ ID NO:34; the first target-hybridizing sequence comprises or consists of SEQ ID NO:2 and the second target-hybridizing sequence comprises or consists of SEQ ID NO:35; and the first target-hybridizing sequence comprises or consists of SEQ ID NO:2 and the second target-hybridizing sequence comprises or consists of SEQ ID NO:36.

The present disclosure also contemplates the use of other combinations of first and second amplification oligomers, including amplification oligomers in which: the first target-hybridizing sequence comprises or consists of SEQ ID NO:4 and the second target-hybridizing sequence comprises or consists of SEQ ID NO:13; the first target-hybridizing sequence comprises or consists of SEQ ID NO:4 and the second target-hybridizing sequence comprises or consists of SEQ ID NO:16; the first target-hybridizing sequence comprises or consists of SEQ ID NO:4 and the second target-hybridizing sequence comprises or consists of SEQ ID NO:17; the first target-hybridizing sequence comprises or consists of SEQ ID NO:4 and the second target-hybridizing sequence comprises or consists of SEQ ID NO:18; the first target-hybridizing sequence comprises or consists of SEQ ID NO:4 and the second target-hybridizing sequence comprises or consists of SEQ ID NO:19; the first target-hybridizing sequence comprises or consists of SEQ ID NO:4 and the second target-hybridizing sequence comprises or consists of SEQ ID NO:20; the first target-hybridizing sequence comprises or consists of SEQ ID NO:4 and the second target-hybridizing sequence comprises or consists of SEQ ID NO:21; the first target-hybridizing sequence comprises or consists of SEQ ID NO:4 and the second target-hybridizing sequence comprises or consists of SEQ ID NO:27; the first target-hybridizing sequence comprises or consists of SEQ ID NO:4 and the second target-hybridizing sequence comprises or consists of SEQ ID NO:28; the first target-hybridizing sequence comprises or consists of SEQ ID NO:4 and the second target-hybridizing sequence comprises or consists of SEQ ID NO:29; the first target-hybridizing sequence comprises or consists of SEQ ID NO:4 and the second target-hybridizing sequence comprises or consists of SEQ ID NO:31; the first target-hybridizing sequence comprises or consists of SEQ ID NO:4 and the second target-hybridizing sequence comprises or consists of SEQ ID NO:32; the first target-hybridizing sequence comprises or consists of SEQ ID NO:4 and the second target-hybridizing sequence comprises or consists of SEQ ID NO:33; the first target-hybridizing sequence comprises or consists of SEQ ID NO:4 and the second target-hybridizing sequence comprises or consists of SEQ ID NO:34; the first target-hybridizing sequence comprises or consists of SEQ ID NO:4 and the second target-hybridizing sequence comprises or consists of SEQ ID NO:35; and the first target-hybridizing sequence comprises or consists of SEQ ID NO:4 and the second target-hybridizing sequence comprises or consists of SEQ ID NO:36.

The present disclosure also contemplates the use of other combinations of first and second amplification oligomers, including amplification oligomers in which: the first target-hybridizing sequence comprises or consists of SEQ ID NO:6 and the second target-hybridizing sequence comprises or consists of SEQ ID NO:13; the first target-hybridizing sequence comprises or consists of SEQ ID NO:6 and the second target-hybridizing sequence comprises or consists of SEQ ID NO:16; the first target-hybridizing sequence comprises or consists of SEQ ID NO:6 and the second target-hybridizing sequence comprises or consists of SEQ ID NO:17; the first target-hybridizing sequence comprises or consists of SEQ ID NO:6 and the second target-hybridizing sequence comprises or consists of SEQ ID NO:18; the first target-hybridizing sequence comprises or consists of SEQ ID NO:6 and the second target-hybridizing sequence comprises or consists of SEQ ID NO:19; the first target-hybridizing sequence comprises or consists of SEQ ID NO:6 and the second target-hybridizing sequence comprises or consists of SEQ ID NO:20; the first target-hybridizing sequence comprises or consists of SEQ ID NO:6 and the second target-hybridizing sequence comprises or consists of SEQ ID NO:21; the first target-hybridizing sequence comprises or consists of SEQ ID NO:6 and the second target-hybridizing sequence comprises or consists of SEQ ID NO:27; the first target-hybridizing sequence comprises or consists of SEQ ID NO:6 and the second target-hybridizing sequence comprises or consists of SEQ ID NO:28; the first target-hybridizing sequence comprises or consists of SEQ ID NO:6 and the second target-hybridizing sequence comprises or consists of SEQ ID NO:29; the first target-hybridizing sequence comprises or consists of SEQ ID NO:6 and the second target-hybridizing sequence comprises or consists of SEQ ID NO:31; the first target-hybridizing sequence comprises or consists of SEQ ID NO:6 and the second target-hybridizing sequence comprises or consists of SEQ ID NO:32; the first target-hybridizing sequence comprises or consists of SEQ ID NO:6 and the second target-hybridizing sequence comprises or consists of SEQ ID NO:33; the first target-hybridizing sequence comprises or consists of SEQ ID NO:6 and the second target-hybridizing sequence comprises or consists of SEQ ID NO:34; the first target-hybridizing sequence comprises or consists of SEQ ID NO:6 and the second target-hybridizing sequence comprises or consists of SEQ ID NO:35; and the first target-hybridizing sequence comprises or consists of SEQ ID NO:6 and the second target-hybridizing sequence comprises or consists of SEQ ID NO:36.

The present disclosure also contemplates the use of other combinations of first and second amplification oligomers, including amplification oligomers in which: the first target-hybridizing sequence comprises or consists of SEQ ID NO:8 and the second target-hybridizing sequence comprises or consists of SEQ ID NO:13; the first target-hybridizing sequence comprises or consists of SEQ ID NO:8 and the second target-hybridizing sequence comprises or consists of SEQ ID NO:16; the first target-hybridizing sequence comprises or consists of SEQ ID NO:8 and the second target-hybridizing sequence comprises or consists of SEQ ID NO:17; the first target-hybridizing sequence comprises or consists of SEQ ID NO:8 and the second target-hybridizing sequence comprises or consists of SEQ ID NO:18; the first target-hybridizing sequence comprises or consists of SEQ ID NO:8 and the second target-hybridizing sequence comprises or consists of SEQ ID NO:19; the first target-hybridizing sequence comprises or consists of SEQ ID NO:8 and the second target-hybridizing sequence comprises or consists of SEQ ID NO:20; the first target-hybridizing sequence comprises or consists of SEQ ID NO:8 and the second target-hybridizing sequence comprises or consists of SEQ ID NO:21; the first target-hybridizing sequence comprises or consists of SEQ ID NO:8 and the second target-hybridizing sequence comprises or consists of SEQ ID NO:27; the first target-hybridizing sequence comprises or consists of SEQ ID NO:8 and the second target-hybridizing sequence comprises or consists of SEQ ID NO:28; the first target-hybridizing sequence comprises or consists of SEQ ID NO:8 and the second target-hybridizing sequence comprises or consists of SEQ ID NO:29; the first target-hybridizing sequence comprises or consists of SEQ ID NO:8 and the second target-hybridizing sequence comprises or consists of SEQ ID NO:31; the first target-hybridizing sequence comprises or consists of SEQ ID NO:8 and the second target-hybridizing sequence comprises or consists of SEQ ID NO:32; the first target-hybridizing sequence comprises or consists of SEQ ID NO:8 and the second target-hybridizing sequence comprises or consists of SEQ ID NO:33; the first target-hybridizing sequence comprises or consists of SEQ ID NO:8 and the second target-hybridizing sequence comprises or consists of SEQ ID NO:34; the first target-hybridizing sequence comprises or consists of SEQ ID NO:8 and the second target-hybridizing sequence comprises or consists of SEQ ID NO:35; the first target-hybridizing sequence comprises or consists of SEQ ID NO:8 and the second target-hybridizing sequence comprises or consists of SEQ ID NO:36; the first target-hybridizing sequence comprises or consists of SEQ ID NO:8 and the second target-hybridizing sequence comprises or consists of SEQ ID NO:84; and the first target-hybridizing sequence comprises or consists of SEQ ID NO:8 and the second target-hybridizing sequence comprises or consists of SEQ ID NO:86.

The present disclosure also contemplates the use of other combinations of first and second amplification oligomers, including amplification oligomers in which: the first target-hybridizing sequence comprises or consists of SEQ ID NO:83 and the second target-hybridizing sequence comprises or consists of SEQ ID NO:13; the first target-hybridizing sequence comprises or consists of SEQ ID NO:83 and the second target-hybridizing sequence comprises or consists of SEQ ID NO:16; the first target-hybridizing sequence comprises or consists of SEQ ID NO:83 and the second target-hybridizing sequence comprises or consists of SEQ ID NO:17; the first target-hybridizing sequence comprises or consists of SEQ ID NO:83 and the second target-hybridizing sequence comprises or consists of SEQ ID NO:18; the first target-hybridizing sequence comprises or consists of SEQ ID NO:83 and the second target-hybridizing sequence comprises or consists of SEQ ID NO:19; the first target-hybridizing sequence comprises or consists of SEQ ID NO:83 and the second target-hybridizing sequence comprises or consists of SEQ ID NO:20; the first target-hybridizing sequence comprises or consists of SEQ ID NO:83 and the second target-hybridizing sequence comprises or consists of SEQ ID NO:21; the first target-hybridizing sequence comprises or consists of SEQ ID NO:83 and the second target-hybridizing sequence comprises or consists of SEQ ID NO:27; the first target-hybridizing sequence comprises or consists of SEQ ID NO:83 and the second target-hybridizing sequence comprises or consists of SEQ ID NO:28; the first target-hybridizing sequence comprises or consists of SEQ ID NO:83 and the second target-hybridizing sequence comprises or consists of SEQ ID NO:29; the first target-hybridizing sequence comprises or consists of SEQ ID NO:83 and the second target-hybridizing sequence comprises or consists of SEQ ID NO:31; the first target-hybridizing sequence comprises or consists of SEQ ID NO:83 and the second target-hybridizing sequence comprises or consists of SEQ ID NO:32; the first target-hybridizing sequence comprises or consists of SEQ ID NO:83 and the second target-hybridizing sequence comprises or consists of SEQ ID NO:33; the first target-hybridizing sequence comprises or consists of SEQ ID NO:83 and the second target-hybridizing sequence comprises or consists of SEQ ID NO:34; the first target-hybridizing sequence comprises or consists of SEQ ID NO:83 and the second target-hybridizing sequence comprises or consists of SEQ ID NO:35; the first target-hybridizing sequence comprises or consists of SEQ ID NO:83 and the second target-hybridizing sequence comprises or consists of SEQ ID NO:36; the first target-hybridizing sequence comprises or consists of SEQ ID NO:83 and the second target-hybridizing sequence comprises or consists of SEQ ID NO:84; and the first target-hybridizing sequence comprises or consists of SEQ ID NO:83 and the second target-hybridizing sequence comprises or consists of SEQ ID NO:86.

The present disclosure also contemplates the use of other combinations of first and second amplification oligomers, wherein the first and second target-hybridizing sequences respectively comprise or consist of the nucleotide sequences of: SEQ ID NO:2 and SEQ ID NO:11; SEQ ID NO:6 and SEQ ID NO:11; SEQ ID NO:4 and SEQ ID NO:13; SEQ ID NO:6 and SEQ ID NO:13; SEQ ID NO:4 and SEQ ID NO:16; SEQ ID NO:4 and SEQ ID NO:17; SEQ ID NO:4 and SEQ ID NO:18; SEQ ID NO:4 and SEQ ID NO:19; SEQ ID NO:4 and SEQ ID NO:20; SEQ ID NO:4 and SEQ ID NO:21; SEQ ID NO:6 and SEQ ID NO:21; SEQ ID NO:8 and SEQ ID NO:21; SEQ ID NO:2 and SEQ ID NO:27; SEQ ID NO:4 and SEQ ID NO:27; SEQ ID NO:8 and SEQ ID NO:27; SEQ ID NO:4 and SEQ ID NO:28; SEQ ID NO:4 and SEQ ID NO:29; SEQ ID NO:4 and SEQ ID NO:31; SEQ ID NO:8 and SEQ ID NO:32; SEQ ID NO:8 and SEQ ID NO:33; SEQ ID NO:8 and SEQ ID NO:34; SEQ ID NO:8 and SEQ ID NO:84; SEQ ID NO:8 and SEQ ID NO:86; SEQ ID NO:8 and SEQ ID NO:35; SEQ ID NO:8 and SEQ ID NO:36; SEQ ID NO:83 and SEQ ID NO:32; SEQ ID NO:83 and SEQ ID NO:33; SEQ ID NO:83 and SEQ ID NO:34; SEQ ID NO:83 and SEQ ID NO:84; SEQ ID NO:83 and SEQ ID NO:86; SEQ ID NO:83 and SEQ ID NO:35; or SEQ ID NO:83 and SEQ ID NO:36.

The present disclosure also contemplates the use of combinations of a first amplification oligomer, a second amplification oligomer and a detection probe in which the first and second amplification oligomer target-hybridizing sequences and the detection probe oligomer target-hybridizing sequences respectively comprise or consist of the nucleotide sequences of: SEQ ID NO:2 and SEQ ID NO:11 and SEQ ID NO:39; SEQ ID NO:2 and SEQ ID NO:11 and SEQ ID NO:37; SEQ ID NO:2 and SEQ ID NO:27 and SEQ ID NO:38; SEQ ID NO:2 and SEQ ID NO:27 and SEQ ID NO:39; SEQ ID NO:4 and SEQ ID NO:13 and SEQ ID NO:39; SEQ ID NO:4 and SEQ ID NO:13 and SEQ ID NO:37; SEQ ID NO:4 and SEQ ID NO:16 and SEQ ID NO:39; SEQ ID NO:4 and SEQ ID NO:17 and SEQ ID NO:39; SEQ ID NO:4 and SEQ ID NO:18 and SEQ ID NO:39; SEQ ID NO:4 and SEQ ID NO:19 and SEQ ID NO:39; SEQ ID NO:4 and SEQ ID NO:18 and SEQ ID NO:37; SEQ ID NO:4 and SEQ ID NO:19 and SEQ ID NO:37; SEQ ID NO:4 and SEQ ID NO:20 and SEQ ID NO:39; SEQ ID NO:4 and SEQ ID NO:20 and SEQ ID NO:37; SEQ ID NO:4 and SEQ ID NO:21 and SEQ ID NO:39; SEQ ID NO:4 and SEQ ID NO:21 and SEQ ID NO:37; SEQ ID NO:4 and SEQ ID NO:27 and SEQ ID NO:39; SEQ ID NO:4 and SEQ ID NO:27 and SEQ ID NO:38; SEQ ID NO:4 and SEQ ID NO:28 and SEQ ID NO:39; SEQ ID NO:4 and SEQ ID NO:29 and SEQ ID NO:39; SEQ ID NO:4 and SEQ ID NO:29 and SEQ ID NO:37; SEQ ID NO:4 and SEQ ID NO:31 and SEQ ID NO:39; SEQ ID NO:6 and SEQ ID NO:11 and SEQ ID NO:37; SEQ ID NO:6 and SEQ ID NO:13 and SEQ ID NO:37; SEQ ID NO:6 and SEQ ID NO:21 and SEQ ID NO:37; SEQ ID NO:8 and SEQ ID NO:21 and SEQ ID NO:39; SEQ ID NO:8 and SEQ ID NO:21 and SEQ ID NO:37; SEQ ID NO:8 and SEQ ID NO:21 and SEQ ID NO:42; SEQ ID NO:8 and SEQ ID NO:27 and SEQ ID NO:39; SEQ ID NO:8 and SEQ ID NO:32 and SEQ ID NO:37; SEQ ID NO:8 and SEQ ID NO:32 and SEQ ID NO:42; SEQ ID NO:8 and SEQ ID NO:33 and SEQ ID NO:37; SEQ ID NO:8 and SEQ ID NO:33 and SEQ ID NO:42; SEQ ID NO:8 and SEQ ID NO:34 and SEQ ID NO:37; SEQ ID NO:8 and SEQ ID NO:34 and SEQ ID NO:42; SEQ ID NO:8 and SEQ ID NO:35 and SEQ ID NO:37; SEQ ID NO:8 and SEQ ID NO:35 and SEQ ID NO:42; SEQ ID NO:8 and SEQ ID NO:36 and SEQ ID NO:37; or SEQ ID NO:8 and SEQ ID NO:36 and SEQ ID NO:42; SEQ ID NO:8, and SEQ ID NO:84, and SEQ ID NOs:91, 92 and/or 93; SEQ ID NO:8, and SEQ ID NO:86, and SEQ ID NOs:91, 92 and/or 93; SEQ ID NO:83, and SEQ ID NO:34, and SEQ ID NOs:91, 92 and/or 93; SEQ ID NOs:83, and SEQ ID NO:84, and SEQ ID NOs:91, 92 and/or 93; SEQ ID NOs:83, and SEQ ID NO:86, and SEQ ID NOs:91, 92 and/or 93; or SEQ ID NO:8 or 83, SEQ ID NO:34, 84 or 86, and SEQ ID NO:37, 38, 39, 40, 41, 42, 59, 60, 91, 92, 93, 94, 98 or 99.

In a further aspect, there is described a method for specifically detecting *Babesia* species nucleic acid in a sample, said method comprising: (1) contacting a sample, said sample suspected of containing *Babesia* species nucleic acid, with at least two oligomers for amplifying a target region of a *Babesia* species target nucleic acid, wherein two of said at least two amplification oligomers are selected from the group consisting of: (a) a first amplification oligomer and a second amplification oligomer, wherein the first amplification oligomer comprises a first target-hybridizing sequence (i) that is from 15 to 33 contiguous nucleobases in length, is contained in SEQ ID NO:66 and contains SEQ ID NO:56 or SEQ ID NO:57, or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises/consists of SEQ ID NO:8 or 83; or (b) a first amplification oligomer and a second amplification oligomer, wherein the second amplification oligomer comprises a second target-hybridizing sequence that is from about 15 to about 33 contiguous nucleotides in length, and is (i) contained in SEQ ID NO:68 and contains SEQ ID NO:52, SEQ ID NO:53 SEQ ID NO:54, SEQ ID NO:55, or SEQ ID NO:85, or (ii) is contained in SEQ ID NO:67 and contains SEQ ID NO:45 or SEQ ID NO:69, or (iii) is contained in SEQ ID NO:70 and contains SEQ ID NO:46, SEQ ID NO:47, SEQ ID NO:48, SEQ ID NO:49, SEQ ID NO:50, or SEQ ID NO:51; or (iv) comprises or consists of SEQ ID NO:84; (2) performing an in vitro nucleic acid amplification reaction, wherein any *Babesia* target nucleic acid present in said sample is used as a template for generating an amplification product, wherein said amplification product has a length of from 180 to 220 contiguous nucleotides and contains SEQ ID NO:65 or the complement thereof; and (3) detecting the presence or absence of the amplification product, thereby indicating the presence or absence of *Babesia* species target nucleic acid in said sample.

In those embodiments in which the amplification product has a length of from 180 to 220 contiguous nucleotides and contains SEQ ID NO:65 or the complement thereof it is also contemplated that the amplification product has a length of from 180 to 210 contiguous nucleotides and contains SEQ ID NO:65 or the complement thereof. It is also contemplated that the amplification product has a length of from 180 to 200 contiguous nucleotides and contains SEQ ID NO:65 or the complement thereof. It is also contemplated that the amplification product has a length of from 180 to 190 contiguous nucleotides and contains SEQ ID NO:65 or the complement thereof. It is also contemplated that the amplification product has a length of from 190 to 220 contiguous nucleotides and contains SEQ ID NO:65 or the complement thereof. It is also contemplated that the amplification product has a length of from 200 to 220 contiguous nucleotides and contains SEQ ID NO:65 or the complement thereof. It is also contemplated that the amplification product has a length of from 210 to 220 contiguous nucleotides and contains SEQ ID NO:65 or the complement thereof.

Further combinations of first and second amplification oligomers therefore also include those in which the first amplification oligomer comprises a first target-hybridizing sequence that is from 15 to 33 contiguous nucleobases in length, is contained in SEQ ID NO:66 and contains SEQ ID NO:56; or comprises a first target-hybridizing sequence that is from 15 to 33 contiguous nucleobases in length, is contained in SEQ ID NO:66 and contains SEQ ID NO:57; or comprises a first target hybridizing sequence that is from 15 to 33 contiguous nucleotides in length, is contained in the sequence of SEQ ID NO:96 and contains SEQ ID NO:101; or comprises a first target-hybridizing sequence from 15 to 33 contiguous nucleotides in length, is contained in the sequence of SEQ ID NO:97 and contains SEQ ID NO:101; or comprises or consists of SEQ ID NO:8.

Further combinations of first and second amplification oligomers therefore also include those in which the second amplification oligomer comprises a second target-hybridizing sequence that is from about 15 to about 33 contiguous nucleotides in length and is contained in SEQ ID NO:68 and contains SEQ ID NO:52, or contains SEQ ID NO:53 or contains SEQ ID NO:54 or contains SEQ ID NO:55 or contains SEQ ID NO:85.

Further combinations of first and second amplification oligomers therefore also include those in which the second amplification oligomer comprises a second target-hybridizing sequence that is from about 15 to about 33 contiguous nucleotides in length and is contained in SEQ ID NO:67 and contains SEQ ID NO:45 or contains SEQ ID NO:69.

Further combinations of first and second amplification oligomers therefore also include those in which the second amplification oligomer comprises a second target-hybridizing sequence that is from about 15 to about 33 contiguous nucleotides in length and is contained in SEQ ID NO:70 and contains SEQ ID NO:46 or contains SEQ ID NO:47 or contains SEQ ID NO:48 or contains SEQ ID NO:49 or contains SEQ ID NO:50 or contains SEQ ID NO:51.

Further combinations of first and second amplification oligomers therefore also include those in which the second amplification oligomer comprises a second target-hybridizing sequence that is from about 15 to about 33 contiguous nucleotides in length and contains SEQ ID NO:84.

In some embodiments, combinations of certain first and second amplification oligomers are preferred.

One preferred combination is a first amplification oligomer comprising a first target-hybridizing sequence that is from 15 to 33 contiguous nucleobases in length, is contained in SEQ ID NO:66 and comprises SEQ ID NO:56 or SEQ ID NO:57 and a second amplification oligomer comprising a second target-hybridizing sequence that is contained in SEQ ID NO:67 and comprises SEQ ID NO:45. A more preferred combination is a first amplification oligomer comprising or consisting of the sequence set forth in SEQ ID NO:1 or comprising or consisting of the target-hybridizing sequence set forth in SEQ ID NO:2 and a second amplification oligomer comprising or consisting of the target-hybridizing sequence set forth in SEQ ID NO:27. According to this embodiment, these combinations of first and second amplification oligomers can be used in combination with a detection probe, suitably, a detection probe in which the target hybridising sequence comprises or consists of the sequence set forth in SEQ ID NO:38.

Another preferred combination is a first amplification oligomer comprising a first target-hybridizing sequence that is from 15 to 33 contiguous nucleobases in length, is contained in the sequence of SEQ ID NO:66 and comprises SEQ ID NO:56 and a second amplification oligomer comprising a second target-hybridizing sequence that is contained in SEQ ID NO:70 and comprises SEQ ID NO:49 or SEQ ID NO:50, or SEQ ID NO:51. A more preferred combination is a first amplification oligomer comprising or consisting of the sequence set forth in SEQ ID NO:3 or the target-hybridising sequence set forth in SEQ ID NO:4 and a second amplification oligomer comprising or consisting of the target-hybridising sequence set forth in SEQ ID NO:21. According to this embodiment, these combinations of first and second amplification oligomers can be used in combination with a detection probe, suitably, a detection probe in which the target hybridising sequence comprises or consists of the sequence set forth in SEQ ID NO:39.

Another preferred combination is a first amplification oligomer comprising a first target-hybridizing sequence that is from 15 to 33 contiguous nucleobases in length, is contained in the sequence of SEQ ID NO:96 and comprises SEQ ID NO:101 and a second amplification oligomer comprising a second target-hybridizing sequence that is contained in SEQ ID NO:68 and comprises SEQ ID NO:52, SEQ ID NO:53, SEQ ID NO:54, SEQ ID NO:55, or SEQ ID NO:85. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35,36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:96 and comprises SEQ ID NO:101 and a second amplification oligomer comprising a second target-hybridizing sequence that is contained in SEQ ID NO:70 and comprises SEQ ID NO:49 or SEQ ID NO:50, or SEQ ID NO:51. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35,36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:96 and comprises SEQ ID NO:101 and a second amplification oligomer comprising a second target-hybridizing sequence comprising or consisting of SEQ ID NO:84. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35,36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:97 and comprises SEQ ID NO:101 and a second amplification oligomer comprising a second target-hybridizing sequence that is contained in SEQ ID NO:68 and comprises SEQ ID NO:52, SEQ ID NO:53, SEQ ID NO:54, SEQ ID NO:55, or SEQ ID NO:85. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35,36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:97 and comprises SEQ ID NO:101 and a second amplification oligomer comprising a second target-hybridizing sequence that is contained in SEQ ID NO:70 and comprises SEQ ID NO:49 or SEQ ID NO:50, or SEQ ID NO:51. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35,36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:97 and comprises SEQ ID NO:101 and a second amplification oligomer comprising a second target-hybridizing sequence comprising or consisting of SEQ ID NO:84. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35,36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer in which the target-hybridizing sequence comprises or consists of SEQ ID NO:8 or SEQ ID NO:83 and a second amplification oligomer comprising a second target-hybridizing sequence that is contained in SEQ ID NO:70 and comprises SEQ ID NO:49 or SEQ ID NO:50, or SEQ ID NO:51. A more preferred combination is a first amplification oligomer comprising or consisting of the sequence set forth in SEQ ID NO:7 or SEQ ID NO:8 or SEQ ID NO:82 or SEQ ID NO:83 and a second amplification oligomer comprising or consisting of the sequence set forth in SEQ ID NO:21. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer in which the target-hybridizing sequence comprises or consists of SEQ ID NO:8 or SEQ ID NO:83 and a second amplification oligomer comprising a second target-hybridizing sequence that is contained in SEQ ID NO:70 and comprises SEQ ID NO:46 or SEQ ID NO:47 or SEQ ID NO:48 or SEQ ID NO:49 or SEQ ID NO:50 or SEQ ID NO:51. A more preferred combination is a first amplification oligomer comprising or consisting of the sequence set forth in SEQ ID NO:7 or SEQ ID NO:8 or SEQ ID NO:82 or SEQ ID NO:83 and a second amplification oligomer comprising or consisting of the sequence set forth in SEQ ID NO:34 or SEQ ID NO:84 or SEQ ID NO:86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:96 and comprises SEQ ID NO:101 and a second amplification oligomer comprising a second target-hybridizing sequence that is from about 15 to about 33 contiguous nucleotides in length, and is contained in SEQ ID NO:68 and comprises SEQ ID NO:85. A more preferred combination is a first amplification oligomer comprising or consisting of the sequence set forth in SEQ ID NO:7 or SEQ ID NO:8 or SEQ ID NO:82 or SEQ ID NO:83 and a second amplification oligomer comprising or consisting of the sequence set forth in SEQ ID NO:34 or SEQ ID NO:84 or SEQ ID NO:86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:97 and comprises SEQ ID NO:101 and a second amplification oligomer comprising a second target-hybridizing sequence that is from about 15 to about 33 contiguous nucleotides in length, and is contained in SEQ ID NO:68 and comprises SEQ ID NO:85. A more preferred combination is a first amplification oligomer comprising or consisting of the sequence set forth in SEQ ID NO:7 or SEQ ID NO:8 or SEQ ID NO:82 or SEQ ID NO:83 and a second amplification oligomer comprising or consisting of the sequence set forth in SEQ ID NO:34 or SEQ ID NO:84 or SEQ ID NO:86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Detection of the amplified products may be accomplished by a variety of methods to detect a signal specifically associated with the amplified target sequence. The nucleic acids may be associated with a surface that results in a physical change, such as a detectable electrical change Amplified nucleic acids may be detected by concentrating them in or on a matrix and detecting the nucleic acids or dyes associated with them (e.g. an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481). Directly or indirectly labeled probes that specifically associate with the amplified product provide a detectable signal that indicates the presence of the target nucleic acid in the sample.

Detection probes (where labelled) that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified sequences may be unlabeled and detected indirectly (e.g., by binding of another binding partner to a moiety on the probe) or may be labeled with a variety of detectable labels. In some embodiments of the method for diagnosing BV, such as in certain embodiments using transcription-mediated amplification (TMA), the detection probe is a linear chemiluminescently labeled probe such as, e.g., a linear acridinium ester (AE) labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174).

In embodiments that detect the amplified product near or at the end of the amplification step, a linear detection probe may be used to provide a signal to indicate hybridization of the probe to the amplified product. One example of such detection uses a luminescentally labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., US Patent Nos. 5, 118,801; 5,312,728; 5,925,517; 6,150,097; 6,849,412; 6,835,542; 6,534,274; and 6,361,945; and US Patent Application Pub. Nos. 20060068417A1 and 20060194240A1).

In certain embodiments comprising an amplification-based detection assay targeting *Babesia* sp., the method utilizes one or more detection probes that specifically hybridizes to a *Babesia* sp. amplification product. In particular variations, a *Babesia* sp.-specific detection probe oligomer comprises a target-hybridizing sequence that is from about 14 to about 40 nucleotides in length and is configured to specifically hybridize to a target sequence contained in SEQ ID NO:59, the RNA equivalent of SEQ ID NO:59, the complement of SEQ ID NO:59, the RNA equivalent of the complement of SEQ ID NO:59, SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence contains the sequence of SEQ ID NO:59 and includes at least the sequence of SEQ ID NO:37, 42, or 99.

Suitably, the detection probe target-hybridizing sequence is contained in the sequence of SEQ ID NO:65 and includes at least the sequence of SEQ ID NO:59, 94, or 99.

Suitably, the detection probe oligomer comprises a nucleotide sequence that is from 16 to 25 contiguous nucleotides in length and specifically hybridizes to SEQ ID NO:65, or the DNA equivalent thereof; or specifically hybridizes to the complement of SEQ ID NO:65, or the DNA equivalent thereof.

Suitably, the detection probe oligomer sequence further comprises a nucleotide sequence comprising or consisting of SEQ ID NO:59, 94, or 99.

Suitably, the detection probe target hybridising sequence consists of the sequence selected from the group consisting of: SEQ ID NOs:37, 38, 39, 40, 41, 42, 59, 60, 91, 92, 93, 94, 98 or 99.

Suitably, the detection probe oligomer further comprises a 2' methoxy modification on at least one nucleotide residue member of the nucleotide sequence.

In some embodiments of a method comprising the use of a nucleic-acid-base detection assay, a non-amplification-based assay is used to detect *Babesia* sp. In some such embodiments, the non-amplification-based assay is a hybridization assay comprising the hybridization of a specific detection probe to a target nucleic acid. Methods for conducting polynucleotide hybridization assays have been well developed in the art. Hybridization assay procedures and conditions will vary depending on the application and are selected in accordance with the general binding methods known, including those referred to in, e.g., Maniatis et al, Molecular Cloning: A Laboratory Manual (3rd ed. Cold Spring Harbor, N.Y., 2002), and Berger and Kimmel, Methods in Enzymology, Vol. 152, Guide to Molecular Cloning Techniques (Academic Press, Inc., San Diego, Calif., 1987). Generally, the probe and sample are mixed under conditions that will permit specific nucleic acid hybridization, and specific hybridization of the probe to its respective target is then detected. Nucleic acid hybridization is adaptable to a variety of assay formats. One suitable format is the sandwich assay format, which is particularly adaptable to hybridization under non-denaturing conditions. A primary component of a sandwich-type assay is a solid support, which has adsorbed to it or covalently coupled to it immobilized nucleic acid probe that is unlabeled and complementary to one portion of the DNA sequence. Target nucleic acid is hybridized to the immobilized probe, and a second, labeled detection probe—which is complementary to a second and different region of the same DNA strand to which the immobilized, unlabeled nucleic acid probe is hybridized—is hybridized to the [target nucleic acid]: [immobilized probe] duplex to detect the target nucleic acid. Another exemplary format utilizes electrochemical detection of target nucleic acids hybridized to unlabeled detection probes immobilized on a suitable electrode surface as a signal transducer. See, e.g., Drummond et al., Nat. Biotechnol. 21: 1192, 2003; Gooding, Electroanalysis 14: 1149, 2002; Wang, Anal. Chim Acta 469:63, 2002; Cagnin et al., Sensors 9:3122, 2009; Katz and Willner, Electroanalysis 15:913, 2003; Daniels and Pourmand, Electroanalysis 19: 1239, 2007.

In certain embodiments comprising a hybridization assay, a detection probe is utilized for the detection of a *Babesia* sp. In such embodiments, a detection probe oligomer for detecting *Babesia* sp. comprises a target-hybridizing sequence that is from about 14 to about 40 nucleotides in length and is configured to specifically hybridize to a target sequence contained in SEQ ID NO:59, the RNA equivalent of SEQ ID NO:59, the complement of SEQ ID NO:59, the RNA equivalent of the complement of SEQ ID NO:59, SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence is contained in the sequence of SEQ ID NO:59 and includes at least the sequence of SEQ ID NO:42, 92, 94, or 99.

Suitably, the detection probe target-hybridizing sequence contains the sequence of SEQ ID NO:59 and includes at least the sequence of SEQ ID NO:37, 42, or 99.

Suitably, the detection probe target-hybridizing sequence is contained in the sequence of SEQ ID NO:65 and includes at least the sequence of SEQ ID NO:59, 94 or 99.

Suitably, the detection probe oligomer comprises a nucleotide sequence that is from 16 to 25 contiguous nucleotides in length and specifically hybridizes to SEQ ID NO:65, or the DNA equivalent thereof; or specifically hybridizes to the complement of SEQ ID NO:65, or the DNA equivalent thereof.

Suitably, the detection probe oligomer sequence further comprises a nucleotide sequence containing SEQ ID NO:59, 94, or 99.

Suitably, the detection probe target hybridising sequence consists of the sequence selected from the group consisting of: SEQ ID NO:37, 38, 39, 40, 41, 42, 59, 60, 91, 92, 93, 94, 98 or 99.

Suitably, the detection probe oligomer further comprises a 2' methoxy modification on at least one nucleotide residue member of the nucleotide sequence.

In some embodiments, a non-amplification-based assay for detection of *Babesia* sp. is a cleavage-based assay, in which a probe oligonucleotide containing a non-target-hybridizing flap region is cleaved in an overlap-dependent manner by a flap endonuclease to release a cleavage product that is then detected. Exemplary cleavage-based assay reagents are described in, e.g., Lyamichev et al. (Nat. Biotechnol. 17:292-296, 1999), Ryan et al. (Mol. Diagn. 4: 135-144, 1999), and Allawi et al. (J. Clin. Microbiol. 44:3443-3447, 2006).

Appropriate conditions for flap endonuclease reactions are either known or can be readily determined using methods known in the art (see, e.g., Kaiser et al, J. Biol. Chem. 274:2138-721394, 1999). Exemplary flap endonucleases that may be used in the method include *Thermus aquaticus* DNA polymerase I, *Thermus thermophilus* DNA polymerase I, mammalian FEN-1, *Archaeoglobus fulgidus* FEN-1, Methanococcus jannaschii FEN-1, *Pyrococcus* fiiriosus FEN-1, *Methanobacterium* thermoautotrophicum FEN-1, *Thermus thermophilus* FEN-1, CLEAVASE® (Hologic, Inc., Madison, Wis.), *S. cerevisiae* RTH1, *S. cerevisiae* RAD27, *Schizosaccharomyces pombe* rad2, bacteriophage T5 5'-3' exonuclease, *Pyrococcus horikoshii* FEN-1, human endonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of flap endonucleases can be found in, for example, Lyamichev et al., Science 260:778-783, 1993; Eis et al, Nat. Biotechnol. 19:673-676, 2001; Shen et al, Trends in Bio. Sci. 23: 171-173, 1998; Kaiser et al, J. Biol. Chem. 274:21387-21394, 1999; Ma et al, J. Biol. Chem. 275:24693-24700, 2000; Allawi et al, J. Mol. Biol. 328:537-554, 2003; Sharma et al, J. Biol. Chem. 278:23487-23496, 2003; and Feng et al, Nat. Struct. Mol. Biol. 11:450-456, 2004.

In certain variations, a cleavage-based assay detects an RNA target nucleic acid of *Babesia* sp., and the cleavage-based assay utilizes a flap endonuclease that is capable of cleaving and RNA:DNA linear duplex structure. In some alternative embodiments, a cleavage-based assay detects a DNA target nucleic acid of *Babesia* sp., and the cleavage-based assay utilizes a flap endonuclease that is capable of cleaving and DNA:DNA linear duplex structure. Exemplary flap endonucleases capable of cleaving RNA:DNA duplexes include polymerase-deficient 5' nucleases of the genus *Thermus* as well as certain CLEAVASE® enzymes (Hologic, Inc., Madison, Wis.) such as, for example, CLEAVASE® BN (BstX-Notl deletion of Taq polymerase, see U.S. Pat. No. 5,614,402), CLEAVASE® II ("AG" mutant of full length Taq polymerase, see U.S. Pat. No. 5,614,402), CLEAVASE® VII (synthesis-deficient mutation of full length *Thermus thermophilus* polymerase), CLEAVASE® IX (polymerase deficient mutant of the Tth DNA polymerase), and CLEAVASE® XII (polymerase deficient chimeric polymerase constructed from fragments of taq DNA polymerase and Tth DNA polymerase). Exemplary flap endonucleases capable of cleaving DNA:DNA duplexes include the flap endonucleases indicated above, as well as CLEAVASE® 2.0 (*Archaeoglobus fulgidus* FEN-1), CLEAVASE® 2.1 (*Archaeoglobus fulgidus* FEN-1 with 6 histidines on the C-terminus), CLEAVASE® 3.0 (*Archaeoglobus* veneficus FEN-1), and CLEAVASE® 3.1 (*Archaeoglobus* veneficus FEN-1 with 6 histidines on the C-terminus).

In some embodiments, a cleavage-based assay detects an RNA target nucleic acid of *Babesia* sp., and the assay includes a step for synthesizing a DNA complement of an RNA target region, which cDNA strand is then hybridized to overlapping first and second probe oligonucleotides to form a linear duplex cleavage structure for cleavage by the flap endonuclease. Reaction conditions for synthesizing cDNA from an RNA template, using an RNA-dependent DNA polymerase (reverse transcriptase), are well-known in the art.

In certain embodiments utilizing a nucleic-acid-based detection assay, the method further includes purifying the *Babesia* sp. target nucleic acid from other components in the sample. Such purification may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Babesia* sp. nucleic acid and other sample components.

In some embodiments, a target nucleic acid of *Babesia* sp. is separated from other sample components by hybridizing the target nucleic acid to a capture probe oligomer. The capture probe oligomer comprises a target-hybridizing sequence configured to specifically or non-specifically hybridize to a target nucleic acid so as to form a [target nucleic acid]: [capture probe] complex that is separated from other sample components. Capture probes comprising target-hybridizing sequences suitable for non-specific capture of target nucleic acids are described in, e.g., WO 2008/016988. In some specific variations comprising target-hybridizing sequence(s) configured to specifically hybridize to a *Babesia* sp. target nucleic acid, a *Babesia*-specific capture probe comprises a target-hybridizing sequence that (i) is from about 15 to about 21 contiguous nucleotides contained in the sequence of SEQ ID NO:78, or (ii) is about 21 to 30 contiguous nucleotides comprising the sequence of SEQ ID NO:78; or (iii) the sequence consists of SEQ ID NO:44. In a preferred variation, the capture probe binds the [target nucleic acid]: [capture probe] complex to an immobilized probe to form a [target nucleic acid]: [capture probe] [immobilized probe] complex that is separated from the sample and, optionally, washed to remove non-target sample components (see, e.g., U.S. Pat. Nos. 6,110,678; 6,280,952; and 6,534,273). In such variations, the capture probe oligomer further comprises a sequence or moiety that binds the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to target nucleic acid but that specifically hybridizes to a sequence on the immobilized probe, thereby serving as the moiety allowing the target nucleic acid to be separated from other sample components, such as previously described in, e.g., U.S. Pat. No. 6,110,678. Any sequence may be used in a tail region, which is generally about 5 to 50 nt long, and preferred embodiments include a substantially homopolymeric tail of about 10 to 40 nt (e.g., A10 to A40), more preferably about 14 to 33 nt (e.g., A14 to A30 or T3A14 to T3A30), that bind to a complementary immobilized sequence (e.g., poly-T) attached to a solid support, e.g., a matrix or particle. In some such embodiments comprising target-hybridizing sequence(s) configured to specifically hybridize to *Babesia* sp. target nucleic acid, a *Babesia*-specific capture probe comprises or consists of a the nucleotide sequence of SEQ ID NO:43.

Target capture typically occurs in a solution phase mixture that contains one or more capture probe oligomers that hybridize to the target nucleic acid under hybridizing conditions, usually at a temperature higher than the Tm of the [tail sequence] [immobilized probe sequence] duplex. For embodiments comprising a capture probe tail, the [target nucleic acid]: [capture probe] complex is captured by adjusting the hybridization conditions so that the capture probe tail hybridizes to the immobilized probe, and the entire complex on the solid support is then separated from other sample components. The support with the attached [immobilized probe]: [capture probe]: [target nucleic acid] may be washed one or more times to further remove other sample components. Preferred embodiments use a particulate solid support, such as paramagnetic beads, so that particles with the attached [target nucleic acid]: [capture probe]: [immobilized probe] complex may be suspended in a washing solution and retrieved from the washing solution, preferably by using magnetic attraction. In embodiments of the method comprising the use of an amplification-based detection assay, to limit the number of handling steps, a target nucleic acid may be amplified by simply mixing the target nucleic acid in the complex on the support with amplification oligomers and proceeding with amplification steps.

In some embodiments of a method for diagnosing Babesiosis, where detection of *Babesia* sp. indicates Babesiosis in a subject, the method further includes treating Babesiosis in the subject. Treatment regimens for Babesiosis are generally known in the art and include, for example, administration of anti-parasitic medications or red blood cell exchange transfusion as an adjunct therapy. In certain variations, the subject has not been previously diagnosed with Babesiosis. In other embodiments, the subject has been previously diagnosed with Babesiosis and is undergoing treatment for Babesiosis at the time a diagnostic method of the present disclosure is performed. Such variations are particularly useful for monitoring treatment of Babesiosis in a subject. For example, if the method indicates that Babesiosis is still present in the subject, then the subject may continue treatment. In some embodiments, the same treatment regime (i.e., the same treatment that the subject is undergoing at the time the present diagnostic method is performed) is re-administered to the subject. Alternatively, the continued presence of Babesiosis in the subject undergoing treatment may indicate that a change in the ongoing treatment is needed, and a different treatment regime (e.g., a different medication, or an increased dosage and/or frequency of a drug) is administered to the subject.

In accordance with the present disclosure, detecting the presence or absence of *Babesia* sp. may be performed separately (e.g., in a separate reaction vessel), or performed together with another assay as a multiplex reaction system. Accordingly, in some embodiments, a method as described herein (e.g., a method for diagnosing Babesiosis) utilizes a multiplex reaction, where the reaction mix contains reagents for assaying multiple (e.g., at least two, three, four, or more) different target sequences in parallel. In these cases, a reaction mix may contain multiple different target-specific oligonucleotides for performing the detection assay. For example, in a method utilizing an amplification-based detection assay, a multiplex reaction may contain multiple sets (e.g., multiple pairs) of amplification oligomers (for example, multiple pairs of PCR primers or multiple pairs of TMA amplification oligomers (e.g., for TMA, multiple pairs of promoter primer and non-promoter primer, or multiple pairs of promoter provider and non-promoter primer)). In other embodiments utilizing a cleavage-based detection assay, a multiplex reaction may contain multiple probe oligonucleotides having different flaps, multiple different overlapping probe oligonucleotides, and multiple different FRET cassettes for detecting the different flaps, once they are cleaved.

The oligomer combination described herein may be in the form of a reaction mixture or a kit comprising the oligomers. The reaction mixture or kit may further include a number of optional components such as, for example, capture probe nucleic acids or arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which a *Babesia* sp. target nucleic acid may or may not be present. A kit comprising an oligomer combination for amplification of *Babesia* sp. may also include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). For an oligomer combination (e.g., reaction mixture or kit) that includes a detection probe together with an amplification oligomer combination targeting a common target nucleic acid, selection of amplification oligomers and detection probe oligomers are linked by a common target region (i.e., the combination will include a probe that binds to a sequence amplifiable by the amplification oligomer combination).

The compositions, methods, reaction mixtures, systems, kits and the like for detection of *Babesia* nucleic acids are further illustrated by the following non-limiting examples.

EXAMPLES

"Sample Transport Solution" generally refers to a solution formulated to preserve a sample, and in some instances formulated to at least partially lyse one or more cell types in a sample. One exemplary sample transport solution comprises 15 mM sodium phosphate monobasic, 15 mM sodium phosphate dibasic, 1 mM EDTA, 1 mM EGTA, and 110 mM lithium lauryl sulfate (LLS), at pH 6.7. Another exemplary sample transport solution comprises an aqueous solution of 100 mM TRIS, 30 mM magnesium chloride, and 6% (v/v) LLS, at pH 7.5. A further exemplary sample transport solution comprises an aqueous solution of 14 mM sodium bicarbonate, 250 mM ammonium chloride, 5% (v/v) LLS, and 0.1 mM EDTA, at a pH of 7.4. Other formulations of sample transport solutions may function equally well.

"Target Capture Reagent" generally refers to a solution containing a number of components that facilitate capture of a nucleic acid from a solution. One exemplary Target Capture Reagent comprises 250 mM HEPES, 310 mM lithium hydroxide, 1.88 M lithium chloride, 100 mM EDTA, at pH 6.4, and 250 μg/ml of magnetic particles (1 micron SERA-MAG/\TM MG-CM particles, GE Healthcare Lifesciences) with $dT_{14}$ oligomers covalently bound thereto. Another exemplary Target Capture Reagent comprises 790 mM HEPES, 453 mM lithium hydroxide, 10% w/v LLS, 230 mM Succinic Acid, 0.03% w/v Foam Ban MS-575, and 0.0125% w/v of magnetic particles (1 micron SERA-MAG/\TM MG-CM particles, GE Healthcare Lifesciences) with $dT_{14}$ oligomers covalently bound. Other formulations of Target Capture Reagent may function equally as well.

"Wash Solution" generally refers to a solution containing 10 mM HEPES, 150 mM sodium chloride, 6.5 mM sodium hydroxide, 1 mM EDTA, 0.3% (v/v) ethanol, 0.02% (w/v) methyl paraben, 0.01% (w/v) propyl paraben, and 0.1% (w/v) sodium lauryl sulfate, at pH 7.5.

"Probe Reagent" generally refers to a solution containing one or more labeled detection probes. One exemplary Probe Reagent is a solution made up of from about 75 to about 100 mM lithium succinate, 2% (w/v) LLS, 15 mM mercaptoethanesulfonate, 1.2 M lithium chloride, 20 mM EDTA, and 3% (v/v) ethanol, at pH 4.7. Another exemplary Probe Reagent is a solution made up of from about 75 to about 100 mM succinic acid, 3.5% (w/v) LLS, 75 mM lithium hydroxide, 15 mM aldrithiol-2, 1.0 M lithium chloride, 1 mM EDTA, and 3.0% (v/v) ethanol, at pH 4.1-4.3. Other formulations may perform equally as well.

"Amplification Reagent" generally refers to a concentrated mixture of reaction components to facilitate amplification reactions. An Amplification Reagent will comprise a number of different reagents at various concentrations depending on factors such as for example amplification type (PCR, TMA, etc.), target nucleic acids (GC content), and the like. One exemplary Amplification Reagent comprises 47.6 mM Na-HEPES, 12.5 mM N-acetyl-L-cysteine, 2.5% TRITON™ X-100, 54.8 mM KCl, 23 mM MgCl2, 3 mM NaOH, 0.35 mM of each dNTP (dATP, dCTP, dGTP, dTTP), 7.06 mM rATP, 1.35 mM rCTP, 1.35 mM UTP, 8.85 mM rGTP, 0.26 mM Na2EDTA, 5% v/v glycerol, 2.9% trehalose, 0.225% ethanol, 0.075% methylparaben, 0.015% propylparaben, and 0.002% Phenol Red, at pH 7.5-7.6. Another exemplary Amplification Reagent comprises 19.1 mM Trizma Base, 7.5 mM Trizma Hydrochloride, 23.3 mM KCl, 21.5 mM MgCl2, 1 mM of each dNTP (dATP, dCTP, dGTP, dTTP), 6.5 mM rATP, 4.0 mM rCTP, 4.0 mM UTP, 6.5 mM rGTP, 3.33% v/v glycerol, 0.05 mM Zinc Acetate, 6 ppm Pro Clin 300 preservative, at pH 8.25-8.45. Other formulations of amplification reagent may function equally well. Primers may be added to the amplification reagent or added to amplification reactions separate from the amplification reagent. Enzymes in an amplification reagent can include one or more of Moloney Murine Leukemia Virus Reverse Transcriptase (MMLV-RT) and bacteriophage T7 RNA polymerase for which units are functionally defined as: 1 U of MMLV-RT incorporates 1 nmol of dTTP in 10 mM at 37C using 200-400 micromolar oligo dT-primed poly(A) as template, and 1 U of T7 RNA polymerase incorporates 1 nmol of ATP into RNA in 1 hr at 37C using a DNA template containing a T7 promoter.

"Hybridization Reagent" generally refers to a solution made up of reagents having concentrations in the range of about: 75-100 mM succinic acid, 2%-3.5% (w/v) LLS, 75-100 mM lithium hydroxide, 14-16 mM aldrithiol-2, 1.0-1.2 M lithium chloride, 20-1000 mM EDTA, and 2.0-4.0% (v/v) ethanol, at pH 4-5 Other formulations for a Hybridization Reagent may function equally well.

"Selection Reagent" generally refers to a solution containing 600 mM boric acid, 182.5 mM sodium hydroxide, 1% (v/v) octoxynol (TRITON® X-100), at pH 8.5.

"Detection Reagents" include "Detect Reagent I," which generally refers to a solution containing 1 mM nitric acid and 32 mM hydrogen peroxide, and "Detect Reagent II," which generally refers to a solution of 1.5 M sodium hydroxide.

EXAMPLE 1: Initial Oligo Screening

Objective:

Non-T7 and T7 primers and probes were screened using the manual Procleix Enhanced Semi-automated System (eSAS) for transcription mediated amplification (TMA) and hybridization protection assays (HPA) in order to identify primer-probe combinations with the ability to amplify and specifically detect specifically species of *Babesia*—including *B. microti, B. divergens, B. duncani* and *B. venatorum*. The assay does not discriminate between these *Babesia* species. Reactive results indicate that a sample is positive for *Babesia*.

Materials Methods:

Initial primer screening was performed using TMA on the manual Procleix system using in-vitro transcripts (IVT) for *Babesia microti* (SEQ ID NO:61), *Babesia divergens* (SEQ ID NO:62), and *Babesia duncani* (SEQ ID NO:63). Reactions for this testing began at the amplification step. An assay rack consisted of 10 rows of Ten-tube units (TTUs). 75 microliters of Amplification Reagent and 10 picomoles each of one T7 promoter provider oligonucleotide from Tables 1-3 and one non-T7 primer oligonucleotide from Tables 1-3 were added to the appropriate tubes on the rack such that each combination of amplification oligomers were tested with two replicates each of *Plasmodium falciparum* IVT (SEQ ID NO:64) at 10,000 copies per reaction and *B. divergens, B. duncani*, and *B. microti* IVT at 15 copies per reaction. *P. falciparum* was included in initial screening as a cross reactivity specimen due to the conserved regions between *Babesia* and *Plasmodium*. It is necessary to determine that amplification and detection systems are specific to *Babesia*. To achieve the target copies per reaction, 10 μL of *P. falciparum* IVT at 1e6 c/mL diluted in a buffer was spiked into the appropriate tubes, and 10 μL of *Babesia* species IVT at 1,500 c/mL diluted in a buffer were spiked into the appropriate tubes. Various combinations of Primers were tested. This set-up allows for 10 primer combinations to be tested per rack. Once the primer combinations and IVTs were spiked, 200 μL of oil was added to each tube and then the rack was covered with sealing cards and vortexed for a minimum of 20 seconds.

The rack was then incubated in a water bath at 60±1° C. for 10±1 minutes followed by incubation in a 41.5±1° C. water bath for between 9 and 20 minutes. While the rack remained in the water bath, the sealing cards were removed and 25 μL of commercially available Procleix Ultrio Plus enzyme reagent (Grifols Diagnostics Solutions, Inc.) was added to each reaction tube and then covered again with sealing cards. The rack was gently shaken to mix and then covered again with sealing cards and incubated for another 60±5 minutes in the 41.5±1° C. water bath.

After incubation completed, the rack was transferred to the hybridization protection assay (HPA) area where the sealing cards were removed. 100 μL of Probe reagent consisting of 1 acridinium-ester (AE) labeled probe (Tables 1-3) added at a total desired concentration of 5e6 Relative Light Units (RLU) per reaction to a Hybridization Reagent. Probe reagent was then added to the appropriate reaction tubes. The tubes were covered with sealing cards and the rack was vortexed for a minimum of 20 seconds after which the rack was incubated in a water bath at 61±2° C. for 15±1 minutes.

The rack was removed from the water bath, the sealing cards removed, and 250 μL of commercially available Procleix Ultrio Plus selection reagent (Grifols Diagnostics Solutions, Inc.) was added to each tube. The tubes were covered with sealing cards and vortexed for a minimum of 20 seconds and then returned to the 61±2° C. water bath and incubated for 10±1 minutes. After incubation the rack was allowed to cool in a 23±4° C. water bath for a minimum of 10 minutes.

For detection the TTUs are removed from the rack and loaded on to the automated Leader instrument for subsequent light off using commercially available Procleix Auto Detect 1 and 2 reagents (Grifols Diagnostics Solutions, Inc.) and the results were exported for analysis of the signal in Relative Light Units (RLU).

Primers screened in Group 1a and Group 1b (Table 1) were each of SEQ ID NO:3 and SEQ ID NO:5 promoter provider oligomers paired with each of SEQ ID NOs:12 to 16, 18 and 19 to 21 using both detection probe SEQ ID NO:37 and 39. Each rack used system SEQ ID NO:1, 11 and 37 as a control.

TABLE 1

Primers screened in Group 1a and Group 1b.

| SEQ ID NO | Sequence 5'-3' |
|---|---|
| 1 | aatttaatacgactcactatagggagattcacctctga cagttaaatacgaa |
| 3 | aatttaatacgactcactatagggagaacagttaaata cgaatgcccccaa |
| 5 | aatttaatacgactcactatagggagattcacctctga cagttaaatac |
| 12 | actacagcatggaataatga |
| 11 | cttgaatactacagcatgga |
| 13 | cttgaatactacagcatggaataa |
| 14 | acttcagcatggaataatga |
| 15 | cttgaatacttcagcatgga |
| 16 | actncagcatggaataatga (n is inosine in this example) |
| 18 | cttgaatactncagcatgga (n is inosine in this example) |
| 20 | actttgagaaaactagagtg |
| 21 | agaaaactagagtgtttcaa |
| 39 | aguaaugguuaauaggagca |
| 37 | ugaaguaggacuuugguucu |

Primers Screened in Group 2 (Table 2) were SEQ ID NO:3 promoter provider paired with each of SEQ ID NOs: 22-31, 75 and 76 primers using SEQ ID NO:39 detection probe. Each rack used system SEQ ID NO:3, SEQ ID NO:21 and SEQ ID NO:39 as a control.

TABLE 2

Primers screened in Group 2.

| SEQ ID NO: | Sequence 5'-3' |
|---|---|
| 3 | aatttaatacgactcactatagggagaa cagttaaatacgaatgcccccaa |
| 21 | agaaaactagagtgtttcaa |
| 24 | ggttctattttgttggtt |

TABLE 2-continued

| Primers screened in Group 2. | |
|---|---|
| SEQ ID NO: | Sequence 5'-3' |
| 25 | tggttctattttgttgg |
| 23 | aggactttggttctattttg |
| 75 | gaagtaggactttggttctattt |
| 76 | atgaagtaggactttggttct |
| 22 | ataatgaagtaggactttgg |
| 26 | ggaataatgaagtaggacttt |
| 27 | atggaataatgaagtaggac |
| 28 | atggaataatgaagtagg |
| 29 | gcatggaataatgaagtag |
| 30 | tacagcatggaataatgaag |
| 31 | tactacagcatggaataatg |
| 39 | aguaaugguuaauaggagca |

Primers screened in Group 3 (Table 3) were SEQ ID NO:1 promoter provider paired with each of SEQ ID NO:21, 27 and 29 primers and SEQ ID NO:38, 40 and 41 detection probes; SEQ ID NO:3 promoter provider paired with each of SEQ ID NO:21, 27 and 29 primers and SEQ ID NO:38 and 40 detection probes; and each of SEQ ID NO:3, 7 and 9 promoter provider paired with SEQ ID NO:21 primer and SEQ ID NO:39 detection probe.

TABLE 3

| Primers screened in Group 3. | |
|---|---|
| SEQ ID NO: | Sequence 5'-3' |
| 3 | aatttaatacgactcactatagggagaacagttaaatacgaatgcccccaa |

TABLE 3-continued

| Primers screened in Group 3. | |
|---|---|
| SEQ ID NO: | Sequence 5'-3' |
| 1 | aatttaatacgactcactatagggagattcacctctgacagttaaatacgaa |
| 7 | aatttaatacgactcactatagggagagctttcgcagtagttcgtctttaacaaatc |
| 9 | aatttaatacgactcactatagggagactttcgcagtagttcgtctttaac |
| 21 | agaaaactagagtgtttcaa |
| 27 | atggaataatgaagtaggac |
| 29 | gcatggaataatgaagtag |
| 39 | aguaaugguuaauaggagca |
| 38 | uaaugguuaauaggagcaguug |
| 40 | ggacuuugguucuauuuuguugg |
| 41 | aaugguuaauaggagcaguuggggg |

Results:

Ideal candidates from screening were expected to be reactive for *Babesia* species IVTs (*B. microti, B. divergens* and *B. duncani*) with analyte signals consistently at 1,000,000 RLU or higher for all replicates and negative for *P. falciparum* IVT and negative samples with analyte signals below 10,000 RLU. Some candidates with RLUs near 1,000,000 RLU for *Babesia* and below 30,000 RLU for *P. falciparum* and negatives were also given consideration.

For the primers and detection probes screened in Group 1a, not all primer-probe combinations consistently amplified and detected all species and some combinations resulted in high analyte signals for negative specimens (*P. falciparum* and Negative). Analyte RLU results for this group are listed in Table 4. Preferred candidates in this group were SEQ ID NO:3 promoter provider paired with SEQ ID NO:13, 20 or 21 primers and using SEQ ID NO:37 detection probe; and SEQ ID NO:3 promoter provider paired with SEQ ID NO:21 primer and SEQ ID NO:39 detection probe.

TABLE 4

| Analyte RLU Results for Group 1a. | | | | | | | |
|---|---|---|---|---|---|---|---|
| | | SEQ ID NO: 1 | | SEQ ID NO: 3 | | | |
| | | SEQ ID NO: 11 | | SEQ ID NO: 12 | | SEQ ID NO: 11 | |
| | | A | B | C | D | E | F |
| 10 | SEQ ID | 1,362 | 1,558 | 7,937 | 4,149 | 1,858 | 2,602 |
| 9 | NO: 39 | 1,751 | 1,944 | 217,421 | 2,083,520 | 624,278 | 1,234,110 |
| 8 | | 1,868,814 | 2,073,045 | 1,910,998 | 2,237,157 | 1,158,006 | 2,142,969 |
| 7 | | 2,296,815 | 2,273,471 | 2,348,718 | 2,365,590 | 2,259,692 | 2,374,484 |
| 6 | | 5,122 | 3,273 | 4,390 | 5,389 | 4,890 | 3,165 |
| 5 | SEQ ID | 15,427 | 2,286 | 13,870 | 6,363 | 123,550 | 4,161 |
| 4 | NO: 37 | 8,560 | 739,538 | 1,276,471 | 1,699,429 | 1,883,483 | 1,948,712 |
| 3 | | 1,915,070 | 1,982,035 | 2,030,041 | 2,073,715 | 1,847,501 | 2,010,877 |
| 2 | | 1,556,779 | 2,027,292 | 2,080,918 | 2,033,082 | 1,935,354 | 2,117,207 |
| 1 | | 2,750 | 3,797 | 2,020 | 160,345 | 4,308 | 10,144 |

TABLE 4-continued

Analyte RLU Results for Group 1a.

| | | SEQ ID NO: 3 | | | | |
|---|---|---|---|---|---|---|
| | | SEQ ID NO: 13 | | SEQ ID NO: 14 | | |
| | | G | H | I | J | |
| 10 | SEQ ID | 2,379 | 1,923 | 3,206 | 3,223 | P. fal 10K c/rxn |
| 9 | NO: 39 | 1,512,725 | 1,924,925 | 2,028,160 | 1,717,151 | B. div IVT 15 c/rxn |
| 8 | | 1,262,860 | 2,023,796 | 957,114 | 180,559 | B. dun IVT 15 c/rxn |
| 7 | | 2,310,437 | 2,287,714 | 2,363,103 | 2,306,377 | B. mic IVT 15 c/rxn |
| 6 | | 3,087 | 4,362 | 3,815 | 2,678 | Neg |
| 5 | SEQ ID | 5,645 | 2,157 | 21,188 | 10,899 | P. fal 10K c/rxn |
| 4 | NO: 37 | 1,753,900 | 1,907,723 | 1,838,478 | 1,913,729 | B. div IVT 15 c/rxn |
| 3 | | 1,929,009 | 1,972,774 | 2,050,677 | 1,981,200 | B. dun IVT 15 c/rxn |
| 2 | | 2,092,557 | 2,077,799 | 1,985,182 | 1,993,369 | B. mic IVT 15 c/rxn |
| 1 | | 1,727 | 2,368 | 2,807 | 5,288 | Neg |

| | | SEQ ID NO: 3 | | | | | |
|---|---|---|---|---|---|---|---|
| | | SEQ ID NO: 15 | | SEQ ID NO: 16 | | SEQ ID NO: 18 | |
| | | A | B | C | D | E | F |
| 10 | SEQ ID | 3,873 | 2,436 | 5,785 | 2,743 | 2,406 | 1,968 |
| 9 | NO: 39 | 1,918,232 | 1,880,797 | 1,368,977 | 2,094,325 | 1,486,108 | 2,119,826 |
| 8 | | 1,602,380 | 1,776,094 | 2,135,880 | 2,225,590 | 2,031,084 | 2,095,064 |
| 7 | | 375,283 | 981,890 | 2,375,662 | 2,447,002 | 2,298,733 | 2,218,629 |
| 6 | | 5,902 | 6,937 | 7,033 | 7,979 | 2,758 | 3,564 |
| 5 | SEQ ID | 7,609 | 150,048 | 314,165 | 25,323 | 1,726,513 | 1,674 |
| 4 | NO: 37 | 1,942,612 | 1,891,974 | 1,684,635 | 1,968,192 | 1,669,451 | 1,881,606 |
| 3 | | 1,966,629 | 1,993,188 | 2,063,195 | 2,071,412 | 1,901,864 | 1,960,251 |
| 2 | | 829,468 | 1,477,651 | 2,146,350 | 2,147,242 | 2,049,500 | 2,063,691 |
| 1 | | 1,553 | 4,723 | 190,368 | 12,971 | 1,949 | 1,627 |

| | | SEQ ID NO: 3 | | | | |
|---|---|---|---|---|---|---|
| | | SEQ ID NO: 20 | | SEQ ID NO: 21 | | |
| | | G | H | I | J | |
| 10 | SEQ ID | 1,535 | 2,439 | 2,493 | 2,249 | P. fal 10K c/rxn |
| 9 | NO: 39 | 1,912,598 | 882,449 | 1,936,565 | 2,170,010 | B. div IVT 15 c/rxn |
| 8 | | 1,893,023 | 1,800,511 | 2,240,797 | 2,087,446 | B. dun IVT 15 c/rxn |
| 7 | | 2,463,996 | 2,234,843 | 2,323,282 | 2,352,415 | B. mic IVT 15 c/rxn |
| 6 | | 2,246 | 1,866 | 2,602 | 1,792 | Neg |
| 5 | SEQ ID | 1,777 | 1,730 | 1,460 | 5,274 | P. fal 10K c/rxn |
| 4 | NO: 37 | 1,842,523 | 1,892,595 | 1,944,571 | 1,882,381 | B. div IVT 15 c/rxn |
| 3 | | 1,996,707 | 1,995,486 | 2,032,943 | 1,995,159 | B. dun IVT 15 c/rxn |
| 2 | | 2,057,722 | 2,091,173 | 2,110,461 | 2,140,647 | B. mic IVT 15 c/rxn |
| 1 | | 7,879 | 1,642 | 1,779 | 1,602 | Neg |

For the primers and detection probes screened in Group 1b, not all primer-probe combinations consistently amplified and detected all species and some combinations resulted in high analyte signals for *P. falciparum*. Analyte RLU results for this group are listed in Table 5. Preferred candidates in this group were SEQ ID NO:5 promoter provider paired with SEQ ID NO:11 or 13 primers and using the SEQ ID NO:37 detection probe.

TABLE 5

Analyte RLU Results for Group 1b.

| | | SEQ ID NO: 1 | | SEQ ID NO: 5 | | | |
|---|---|---|---|---|---|---|---|
| | | SEQ ID NO: 11 | | SEQ ID NO: 12 | | SEQ ID NO: 11 | |
| | | A | B | C | D | E | F |
| 10 | SEQ ID | 2,370 | 2,021 | 491 | 561 | 1,219 | 1,549 |
| 9 | NO: 39 | 2,606,527 | 2,273,506 | 1,343 | 180,755 | 668,964 | 645,097 |
| 8 | | 2,329,021 | 2,341,992 | 93,675 | 141,525 | 661,755 | 230,617 |
| 7 | | 2,586,212 | 2,656,633 | 2,513,992 | 2,519,282 | 2,398,111 | 2,468,394 |
| 6 | | 2,786 | 2,875 | 946 | 546 | 1,278 | 990 |

TABLE 5-continued

Analyte RLU Results for Group 1b.

| | | | | | | | |
|---|---|---|---|---|---|---|---|
| 5 | SEQ ID | 1,086 | 1,296 | 994 | 848 | 1,488 | 805 |
| 4 | NO: 37 | 1,862,765 | 1,798,372 | 392,887 | 965 | 1,378,157 | 1,340,279 |
| 3 | | 1,948,808 | 1,873,185 | 609,730 | 1,553,691 | 1,684,907 | 1,618,765 |
| 2 | | 2,019,896 | 1,956,929 | 1,610,113 | 1,432,157 | 1,866,395 | 1,912,090 |
| 1 | | 1,670 | 878 | 965 | 2,036 | 772 | 1,582 |

| | | SEQ ID NO: 5 | | | | |
|---|---|---|---|---|---|---|
| | | SEQ ID NO: 13 | | SEQ ID NO: 14 | | |
| | | G | H | I | J | |
| 10 | SEQ ID | 4,246 | 3,048 | 1,726 | 2,454 | P. fal 10K c/rxn |
| 9 | NO: 39 | 618,531 | 600,583 | 145,539 | 3,298 | B. div IVT 15 c/rxn |
| 8 | | 439,103 | 421,977 | 7,295 | 48,670 | B. dun IVT 15 c/rxn |
| 7 | | 4,661 | 2,419,801 | 43,673 | 16,001 | B. mic IVT 15 c/rxn |
| 6 | | 3,573 | 3,852 | 1,243 | 3,789 | Neg |
| 5 | SEQ ID | 1,538 | 2,040 | 636,577 | 1,472 | P. fal 10K c/rxn |
| 4 | NO: 37 | 1,313,625 | 1,403,578 | 41,232 | 1,144,411 | B. div IVT 15 c/rxn |
| 3 | | 1,464,595 | 1,660,711 | 379,047 | 252,130 | B. dun IVT 15 c/rxn |
| 2 | | 1,827,977 | 1,878,981 | 543,761 | 1,896,462 | B. mic IVT 15 c/rxn |
| 1 | | 2,724 | 1,371 | 1,544 | 1,320 | Neg |

| | | SEQ ID NO: 1 | | SEQ ID NO: 5 | | | |
|---|---|---|---|---|---|---|---|
| | | SEQ ID NO: 15 | | SEQ ID NO: 16 | | SEQ ID NO: 18 | |
| | | A | B | C | D | E | F |
| 10 | SEQ ID | 6,408 | 5,690 | 1,278 | 1,722 | 1,724 | 2,646 |
| 9 | NO: 39 | 144,774 | 478,638 | 207,863 | 4,342 | 167,329 | 1,078,348 |
| 8 | | 197,399 | 17,034 | 260,958 | 607,257 | 172,231 | 934,843 |
| 7 | | 40,088 | 28,810 | 2,472,660 | 2,440,145 | 2,404,314 | 2,487,783 |
| 6 | | 1,795 | 2,431 | 1,561 | 911 | 1,192 | 3,614 |
| 5 | SEQ ID | 1,197,623 | 1,474 | 939 | 1,303 | 958 | 1,949 |
| 4 | NO: 37 | 1,471,176 | 1,396,263 | 1,493,545 | 137,001 | 1,553,344 | 1,509,390 |
| 3 | | 1,765,530 | 1,753,318 | 1,950,334 | 1,982,086 | 1,758,977 | 1,690,431 |
| 2 | | 805,769 | 424,446 | 2,039,764 | 1,998,885 | 1,941,034 | 1,985,950 |
| 1 | | 1,631 | 1,963 | 1,292 | 1,149 | 1,233 | 38,660 |

| | | SEQ ID NO: 5 | | | | |
|---|---|---|---|---|---|---|
| | | SEQ ID NO: 20 | | SEQ ID NO: 21 | | |
| | | G | H | I | J | |
| 10 | SEQ ID | 1,419 | 1,582 | 703 | 3,712 | P. fal 10K c/rxn |
| 9 | NO: 39 | 401,756 | 346,658 | 98,181 | 219,007 | B. div IVT 15 c/rxn |
| 8 | | 220,859 | 657,682 | 137,758 | 124,133 | B. dun IVT 15 c/rxn |
| 7 | | 2,416,779 | 2,391,258 | 91,104 | 2,492,731 | B. mic IVT 15 c/rxn |
| 6 | | 2,345 | 2,848 | 631 | 659 | Neg |
| 5 | SEQ ID | 1,492 | 193,967 | 984 | 1,949 | P. fal 10K c/rxn |
| 4 | NO: 37 | 520,765 | 929,879 | 756,537 | 1,462,395 | B. div IVT 15 c/rxn |
| 3 | | 1,647,079 | 1,357,270 | 334,747 | 1,183,608 | B. dun IVT 15 c/rxn |
| 2 | | 2,043,012 | 95,200 | 1,937,688 | 1,875,971 | B. mic IVT 15 c/rxn |
| 1 | | 956 | 1,542 | 1,262 | 2,454 | Neg |

For the primers and detection probes screened in Group 2, not all primer-probe combinations consistently amplified and detected all species and some combinations resulted in high analyte signals for *P. falciparum*. Analyte RLU results for this group are listed in Table 6. Preferred candidates in this group were SEQ ID NO:3 promoter provider paired with SEQ ID NO:27, SEQ ID NO:28, SEQ ID NO:29 primers and SEQ ID NO:39 detection probe.

TABLE 6

Analyte RLU Results for Group 2.

| | Control | | | | | |
|---|---|---|---|---|---|---|
| | SEQ ID NO: 3<br>SEQ ID NO: 39 | | | | | |
| | A | B | C | D | E | F |
| | SEQ ID NO: 21 | | | SEQ ID NO: 24 | | |
| 10 | 5,538 | 2,060 | 3,451 | 912 | 1,957 | 732 |
| 9 | 2,777,487 | 1,462,676 | 2,411,623 | 42,352 | 261,061 | 36,259 |

TABLE 6-continued

| Analyte RLU Results for Group 2. | | | | | | |
|---|---|---|---|---|---|---|
| 8 | 2,090,779 | 2,104,742 | 1,619,218 | 344,375 | 87,780 | 46,539 |
| 7 | 2,422,490 | 2,421,930 | 1,995,715 | 392,494 | 1,060,155 | 2,468,927 |
| 6 | 4,111 | 1,487 | 1,423 | 616 | 698 | 994 |
| | SEQ ID NO: 23 | | | SEQ ID NO: 75 | | |
| 5 | 913 | 886 | 1,458 | 979 | 613 | 618 |
| 4 | 722,789 | 19,023 | 52,416 | 13,234 | 1,273,210 | 130,514 |
| 3 | 1,099 | 1,330 | 667 | 5,314 | 2,137 | 1,401 |
| 2 | 2,228,374 | 1,820,781 | 2,162,670 | 1,959,300 | 2,524,372 | 1,916,040 |
| 1 | 1,198 | 608 | 878 | 556 | 532 | 1,244 |

| | SEQ ID NO: 3<br>SEQ ID NO: 39 | | | | |
|---|---|---|---|---|---|
| | G | H | I | J | |
| | SEQ ID NO: 25 | | | SEQ ID NO: 31 | |
| 10 | 839 | 344 | 1,230 | 3,330 | P. fal 10K c/rxn |
| 9 | 35,686 | 7,687 | 5,156 | 1,589,735 | B. div IVT 15 c/rxn |
| 8 | 16,068 | 22,627 | 110,271 | 1,642,035 | B. dun IVT 15 c/rxn |
| 7 | 473,546 | 1,621,876 | 1,933,138 | 2,150,212 | B. mic IVT 15 c/rxn |
| 6 | 667 | 484 | 508 | 6,630 | Neg |
| | SEQ ID NO: 76 | | | SEQ ID NO: 31 | |
| 5 | 931 | 6,188 | 1,313 | 2,697 | P. fal 10K c/rxn |
| 4 | 901,920 | 816,015 | 1,059,461 | 2,138,285 | B. div IVT 15 c/rxn |
| 3 | 350,464 | 95,471 | 40,369 | 2,468,230 | B. dun IVT 15 c/rxn |
| 2 | 1,887,684 | 1,511,500 | 2,263,008 | 389,108 | B. mic IVT 15 c/rxn |
| 1 | 525 | 1,912 | 903 | 11,272 | Neg |

| | SEQ ID NO: 3<br>SEQ ID NO: 39 | | | | | |
|---|---|---|---|---|---|---|
| | A | B | C | D | E | F |
| | SEQ ID NO: 22 | | | SEQ ID NO: 26 | | |
| 10 | 924 | 972 | 8,531 | 5,715 | 1,627 | 1,017 |
| 9 | 87,406 | 60,599 | 71,115 | 778,850 | 371,058 | 574,028 |
| 8 | 3,156 | 3,152 | 5,092 | 150,582 | 154,380 | 75,725 |
| 7 | 2,201,409 | 2,091,981 | 2,098,983 | 2,181,859 | 2,111,286 | 2,220,157 |
| 6 | 1,263 | 1,258 | 1,013 | 3,675 | 1,411 | 1,513 |
| | SEQ ID NO: 28 | | | SEQ ID NO: 29 | | |
| 5 | 9,482 | 1,7459 | 1,830 | 3,932 | 4,278 | 3,258 |
| 4 | 1,169,497 | 1,283,384 | 1,523,739 | 2,167,497 | 2,112,640 | 2,151,586 |
| 3 | 1,118,901 | 584,074 | 1,104,469 | 1,847,271 | 1,481,735 | 2,000,601 |
| 2 | 2,291,400 | 2,263,798 | 2,225,197 | 2,338,122 | 2,318,877 | 2,287,637 |
| 1 | 5,439 | 3,796 | 1,551 | 3,578 | 8,224 | 4,044 |

| | SEQ ID NO: 3<br>SEQ ID NO: 39 | | | | |
|---|---|---|---|---|---|
| | G | H | I | J | |
| | SEQ ID NO: 27 | | | SEQ ID NO: 31 | |
| 10 | 3,853 | 3,043 | 3,064 | 5,868 | P. fal 10K c/rxn |
| 9 | 2,101,084 | 1,994,330 | 1,804,057 | 2,086,334 | B. div IVT 15 c/rxn |
| 8 | 1,697,144 | 1,487,220 | 1,493,662 | 1,951,476 | B. dun IVT 15 c/rxn |
| 7 | 2,376,261 | 2,312,253 | 2,351,514 | 2,288,840 | B. mic IVT 15 c/rxn |
| 6 | 2,573 | 7,310 | 5,289 | 6,093 | Neg |
| | SEQ ID NO: 30 | | | SEQ ID NO: 31 | |
| 5 | 7,941 | 10,249 | 397,486 | 2,514 | P. fal 10K c/rxn |
| 4 | 2,205,990 | 88,246 | 2,231,170 | 2,099,814 | B. div IVT 15 c/rxn |
| 3 | 2,143,050 | 2,113,739 | 2,037,798 | 1,730,715 | B. dun IVT 15 c/rxn |
| 2 | 2,307,754 | 2,272,338 | 2,206,558 | 2,230,915 | B. mic IVT 15 c/rxn |
| 1 | 14,896 | 2,781 | 1,362 | 1,916 | Neg |

Analyte RLU results for the primers and detection probes screened in Group 3 are listed in Table 7. Primers paired with detection probes SEQ ID NO:40 and SEQ ID NO:41 yielded high analyte signals for *P. falciparum*, negative samples and *Babesia* positive samples indicating poor design of the probe. Thus, SEQ ID NO:40 and SEQ ID NO:41 and were not included in additional examples. Combinations of SEQ ID NO:3 promoter provider with detection probe SEQ ID NO:38 (regardless of the primer used in this example) yielded high analyte signal in negative samples indicating a probable primer-probe interaction, and thus these oligomers were not included in additional examples. Candidates considered for use with additional detection probes were SEQ ID NO:1 promoter provider with SEQ ID NO:27 or 29 primers and SEQ ID NO:38 detection probe. For new T7 promoter provider screened in this group, SEQ ID NO:3 and 7 paired with SEQ ID NO:21 primer and SEQ ID NO:39 detection probe were considered. SEQ ID NO:9 promoter provider, SEQ ID NO:21 primer and SEQ ID NO:39 detection probe showed no amplification and detection of *Babesia* targets.

TABLE 7

Analyte RLU Results For Group 3

| | SEQ ID NO: 38 SEQ ID NO: 1 | | | SEQ ID NO: 41 SEQ ID NO: 1 | | | | | | | |
|---|---|---|---|---|---|---|---|---|---|---|---|
| | SEQ ID NO: 21 | SEQ ID NO: 27 | SEQ ID NO: 29 | SEQ ID NO: 21 | SEQ ID NO: 27 | SEQ ID NO: 29 | Blank | | | | |
| | A | B | C | D | E | F | G | H | I | J | |
| 10 | 1,183 | 4,868 | 2,229 | 1,999,003 | 1,973,790 | 1,943,078 | 8 | 8 | 9 | 8 | P.fal 10K c/rxn |
| 9 | 273,967 | 2,140,180 | 896,930 | 3,319,370 | 2,458,639 | 1,891,471 | 9 | 9 | 8 | 8 | B.div IVT 15 c/rxn |
| 8 | 2,569,264 | 2,530,890 | 2,494,566 | 3,175,342 | 2,598,410 | 2,129,032 | 8 | 7 | 5 | 8 | B.dun IVT 15 c/rxn |
| 7 | 2,481,447 | 2,349,620 | 2,600,164 | 3,769,511 | 2,880,852 | 2,707,608 | 9 | 7 | 8 | 24 | B.mic IVT 15 c/rxn |
| 6 | 1,792 | 2,291 | 4,106 | 1,373,994 | 2,056,230 | 2,277,790 | 9 | 5 | 9 | 8 | Neg |
| 5 | 2,503 | 12,777 | 8,428 | 2,386,352 | 1,947,735 | 2,160,802 | 10 | 7 | 7 | 10 | P.fal 10K c/rxn |
| 4 | 2,177,455 | 2,061,853 | 1,646,064 | 3,297,211 | 2,150,824 | 2,802,834 | 9 | 7 | 7 | 7 | B.div IVT 15 c/rxn |
| 3 | 2,508,586 | 2,634,974 | 2,567,929 | 3,430,103 | 2,765,117 | 3,556,389 | 8 | 6 | 9 | 8 | B.dun IVT 15 c/rxn |
| 2 | 2,601,774 | 2,583,708 | 2,551,550 | 3,333,080 | 3,719,802 | 3,344,092 | 8 | 8 | 9 | 9 | B.mic IVT 15 c/rxn |
| 1 | 835 | 2,079 | 2,581 | 1,960,393 | 2,096,053 | 2,145,235 | 7 | 5 | 9 | 10 | Neg |

| | | SEQ ID NO: 3 | | | | | | | | | | |
|---|---|---|---|---|---|---|---|---|---|---|---|---|
| | | SEQ ID NO: 15 | | SEQ ID NO: 16 | | SEQ ID NO: 18 | | SEQ ID NO: 20 | | SEQ ID NO: 21 | | |
| | | A | B | C | D | E | F | G | H | I | J | |
| 10 | SEQ ID NO: 39 | 3,873 | 2,436 | 5,785 | 2,743 | 2,406 | 1,968 | 1,535 | 2,439 | 2,493 | 2,249 | P.fal 10K c/rxn |
| 9 | | 1,918,232 | 1,880,797 | 1,368,977 | 2,094,325 | 1,486,108 | 2,119,826 | 1,912,598 | 882,449 | 1,936,565 | 2,170,010 | B.div IVT 15 c/rxn |
| 8 | | 1,602,380 | 1,776,094 | 2,135,880 | 2,225,590 | 2,031,084 | 2,095,064 | 1,893,023 | 1,800,511 | 2,240,797 | 2,087,446 | B.dun IVT 15 c/rxn |
| 7 | | 375,283 | 981,890 | 2,375,662 | 2,447,002 | 2,298,733 | 2,218,629 | 2,463,996 | 2,234,843 | 2,323,282 | 2,352,415 | B.mic IVT 15 c/rxn |
| 6 | | 5,902 | 6,937 | 7,033 | 7,979 | 2,758 | 3,564 | 2,246 | 1,866 | 2,602 | 1,792 | Neg |
| 5 | SEQ ID NO: 37 | 7,609 | 150,048 | 314,165 | 25,323 | 1,726,513 | 1,674 | 1,777 | 1,730 | 1,460 | 5,274 | P.fal 10K c/rxn |
| 4 | | 1,942,612 | 1,891,974 | 1,684,635 | 1,968,192 | 1,669,451 | 1,881,606 | 1,842,528 | 1,892,595 | 1,944,571 | 1,882,381 | B.div IVT 15 c/rxn |
| 3 | | 1,966,629 | 1,993,188 | 2,063,195 | 2,071,412 | 1,901,864 | 1,960,251 | 1,996,707 | 1,995,486 | 2,032,943 | 1,995,159 | B.dun IVT 15 c/rxn |
| 2 | | 829,468 | 1,477,651 | 2,146,350 | 2,147,242 | 2,049,500 | 2,063,691 | 2,057,722 | 2,091,173 | 2,110,461 | 2,140,647 | B.mic IVT 15 c/rxn |
| 1 | | 1,553 | 4,723 | 190,368 | 12,971 | 1,949 | 1,627 | 7,879 | 1,642 | 1,779 | 1,602 | Neg |

Conclusions:

The results of this initial screening demonstrated that not all primers and probes reliably amplify and detect all *Babesia* species. Some candidates were not specific to *Babesia*, showing some amplification of *P. falciparum*, while other candidates demonstrated false positives, false negatives and/or primer-probe interactions. Initial screening of amplification and detection systems identified several candidates that show sensitive and specific detection of *B. microti, B. divergens* and *B. duncani*. These candidates do not cross react with *P. falciparum* further demonstrating specificity of the systems. The sensitive and specific combinations from this example were considered for further sensitivity and specificity evaluation.

EXAMPLE 2: Secondary Oligo Screening for the *Babesia* Assay

Objective:

Candidate amplification combinations identified in Example 1 for the *Babesia* Assay using the manual Procleix Enhanced Semi-automated System (eSAS) were screened on the fully automated Procleix Panther System to determine the best candidates in terms of specificity and sensitivity using *Babesia* Species in-vitro transcripts (IVT).

Materials and Methods:

Candidate amplification systems were tested on the automated Procleix Panther system (Grifols Diagnostics Solutions, Inc.). Combinations of amplification and detection oligomers tested are listed in Table 8. Sequences for each oligo are listed in Table 9. A total of 8 conditions were screened. Conditions screened were tested against 45 replicates of a negative panel and 6 replicates each of diluted *Babesia* in-vitro transcripts (IVT) for *B. microti, B. divergens* and *B. duncani* (SEQ ID NOs:61, 62, & 63, respectively) at 30 c/ml. An assay calibrator comprising a *B. microti* IVT panel at 500 c/mL was included to determine the analyte cutoff for the run. The assay software uses the analyte cutoff to determine if samples are reactive or non-reactive. Samples with a signal to cutoff ratio of >1 are considered reactive, while those <1 are non-reactive. Assay Reagents used included the following: a Target Capture Reagent (TCR) comprising of a single Target Capture Oligo (TCO) added at a concentration of 5 pmoles per reaction; an Amplification Reagent comprising one T7 promoter provider and one non-T7 primer each added at a concentration of 10 pmoles per reaction; a Probe reagent consisting of 1 acridinium-ester (AE) labeled probe added at a total concentration of 5e6 Relative Light Units (RLU) per reaction to a solution of; Enzyme Reagent; and Selection Reagent.

A second round of oligo screening was performed to follow up on candidate systems identified in Example 1. Conditions tested in this group are listed in Table 10. Sequences for each oligo are listed in Table 11. A total of 6 additional conditions were screened. Conditions screened were tested against 8 replicates of a negative sample and 7 replicates of diluted *Babesia* in-vitro transcripts (IVT) for each of *B. microti, B. divergens* and *B. duncani* at 100, 30, and 10 c/ml. A cross reactivity panel consisting of 8 replicates *P. falciparum* IVT at 1e6 c/mL was also tested to determine if the system is specific to *Babesia* in the presence of *Plasmodium*. An assay calibrator made from a *B. microti* IVT panel at 500 c/mL.

TABLE 8

Conditions 1-8 Tested on the Panther System

| Condition # | Target Capture Oligo | T7 Primer | Non-T7 Primer | Probe |
|---|---|---|---|---|
| 1 | SEQ ID NO: 43 | SEQ ID NO: 1 | SEQ ID NO: 11 | SEQ ID NO: 37 |
| 2 | SEQ ID NO: 43 | SEQ ID NO: 1 | SEQ ID NO: 27 | SEQ ID NO: 39 |
| 3 | SEQ ID NO: 43 | SEQ ID NO: 1 | SEQ ID NO: 27 | SEQ ID NO: 38 |
| 4 | SEQ ID NO: 43 | SEQ ID NO: 1 | SEQ ID NO: 13 | SEQ ID NO: 37 |
| 5 | SEQ ID NO: 43 | SEQ ID NO: 3 | SEQ ID NO: 21 | SEQ ID NO: 37 |
| 6 | SEQ ID NO: 43 | SEQ ID NO: 7 | SEQ ID NO: 21 | SEQ ID NO: 37 |
| 7 | SEQ ID NO: 43 | SEQ ID NO: 7 | SEQ ID NO: 27 | SEQ ID NO: 39 |
| 8 | SEQ ID NO: 43 | SEQ ID NO: 5 | SEQ ID NO: 21 | SEQ ID NO: 37 |

TABLE 9

Sequences for Oligos listed in Table 8.

| Reagent | Short Name | Sequence 5'-3' |
|---|---|---|
| TCR | SEQ ID NO: 43 | uaggccaauacccuaccguccttttaaaaaaaaaaaaaaaaaaaaaaaaaaaaa |
| Amplification | SEQ ID NO: 1 | aatttaatacgactcactatagggagattcacctctgacagttaaatacgaa |
| | SEQ ID NO: 3 | aatttaatacgactcactatagggagaacagttaaatacgaatgcccccaa |
| | SEQ ID NO: 5 | aatttaatacgactcactatagggagattcacctctgacagttaaatac |
| | SEQ ID NO: 7 | aatttaatacgactcactatagggagagctttcgcagtagttcgtctttaacaaatc |
| | SEQ ID NO: 13 | cttgaatactacagcatggaataa |
| | SEQ ID NO: 21 | agaaaactagagtgtttcaa |
| | SEQ ID NO: 27 | atggaataatgaagtaggac |
| Probe | SEQ ID NO: 37 | ugaaguaggacuuugguucu |
| | SEQ ID NO: 38 | uaaugguuaauaggagcaguug |
| | SEQ ID NO: 39 | aguaaugguuaauaggagca |

TABLE 10

| Conditions 9-14 tested on the Panther System | | | | |
|---|---|---|---|---|
| Condition | Target Capture Oligo | T7 Primer | Non T7 Primer | Probe |
| 9 | SEQ ID NO: 43 | SEQ ID NO: 7 | SEQ ID NO: 21 | SEQ ID NOs: 37 + 42 |
| 10 | SEQ ID NO: 43 | SEQ ID NO: 7 | SEQ ID NO: 32 | SEQ ID NOs: 37 + 42 |
| 11 | SEQ ID NO: 43 | SEQ ID NO: 7 | SEQ ID NO: 33 | SEQ ID NOs: 37 + 42 |
| 12 | SEQ ID NO: 43 | SEQ ID NO: 7 | SEQ ID NO: 34 | SEQ ID NOs: 37 + 42 |
| 13 | SEQ ID NO: 43 | SEQ ID NO: 7 | SEQ ID NO: 35 | SEQ ID NOs: 37 + 42 |
| 14 | SEQ ID NO: 43 | SEQ ID NO: 7 | SEQ ID NO: 36 | SEQ ID NOs: 37 + 42 |

TABLE 11

| Sequences for Oligos listed in Table 10. | | |
|---|---|---|
| Reagent | Short Name | Sequence 5'-3' |
| TCR | SEQ ID NO: 43 | uaggccaauacccuaccgucc tttaaaaaaaaaaaaaaaaaa aaaaaaaaaaaa |
| Amplification | SEQ ID NO: 7 | aatttaatacgactcactata gggagagctttcgcagtagtt cgtctttaacaaatc |
| | SEQ ID NO: 21 | agaaaactagagtgtttcaa |
| | SEQ ID NO: 32 | agaaaactagagtgtttca |
| | SEQ ID NO: 33 | agaaaattagagtgtttcaa |
| | SEQ ID NO: 34 | gagaaaactagagtgtttcaa |
| | SEQ ID NO: 35 | gagaaaattagagtgtttcaa |
| | SEQ ID NO: 36 | tgagaaaactagagtgtttc |

TABLE 11-continued

| Sequences for Oligos listed in Table 10. | | |
|---|---|---|
| Reagent | Short Name | Sequence 5'-3' |
| Probe | SEQ ID NO: 37 | ugaaguaggacuuugguucu |
| | SEQ ID NO: 42 | aguaggacuuugguucu |

Results:

An analyte signal cutoff of 100,000 RLU was used to determine reactivity for specimens screened for Conditions 1-8 in Table 12. Samples above this cutoff were considered reactive. Conditions 1 and 4 yielded a false positive rate in negative specimens of 22% and 13% respectively indicating a primer interaction with the probe. Condition 7 was unable to detect *B. divergens* and *B. duncani* IVT at 30 c/mL at 100% reactivity. Due to the high rate of false positives seen in this example using the SEQ ID NO:1 promoter provider, additional screening was performed on alternative candidates.

TABLE 12

| Results for Conditions 1-8 | | | | | | |
|---|---|---|---|---|---|---|
| Condition # | Sample Description | Valid | Reactive | % Reactive | Average Analyte RLU | StdDev Analyte RLU |
| 1 | *B. microti* Calibrator | 3 | 3 | 100 | 2,895,211 | 95,178 |
| | Negative Buffer | 45 | 10 | 22 | 83,538 | 169,164 |
| | *B. microti* 30 c/mL | 6 | 6 | 100 | 2,785,208 | 192,438 |
| | *B. duncani* 30 c/mL | 6 | 6 | 100 | 2,704,843 | 52,325 |
| | *B. divergens* 30 c/mL | 5 | 5 | 100 | 2,679,799 | 131,010 |
| 2 | *B. microti* Calibrator | 3 | 3 | 100 | 2,164,104 | 85,510 |
| | Negative Buffer | 45 | 0 | 0 | 1,419 | 881 |
| | *B. microti* 30 c/mL | 5 | 5 | 100 | 2,184,976 | 107,021 |
| | *B. duncani* 30 c/mL | 5 | 5 | 100 | 1,842,832 | 79,094 |
| | *B. divergens* 30 c/mL | 5 | 5 | 100 | 1,710,700 | 484,713 |
| 3 | *B. microti* Calibrator | 3 | 3 | 100 | 5,202,778 | 356,597 |
| | Negative Buffer | 45 | 0 | 0% | 5,048 | 2,938 |
| | *B. microti* 30 c/mL | 6 | 6 | 100 | 5,282,576 | 336,909 |
| | *B. duncani* 30 c/mL | 6 | 6 | 100 | 4,987,308 | 396,702 |
| | *B. divergens* 30 c/mL | 6 | 6 | 100 | 4,898,995 | 261,124 |
| 4 | *B. microti* Calibrator | 3 | 3 | 100 | 2,847,426 | 127,963 |
| | Negative Buffer | 45 | 6 | 13 | 62,163 | 212,258 |
| | *B. microti* 30 c/mL | 6 | 6 | 100 | 2,920,118 | 186,525 |
| | *B. duncani* 30 c/mL | 6 | 6 | 100 | 2,637,399 | 213,549 |
| | *B. divergens* 30 c/mL | 6 | 6 | 100 | 2,555,922 | 322,889 |
| 5 | *B. microti* Calibrator | 3 | 3 | 100 | 2,614,010 | 43,029 |
| | Negative Buffer | 45 | 0 | 0 | 1,064 | 604 |
| | *B. microti* 30 c/mL | 6 | 6 | 100 | 2,562,482 | 60,848 |
| | *B. duncani* 30 c/mL | 6 | 6 | 100 | 2,317,458 | 47,231 |
| | *B. divergens* 30 c/mL | 6 | 6 | 100 | 2,329,932 | 33,382 |
| 6 | *B. microti* Calibrator | 3 | 3 | 100 | 2,849,900 | 59,411 |
| | Negative Buffer | 45 | 0 | 0 | 1,007 | 548 |
| | *B. microti* 30 c/mL | 6 | 6 | 100 | 2,779,409 | 77,390 |
| | *B. duncani* 30 c/mL | 6 | 6 | 100 | 2,472,381 | 110,379 |
| | *B. divergens* 30 c/mL | 6 | 6 | 100 | 2,608,790 | 176,482 |

TABLE 12-continued

| Results for Conditions 1-8 | | | | | | |
|---|---|---|---|---|---|---|
| Condition # | Sample Description | Valid | Reactive | % Reactive | Average Analyte RLU | StdDev Analyte RLU |
| 7 | *B. microti* Calibrator | 3 | 3 | 100 | 5,706,224 | 96,503 |
| | Negative Buffer | 45 | 0 | 0 | 3,062 | 1,006 |
| | *B. microti* 30 c/mL | 6 | 6 | 100 | 5,513,204 | 219,801 |
| | *B. duncani* 30 c/mL | 6 | 2 | 33 | 124,483 | 155,936 |
| | *B. divergens* 30 c/mL | 6 | 3 | 50 | 301,854 | 494,564 |
| 8 | *B. microti* Calibrator | 3 | 3 | 100 | 2,963,935 | 70,693 |
| | Negative Buffer | 45 | 0 | 0 | 932 | 645 |
| | *B. microti* 30 c/mL | 6 | 6 | 100 | 2,977,421 | 189,225 |
| | *B. duncani* 30 c/mL | 6 | 6 | 100 | 2,678,642 | 179,586 |
| | *B. divergens* 30 c/mL | 6 | 6 | 100 | 2,517,233 | 223,392 |

In the previous round of screening, several candidates showed good sensitivity and specificity for *Babesia* species IVT. Condition 6 had good sensitivity and specificity with strong analyte signal for the *Babesia* IVT specimens tested and low analyte signal for negative specimens. Additional screening was performed on the Panther system using the SEQ ID NO:7 promoter provider paired with a number of non-T7 primers to determine the performance of these oligomer combinations. Condition 12 had the best performance of the conditions screened in this round. Condition 12 had best performance in terms of percent reactivity for all levels tested for all *Babesia* species IVTs and strongest RLU signal for all levels. Condition 12 also had the lowest analyte signal for negative specimens.

TABLE 13

| Results for Conditions 9-14. | | | | | | | |
|---|---|---|---|---|---|---|---|
| Condition # | Sample Description | Level | Valid | Reactive | % Reactive | Average Analyte RLU | StdDev Analyte RLU |
| 9 | Negative Calibrator | 0 | 3 | 0 | 0 | 3,064 | 2,870 |
| | *B. microti* Calibrator | 500 c/mL | 3 | 3 | 100 | 2,634,036 | 20,467 |
| | *B. microti* IVT | 100 c/mL | 7 | 7 | 100 | 1,782,835 | 124,480 |
| | | 30 c/mL | 7 | 6 | 86 | 1,478,196 | 136,864 |
| | | 10 c/mL | 7 | 5 | 71 | 1,504,124 | 110,673 |
| | *B. duncani* IVT | 100 c/mL | 7 | 7 | 100 | 1,615,981 | 207,184 |
| | | 30 c/mL | 7 | 7 | 100 | 1,046,502 | 282,167 |
| | | 10 c/mL | 7 | 6 | 86 | 817,242 | 310,430 |
| | *B. divergens* IVT | 100 c/mL | 7 | 7 | 100 | 1,107,329 | 280,864 |
| | | 30 c/mL | 7 | 7 | 100 | 780,602 | 285,167 |
| | | 10 c/mL | 7 | 3 | 43 | 312,826 | 199,281 |
| | Negative IC Buffer | 0 | 8 | 0 | 0 | 921 | 1,069 |
| | *P. falciparum* IVT | 1.00e6 c/mL | 8 | 0 | 0 | 1,546 | 1,944 |
| 10 | Negative Calibrator | 0 | 3 | 0 | 0 | 2,083 | 1,176 |
| | *B. microti* Calibrator | 500 c/mL | 3 | 3 | 100 | 2,612,367 | 134,872 |
| | *B. microti* IVT | 100 c/mL | 7 | 7 | 100 | 1,841,300 | 261,033 |
| | | 30 c/mL | 7 | 6 | 86 | 1,329,659 | 395,229 |
| | | 10 c/mL | 7 | 4 | 57 | 708,829 | 275,561 |
| | *B. duncani* IVT | 100 c/mL | 7 | 7 | 100 | 1,475,991 | 196,296 |
| | | 30 c/mL | 7 | 7 | 100 | 717,189 | 386,202 |
| | | 10 c/mL | 7 | 4 | 57 | 471,736 | 348,996 |
| | *B. divergens* IVT | 100 c/mL | 7 | 7 | 100 | 910,674 | 330,110 |
| | | 30 c/mL | 7 | 6 | 86 | 565,166 | 200,817 |
| | | 10 c/mL | 7 | 3 | 43 | 158,352 | 37,831 |
| | Negative IC Buffer | 0 | 8 | 0 | 0 | 2,802 | 2,381 |
| | *P. falciparum* IVT | 1.00e6 c/mL | 8 | 0 | 0 | 3,459 | 3,274 |
| 11 | Negative Calibrator | 0 | 3 | 0 | 0 | 1,687 | 1,471 |
| | *B. microti* Calibrator | 500 c/mL | 3 | 3 | 100 | 2,476,171 | 150,100 |
| | *B. microti* IVT | 100 c/mL | 7 | 7 | 100 | 1,887,931 | 90,174 |
| | | 30 c/mL | 7 | 7 | 100 | 1,042,715 | 590,288 |
| | | 10 c/mL | 7 | 2 | 29 | 961,097 | 598,572 |
| | *B. duncani* IVT | 100 c/mL | 7 | 7 | 100 | 1,402,621 | 146,419 |
| | | 30 c/mL | 7 | 7 | 100 | 580,415 | 252,668 |
| | | 10 c/mL | 7 | 4 | 57 | 252,969 | 139,120 |
| | *B. divergens* IVT | 100 c/mL | 7 | 7 | 100 | 903,456 | 261,139 |
| | | 30 c/mL | 7 | 7 | 100 | 484,118 | 271,417 |
| | | 10 c/mL | 7 | 6 | 86 | 283,109 | 129,194 |
| | Negative IC Buffer | 0 | 8 | 0 | 0 | 2,334 | 1,997 |
| | *P. falciparum* IVT | 1.00e6 c/mL | 8 | 0 | 0 | 2,035 | 1,681 |

TABLE 13-continued

| Results for Conditions 9-14. | | | | | | | |
|---|---|---|---|---|---|---|---|
| Condition # | Sample Description | Level | Valid | Reactive | % Reactive | Average Analyte RLU | StdDev Analyte RLU |
| 12 | Negative Calibrator | 0 | 3 | 0 | 0 | 370 | 640 |
| | *B. microti* Calibrator | 500 c/mL | 3 | 3 | 100 | 2,742,289 | 194,078 |
| | *B. microti* IVT | 100 c/mL | 7 | 7 | 100 | 2,092,032 | 386,586 |
| | | 30 c/mL | 7 | 7 | 100 | 1,568,851 | 376,918 |
| | | 10 c/mL | 7 | 5 | 71 | 1,334,103 | 542,119 |
| | *B. duncani* IVT | 100 c/mL | 7 | 7 | 100 | 1,867,880 | 208,460 |
| | | 30 c/mL | 7 | 7 | 100 | 1,264,832 | 533,439 |
| | | 10 c/mL | 7 | 7 | 100 | 881,072 | 287,187 |
| | *B. divergens* IVT | 100 c/mL | 7 | 7 | 100 | 1,456,923 | 228,759 |
| | | 30 c/mL | 7 | 7 | 100 | 1,013,056 | 162,035 |
| | | 10 c/mL | 7 | 6 | 86 | 941,635 | 247,989 |
| | Negative IC Buffer | 0 | 8 | 0 | 0 | 391 | 944 |
| | *P. falciparum* IVT | 1.00e6 c/mL | 8 | 0 | 0 | 479 | 744 |
| 13 | Negative Calibrator | 0 | 3 | 0 | 0 | 18 | 31 |
| | *B. microti* Calibrator | 500 c/mL | 3 | 3 | 100 | 2,618,344 | 183,612 |
| | *B. microti* IVT | 100 c/mL | 7 | 7 | 100 | 1,689,812 | 234,944 |
| | | 30 c/mL | 7 | 7 | 100 | 1,295,755 | 316,505 |
| | | 10 c/mL | 7 | 5 | 71 | 494,319 | 480,634 |
| | *B. duncani* IVT | 100 c/mL | 7 | 5 | 71 | 644,015 | 376,799 |
| | | 30 c/mL | 7 | 7 | 100 | 1,026,959 | 141,543 |
| | | 10 c/mL | 7 | 7 | 100 | 1,808,125 | 209,910 |
| | *B. divergens* IVT | 100 c/mL | 7 | 7 | 100 | 1,129,487 | 153,036 |
| | | 30 c/mL | 7 | 7 | 100 | 670,066 | 221,406 |
| | | 10 c/mL | 7 | 6 | 86 | 270,616 | 143,462 |
| | Negative IC Buffer | 0 | 8 | 0 | 0 | 400 | 644 |
| | *P. falciparum* IVT | 1.00e6 c/mL | 8 | 0 | 0 | 1,237 | 1,803 |
| 14 | Negative Calibrator | 0 | 3 | 0 | 0 | 673 | 843 |
| | *B. microti* Calibrator | 500 c/mL | 3 | 3 | 100 | 2,656,960 | 89,493 |
| | *B. microti* IVT | 100 c/mL | 7 | 7 | 100 | 2,364,847 | 143,184 |
| | | 30 c/mL | 7 | 6 | 86 | 2,051,745 | 116,278 |
| | | 10 c/mL | 7 | 5 | 71 | 1,450,039 | 626,015 |
| | *B. duncani* IVT | 100 c/mL | 7 | 4 | 57 | 1,136,704 | 353,951 |
| | | 30 c/mL | 7 | 7 | 100 | 1,839,238 | 336,415 |
| | | 10 c/mL | 7 | 7 | 100 | 2,315,286 | 141,813 |
| | *B. divergens* IVT | 100 c/mL | 7 | 7 | 100 | 1,650,341 | 270,259 |
| | | 30 c/mL | 7 | 7 | 100 | 1,068,065 | 468,460 |
| | | 10 c/mL | 7 | 3 | 43 | 1,459,374 | 758,660 |
| | Negative IC Buffer | 0 | 8 | 0 | 0 | 574 | 689 |
| | *P. falciparum* IVT | 1.00e6 c/mL | 8 | 0 | 0 | 941 | 1,394 |

Conclusions:

Several candidate systems identified on the manual eSAS system yielded good specificity and sensitivity with *Babesia* species IVTs for the *Babesia* Assay during secondary screening on the fully automated Panther system. Others combinations showed poor sensitivity (Condition 7) or specificity (Condition 1 and 4) and were not advanced to additional screening. A second round of screening on the Panther system identified a new system (Condition 12) with sensitivity in lower dilutions of *Babesia* species IVTs superior to other conditions tested and good specificity for the *Babesia* assay.

EXAMPLE 3: Clinical Sample Screening

Objective:

Candidate amplification systems previously identified for the *Babesia* Assay on the manual Procleix Enhanced Semi-automated System (eSAS) were screened on the fully automated Procleix Panther System to determine the best candidates in terms of specificity and sensitivity using a *Babesia* clinical sample. Primers screened in this example are the same as Example 2. This experiment served as an additional test to determine the best performing candidates.

Materials and Methods:

Candidate amplification systems were tested on the automated Procleix Panther system. Combinations tested are listed in Table 14. Sequences for each oligo are listed in Table 15. A total of 8 conditions were screened. Conditions screened were tested using 9 replicates each of a lysed negative whole blood and diluted *Babesia*-infected clinical sample. The *Babesia* clinical sample consisted of a PCR Positive *Babesia*-infected human red blood cell (RBC) sample. The sample was received with an estimated parasite per mL value. Based upon the estimated parasite per mL value, the clinical sample was diluted in normal negative human whole blood to an estimated 30, 10, and 3 parasites per mL. The diluted *Babesia*-infected whole blood was lysed at a 1 to 6 ratio or 0.8 mL of whole blood in 4.8 mL of lysis solution Aptima Urine Transport Medium (commercially available). The negative panel was lysed according to the same procedure. Assay Reagents used included the following: a Target Capture Reagent (TCR) comprising of a single Target Capture Oligo (TCO) added at a concentration of 5 pmoles per reaction; an Amplification Reagent comprising one T7 promoter provider and one non-T7 primer each added at a concentration of 10 pmoles per reaction; a Probe reagent consisting of 1 acridinium-ester (AE) labeled probe added at a total concentration of 5e6 Relative Light Units (RLU) per reaction to a solution of; Enzyme Reagent; and Selection Reagent.

Conditions tested in this group are listed in Table 16. Sequences for each oligo are listed in Table 17. A total of 6 additional conditions were screened. Conditions were tested using 5 replicates of each of a *Babesia*-negative whole blood sample and a diluted *Babesia*-infected whole blood clinical sample. Prior to testing the negative and positive samples, the parasite concentration of the *Babesia*-infected clinical sample was estimated by using a calibration curve. The calibration curve was generated using lysates from serial dilutions of a known standard (a quantified *Babesia*-positive whole blood specimen). The clinical samples and the serial dilutions of the known standard were tested using a real-time assay. The Ttimes from each of the dilutions of the known standard were plotted against the parasites/mL to generate an equation. The equation was then used to convert Ttime to parasites/mL when the clinical sample was run using the same assay. The clinical sample was then diluted in normal negative human whole blood to an estimated 30 and 10 parasites per mL. The diluted clinical sample was lysed at a ratio of 1 mL whole blood to 3 mL lysis buffer. An assay calibrator comprising a *B. microti* IVT panel at 500 c/mL was also used. Similar to the screening described in the above examples, a single TCO was added to TCR at 5 pmoles per reaction, One T7 promoter provider and one non-T7 primer were added to Amplification Reagent at 10 pmoles per reaction each. The Probe reagent in this round of screening consisted of SEQ ID NO:37 detection probe oligomer at 2.5e6 RLU per reaction and SEQ ID NO:42 detection probe oligomer at 5e6 RLU per reaction.

TABLE 14

Conditions 1-8 Tested on Panther

| Condition # | Target Capture Oligo | T7 Primer | Non-T7 Primer | Probe |
|---|---|---|---|---|
| 1 | SEQ ID NO: 43 | SEQ ID NO: 1 | SEQ ID NO: 11 | SEQ ID NO: 37 |
| 2 | SEQ ID NO: 43 | SEQ ID NO: 1 | SEQ ID NO: 27 | SEQ ID NO: 39 |
| 3 | SEQ ID NO: 43 | SEQ ID NO: 1 | SEQ ID NO: 27 | SEQ ID NO: 38 |
| 4 | SEQ ID NO: 43 | SEQ ID NO: 1 | SEQ ID NO: 13 | SEQ ID NO: 37 |
| 5 | SEQ ID NO: 43 | SEQ ID NO: 3 | SEQ ID NO: 21 | SEQ ID NO: 37 |
| 6 | SEQ ID NO: 43 | SEQ ID NO: 7 | SEQ ID NO: 21 | SEQ ID NO: 37 |
| 7 | SEQ ID NO: 43 | SEQ ID NO: 7 | SEQ ID NO: 27 | SEQ ID NO: 39 |
| 8 | SEQ ID NO: 43 | SEQ ID NO: 5 | SEQ ID NO: 21 | SEQ ID NO: 37 |

TABLE 15

Sequences for Oligos listed in Table 14.

| Reagent | Short name | Sequence 5'-3' |
|---|---|---|
| TCR | SEQ ID NO: 43 | uaggccaauacccuaccgu cctttaaaaaaaaaaaaaa aaaaaaaaaaaaaaa |
| Amplification | SEQ ID NO: 1 | aatttaatacgactcacta tagggagattcacctctga cagttaaatacgaa |
| | SEQ ID NO: 3 | aatttaatacgactcacta tagggagaacagttaaata cgaatgcccccaa |
| | SEQ ID NO: 5 | aatttaatacgactcacta tagggagattcacctctga cagttaaatac |
| | SEQ ID NO: 7 | aatttaatacgactcacta tagggagagctttcgcagt agttcgtctttaacaaatc |
| | SEQ ID NO: 13 | cttgaatactacagcatgg aataa |
| | SEQ ID NO: 21 | agaaaactagagtgtttcaa |
| | SEQ ID NO: 27 | atggaataatgaagtaggac |
| Probe | SEQ ID NO: 37 | ugaaguaggacuuugguucu |
| | SEQ ID NO: 38 | uaaugguuaauaggagcagu ug |
| | SEQ ID NO: 39 | aguaaugguuaauaggagca |

TABLE 16

| Conditions 9-14 tested on Panther | | | | |
|---|---|---|---|---|
| Condition # | Target Capture Oligo | T7 Primer | Non-T7 Primer | Probe |
| 9 | SEQ ID NO: 43 | SEQ ID NO: 7 | SEQ ID NO: 21 | SEQ ID NOs: 37 + 42 |
| 10 | SEQ ID NO: 43 | SEQ ID NO: 7 | SEQ ID NO: 32 | SEQ ID NOs: 37 + 42 |
| 11 | SEQ ID NO: 43 | SEQ ID NO: 7 | SEQ ID NO: 33 | SEQ ID NOs: 37 + 42 |
| 12 | SEQ ID NO: 43 | SEQ ID NO: 7 | SEQ ID NO: 34 | SEQ ID NOs: 37 + 42 |
| 13 | SEQ ID NO: 43 | SEQ ID NO: 7 | SEQ ID NO: 35 | SEQ ID NOs: 37 + 42 |
| 14 | SEQ ID NO: 43 | SEQ ID NO: 7 | SEQ ID NO: 36 | SEQ ID NOs: 37 + 42 |

TABLE 17

| Sequences for Oligos listed in Table 16. | | |
|---|---|---|
| Reagent | SEQ ID NO: | Sequence 5'-3' |
| TCR | SEQ ID NO: 43 | uaggccaauacccuaccgu cctttaaaaaaaaaaaaaa aaaaaaaaaaaaaaaa |
| Amplification | SEQ ID NO: 7 | aatttaatacgactcacta tagggagagctttcgcagt agttcgtctttaacaaatc |
| | SEQ ID NO: 21 | agaaaactagagtgtttcaa |
| | SEQ ID NO: 32 | agaaaactagagtgtttca |
| | SEQ ID NO: 33 | agaaaattagagtgtttcaa |
| | SEQ ID NO: 34 | gagaaaactagagtgtttcaa |
| | SEQ ID NO: 35 | gagaaaattagagtgtttcaa |
| | SEQ ID NO: 36 | tgagaaaactagagtgtttc |

TABLE 17-continued

| Sequences for Oligos listed in Table 16. | | |
|---|---|---|
| Reagent | SEQ ID NO: | Sequence 5'-3' |
| Probe | SEQ ID NO: 37 | ugaaguaggacuuugguucu |
| | SEQ ID NO: 42 | aguaggacuuugguucu |

Results:

An analyte signal cutoff of 100,000 RLU was used to determine reactivity for specimens screened for Conditions 1-8 in Table 18. Samples above this cutoff were considered reactive. Conditions 1 and 4 yielded a false positive in lysed negative whole blood specimens at a rate of 11% and 33%, respectively. Conditions 2, 5 and 8 detected *Babesia* at less than 100% in lysed *Babesia*-infected clinical samples at 10 and 3 parasites per mL. Due to the high rate of false positives with SEQ ID NO:1 promoter provider and the high number of lower performing candidates, additional screening was performed to identify alternative candidates.

TABLE 18

| Average Analyte Results for Conditions 1-9 testing lysed Clinical Sample Dilutions on the Panther System. | | | | | | |
|---|---|---|---|---|---|---|
| Condition # | Sample Description | Valid | Reactive | % Reactive | Average Analyte RLU | StdDev Analyte RLU |
| 1 | *B. microti* Calibrator | 3 | 3 | 100% | 2,895,211 | 95,178 |
| | *Babesia* ARC 0 p/mL | 9 | 1 | 11% | 43,072 | 111,361 |
| | *Babesia* ARC 3 p/mL | 9 | 9 | 100% | 2,881,463 | 51,926 |
| | *Babesia* ARC 10 p/mL | 9 | 9 | 100% | 2,947,197 | 42,332 |
| | *Babesia* ARC 30 p/mL | 9 | 9 | 100% | 2,921,132 | 65,204 |
| 2 | *B. microti* Calibrator | 3 | 3 | 100% | 2,164,104 | 85,510 |
| | *Babesia* ARC 0 p/mL | 9 | 0 | 0% | 655 | 63 |
| | *Babesia* ARC 3 p/mL | 9 | 6 | 67% | 1,263,656 | 996,750 |
| | *Babesia* ARC 10 p/mL | 9 | 9 | 100% | 2,134,186 | 27,346 |
| | *Babesia* ARC 30 p/mL | 9 | 9 | 100% | 2,167,935 | 51,972 |
| 3 | *B. microti* Calibrator | 3 | 3 | 100% | 5,202,778 | 356,597 |
| | *Babesia* ARC 0 p/mL | 9 | 0 | 0% | 1,460 | 140 |
| | *Babesia* ARC 3 p/mL | 9 | 9 | 100% | 5,018,781 | 930,364 |
| | *Babesia* ARC 10 p/mL | 9 | 9 | 100% | 5,282,309 | 286,096 |
| | *Babesia* ARC 30 p/mL | 9 | 9 | 100% | 5,347,545 | 183,066 |
| 4 | *B. microti* Calibrator | 3 | 3 | 100% | 2,847,426 | 127,963 |
| | *Babesia* ARC 0 p/mL | 9 | 3 | 33% | 248,507 | 581,559 |
| | *Babesia* ARC 3 p/mL | 9 | 9 | 100% | 2,970,739 | 88,830 |
| | *Babesia* ARC 10 p/mL | 9 | 9 | 100% | 3,007,234 | 76,308 |
| | *Babesia* ARC 30 p/mL | 9 | 9 | 100% | 3,034,392 | 82,795 |
| 5 | *B. microti* Calibrator | 3 | 3 | 100% | 2,614,010 | 43,029 |
| | *Babesia* ARC 0 p/mL | 9 | 0 | 0% | 1,103 | 519 |
| | *Babesia* ARC 3 p/mL | 9 | 7 | 78% | 1,714,505 | 1,012,100 |
| | *Babesia* ARC 10 p/mL | 9 | 6 | 67% | 1,372,599 | 1,250,728 |
| | *Babesia* ARC 30 p/mL | 9 | 9 | 100% | 2,455,769 | 54,600 |
| 6 | *B. microti* Calibrator | 3 | 3 | 100% | 2,849,900 | 59,411 |
| | *Babesia* ARC 0 p/mL | 9 | 0 | 0% | 765 | 72 |
| | *Babesia* ARC 3 p/mL | 9 | 9 | 100% | 2,784,938 | 77,517 |
| | *Babesia* ARC 10 p/mL | 9 | 9 | 100% | 2,741,662 | 63,328 |
| | *Babesia* ARC 30 p/mL | 9 | 9 | 100% | 2,734,625 | 46,780 |

TABLE 18-continued

Average Analyte Results for Conditions 1-9 testing lysed Clinical Sample Dilutions on the Panther System.

| Condition # | Sample Description | Valid | Reactive | % Reactive | Average Analyte RLU | StdDev Analyte RLU |
|---|---|---|---|---|---|---|
| 7 | *B. microti* Calibrator | 3 | 3 | 100% | 5,706,224 | 96,503 |
| | *Babesia* ARC 0 p/mL | 9 | 0 | 0% | 3,383 | 1,376 |
| | *Babesia* ARC 3 p/mL | 9 | 9 | 100% | 5,192,042 | 511,510 |
| | *Babesia* ARC 10 p/mL | 9 | 9 | 100% | 5,240,227 | 135,033 |
| | *Babesia* ARC 30 p/mL | 9 | 9 | 100% | 5,425,945 | 228,652 |
| 8 | *B. microti* Calibrator | 3 | 3 | 100% | 2,963,935 | 70,693 |
| | *Babesia* ARC 0 p/mL | 9 | 0 | 0% | 1,163 | 596 |
| | *Babesia* ARC 3 p/mL | 9 | 5 | 56% | 1,708,479 | 1,623,206 |
| | *Babesia* ARC 10 p/mL | 9 | 9 | 100% | 3,060,059 | 187,482 |
| | *Babesia* ARC 30 p/mL | 9 | 9 | 100% | 3,112,370 | 83,507 |

In the previous round of screening, only a few candidates showed good sensitivity and specificity for lysed *Babesia*-infected clinical samples. Condition 6 had good specificity and sensitivity detecting the lysed clinical sample down to 3 parasites per mL at 100% reactivity and with strong analyte signal for the positive specimens tested and low analyte signal for negative specimens. Additional screening was performed on the Panther system using SEQ ID NO:7 promoter provider paired with a number of additional non-T7 primers. Conditions in this round of screening were again tested using lysed dilutions of a clinical sample. All conditions except Condition 11 detected the 30 and 10 p/mL lysates at 100% reactivity. None of conditions yielded any false positives in negative specimens.

TABLE 19

Average Analyte Results for Conditions 9-14 testing lysed Wadsworth Center (WC) sample dilutions on Panther.

| Condition # | Sample Description | Level | Valid | Reactive | % Reactive | Average Analyte RLU | StdDev Analyte RLU |
|---|---|---|---|---|---|---|---|
| 9 | Negative Calibrator | 0 | 3 | 0 | 0 | 3,064 | 2,870 |
| | *B. microti* Calibrator | 500 c/mL | 3 | 3 | 100 | 2,634,036 | 20,467 |
| | *Babesia* WC | 30 p/mL | 5 | 5 | 100 | 2,335,851 | 100,942 |
| | | 10 p/mL | 5 | 5 | 100 | 1,970,484 | 170,746 |
| | Negative | 0 | 5 | 0 | 0 | 1,229 | 1,061 |
| 10 | Negative Calibrator | 0 | 3 | 0 | 0 | 2,083 | 1,176 |
| | *B. microti* Calibrator | 500 c/mL | 3 | 3 | 100 | 2,612,367 | 134,872 |
| | *Babesia* WC | 30 p/mL | 5 | 5 | 100 | 1,700,198 | 40,527 |
| | | 10 p/mL | 5 | 5 | 100 | 1,639,511 | 112,124 |
| | Negative | 0 | 5 | 0 | 0 | 879 | 899 |
| 11 | Negative Calibrator | 0 | 3 | 0 | 0 | 1,687 | 1,471 |
| | *B. microti* Calibrator | 500 c/mL | 3 | 3 | 100 | 2,476,171 | 150,100 |
| | *Babesia* WC | 30 p/mL | 5 | 5 | 100 | 2,083,998 | 176,018 |
| | | 10 p/mL | 5 | 3 | 60 | 833,006 | 790,769 |
| | Negative | 0 | 5 | 0 | 0 | 2,237 | 1,256 |
| 12 | Negative Calibrator | 0 | 3 | 0 | 0 | 370 | 640 |
| | *B. microti* Calibrator | 500 c/mL | 3 | 3 | 100 | 2,742,289 | 194,078 |
| | *Babesia* WC | 30 p/mL | 5 | 5 | 100 | 2,220,041 | 241,385 |
| | | 10 p/mL | 5 | 5 | 100 | 2,098,119 | 175,399 |
| | Negative | 0 | 5 | 0 | 0 | 970 | 648 |
| 13 | Negative Calibrator | 0 | 3 | 0 | 0 | 18 | 31 |
| | *B. microti* Calibrator | 500 c/mL | 3 | 3 | 100 | 2,618,344 | 183,612 |
| | *Babesia* WC | 30 p/mL | 5 | 5 | 100 | 1,861,428 | 170,146 |
| | | 10 p/mL | 5 | 5 | 100 | 2,032,573 | 300,759 |
| | Negative | 0 | 5 | 0 | 0 | 405 | 871 |
| 14 | Negative Calibrator | 0 | 3 | 0 | 0 | 673 | 843 |
| | *B. microti* Calibrator | 500 c/mL | 3 | 3 | 100 | 2,656,960 | 89,493 |
| | *Babesia* WC | 30 p/mL | 5 | 5 | 100 | 2,523,855 | 87,845 |
| | | 10 p/mL | 5 | 5 | 100 | 2,376,263 | 191,838 |
| | Negative | 0 | 5 | 0 | 0 | 2,381 | 4,735 |

Conclusion:

Considering results for secondary screening with *Babesia* species IVTs in Example 2 and screening with clinical sample in this example, Conditions 3 and 6 were the best candidates in terms of specificity and sensitivity. Condition 12 had the best performance of the conditions screened in Conditions 9-14. Condition 12 had best performance in terms of percent reactivity for all levels tested and consistent RLU signal for all levels tested for *Babesia* species IVTs and lysed clinical sample dilutions on the Panther system. Additionally, Condition 12 had the lowest analyte signal for negative specimens.

From the foregoing, it will be appreciated that, although specific embodiments have been described herein for purposes of illustration, various modifications may be made without deviating from the spirit and scope of this explicit disclosure. Accordingly, the invention is not limited by the explicit disclosure. All publications, patents, and patent applications cited herein are hereby incorporated by reference in their entireties for all purposes.

EXAMPLE 4: *Babesia* IVTs and *Babesia* Positive Whole Blood Sample Screening Objective:

Candidate amplification systems were screened on the Procleix Panther System to determine the oligo candidates in terms of specificity and sensitivity using IVTs and a contrived *Babesia* clinical sample.

Materials and Methods:

Candidate amplification systems were tested on the automated Procleix Panther system. Combinations tested are listed in Table 20. Sequences for each oligo are listed in Table 21. A total of 8 conditions were screened. Conditions were screened using 16 replicates of panel members consisting of in-vitro transcript diluted in buffer for *B. microti, B. divergens, B. duncani,* and *B. venatorum* (SEQ ID NOs: 61, 62, 63, & 100) at either 30 c/mL or 10 c/mL. Conditions were also screened against 12 replicates each of a contrived clinical sample. The contrived clinical sample comprised a mixture of *Babesia*-negative human whole blood and *Babesia microti*-infected hamster whole blood (acquired from the American Red Cross (ARC)). In short, *Babesia microti* infected hamster blood having a predetermined parasitemia value was diluted with *Babesia*-negative human whole blood to yield an estimated 4 parasites/mL (p/mL) of an infected blood mixture. The infected blood mixture was then lysed at a 1 to 3 ratio (here using 0.9 mL of whole blood in 2.7 mL of an aqueous solution of 100 mM TRIS, 30 mM magnesium chloride, and 6% (v/v) LLS, at pH 7.5). The lysed infected blood mixture is referred to herein as a hamster blood lysate. In some test conditions hamster blood lysate was further diluted in negative lysate to a level equating to 0.01 parasites/mL. A negative lysate was prepared according to the same procedure. An assay positive calibrator consisted of a *B. microti* in-vitro transcript (IVT) (SEQ ID NO:61) panel at 500 c/mL. Negative calibrator and negative buffered specimens contained only buffer. Assay Reagents used consisted of: Target Capture Reagent (TCR) comprising of a single Target Capture Oligo (TCO) added at a concentration of approximately 5 pmoles per reaction; Amplification Reagent comprising of T7 and NT7 primers added at a concentration of approximately 5 pmoles each per reaction; Probe reagent consisting of acridinium-ester (AE) labeled probes added at a total concentration of approximately 1e6 Relative Light Units (RLU) per reaction. Commercially available Procleix Ultrio Plus Enzyme and Selection reagents were used.

TABLE 20

Conditions 1-8 Tested on Panther

| Condition # | Oligo Combination |
|---|---|
| 1 | SEQ ID NO: 89, SEQ ID NO: 7, SEQ ID NO: 82, SEQ ID NO: 84, SEQ ID NO: 34, SEQ ID NO: 86, SEQ ID NO: 91, SEQ ID NO: 42, SEQ ID NO: 98 |
| 2 | SEQ ID NO: 87, SEQ ID NO: 7, SEQ ID NO: 82, SEQ ID NO: 84, SEQ ID NO: 34, SEQ ID NO: 86, SEQ ID NO: 91, SEQ ID NO: 42, SEQ ID NO: 98 |
| 3 | SEQ ID NO: 43, SEQ ID NO: 87, SEQ ID NO: 89, SEQ ID NO: 82, SEQ ID NO: 84, SEQ ID NO: 34, SEQ ID NO: 86, SEQ ID NO: 91, SEQ ID NO: 42, SEQ ID NO: 98 |
| 4 | SEQ ID NO: 43, SEQ ID NO: 87, SEQ ID NO: 89, SEQ ID NO: 7, SEQ ID NO: 82, SEQ ID NO: 84, SEQ ID NO: 91, SEQ ID NO: 42, SEQ ID NO: 98 |
| 5 | SEQ ID NO: 43, SEQ ID NO: 87, SEQ ID NO: 89, SEQ ID NO: 7, SEQ ID NO: 82, SEQ ID NO: 86, SEQ ID NO: 91, SEQ ID NO: 42, SEQ ID NO: 98 |
| 6 | SEQ ID NO: 43, SEQ ID NO: 87, SEQ ID NO: 89, SEQ ID NO: 7, SEQ ID NO: 82, SEQ ID NO: 84, SEQ ID NO: 34, SEQ ID NO: 86, SEQ ID NO: 91 |
| 7 | SEQ ID NO: 43, SEQ ID NO: 87, SEQ ID NO: 89, SEQ ID NO: 7, SEQ ID NO: 82, SEQ ID NO: 84, SEQ ID NO: 34, SEQ ID NO: 86, SEQ ID NO: 92 |
| 8 | SEQ ID NO: 43, SEQ ID NO: 87, SEQ ID NO: 89, SEQ ID NO: 7, SEQ ID NO: 82, SEQ ID NO: 84, SEQ ID NO: 34, SEQ ID NO: 86, SEQ ID NO: 93 |

TABLE 21

Sequences for Oligos listed in Table 20.

| Seq # | Reagent | Class | Sequence (5'-3') |
|---|---|---|---|
| SEQ ID NO: 43 | TCR | Capture Oligo | uaggccaauacccuaccgucctttaaaaaaaaaaaaaaaaaaaaaaaaaaaaa |
| SEQ ID NO: 87 | | Capture Oligo | aaagacuuugauuucucucaaggtttaaaaaaaaaaaaaaaaaaaaaaaaaaaaa |

TABLE 21-continued

Sequences for Oligos listed in Table 20.

| Seq # | Reagent | Class | Sequence (5'-3') |
|---|---|---|---|
| SEQ ID NO: 89 | | Capture Oligo | caagaaagagcuaucaaucugucaauccttt aaaaaaaaaaaaaaaaaaaa aaaaaaaaa |
| SEQ ID NO: 7 | Amplification | T7 Primer | aatttaatacgactcactatagggagagctttcgcagtagttcgtctttaac aaatc |
| SEQ ID NO: 82 | | T7 Primer | aatttaatacgactcactatagggagaggcaaatgctttcgcagtagttigt ctttaaca |
| SEQ ID NO: 84 | | Non-T7 primer | gcggtaattccagctccaatag |
| SEQ ID NO: 34 | | Non-T7 primer | gagaaaactagagtgtttcaa |
| SEQ ID NO: 86 | | Non-T7 primer | cttgaatacticagca |
| SEQ ID NO: 91 | Probe | Probe | aguaggacuuugguuct |
| SEQ ID NO: 92 | | Probe | aguaggacuuugguuc |
| SEQ ID NO: 93 | | Probe | aguaggacuauugguuc |
| SEQ ID NO: 42 | | Probe | aguaggacuuugguucu |
| SEQ ID NO: 98 | | Probe | aguaggacuauugguucu |

Results:

An analyte signal cutoff calculated was calculated using negative and positive calibrators and the Panther Software. Test results yielding a signal to cutoff ratio of greater than or equal to 1.0 were considered reactive. All conditions tested detected *B. microti, B. divergens, B. duncani* and *B. venatorum* as well as the hamster blood lysate panel members to some degree (Table 22). All conditions detected all species at 100% reactivity at the 30c/mL level except Condition 5 in which 15 out of 16 replicates were detected. For conditions 1-5 all hamster blood lysate panels at 4 p/mL were 100% reactive except Condition 2 in which 8 out of 12 replicates were detected. For Conditions 6-8, which tested hamster blood lysates at 0.01 p/mL, results show 14/16, 15/16, and 14/16 positive. There were no false positive in negative reactions.

TABLE 22

Average Analyte Results for Conditions 1-8 testing.

| Condition # | Sample Description | c/mL | Valid | Reactive | % Reactive | Analyte RLUs | SD Analyte RLUs | Analyte S/CO | SD Analyte S/CO |
|---|---|---|---|---|---|---|---|---|---|
| 1 | Negative Calibrator | 0 | 3 | 0 | 0.0 | 0 | 0 | 0.00 | 0.00 |
| | Positive Calibrator | 500 | 3 | 3 | 100.0 | 1,310,257 | 45,626 | 33.33 | 1.16 |
| | *B. microti* | 30 c/mL | 16 | 16 | 100.0 | 691,469 | 302,377 | 17.59 | 7.69 |
| | | 10 c/mL | 16 | 15 | 93.8 | 648,137 | 282,342 | 16.49 | 7.18 |
| | *B. duncani* | 30 c/mL | 16 | 16 | 100.0 | 1,100,887 | 309,481 | 28.01 | 7.87 |
| | | 10 c/mL | 16 | 16 | 100.0 | 973,540 | 246,634 | 24.77 | 6.27 |
| | *B. divergens* | 30 c/mL | 16 | 16 | 100.0 | 1,099,778 | 294,789 | 27.98 | 7.50 |
| | | 10 c/mL | 16 | 16 | 100.0 | 959,134 | 335,825 | 24.40 | 8.54 |
| | *B. venatorum* | 30 c/mL | 16 | 16 | 100.0 | 1,052,533 | 280,903 | 26.78 | 7.15 |
| | | 10 c/mL | 16 | 16 | 100.0 | 902,987 | 309,501 | 22.97 | 7.87 |
| | Negative Buffer | 0 c/mL | 16 | 0 | 0.0 | 0 | 0 | 0.00 | 0.00 |
| | Hamster Blood Lysate | 4 | 12 | 12 | 100.0 | 1,307,118 | 28,853 | 33.25 | 0.73 |
| | Hamster Blood Lysate | 0 | 12 | 0 | 0.0 | 4 | 15 | 0.00 | 0.00 |
| 2 | Negative Calibrator | 0 | 3 | 0 | 0.0 | 14 | 24 | 0.00 | 0.00 |
| | Positive Calibrator | 500 | 3 | 3 | 100.0 | 1,360,358 | 88,289 | 33.32 | 2.16 |
| | *B. microti* | 30 c/mL | 16 | 16 | 100.0 | 990,774 | 405,235 | 24.27 | 9.93 |
| | | 10 c/mL | 16 | 13 | 81.3 | 674,210 | 358,804 | 16.52 | 8.79 |
| | *B. duncani* | 30 c/mL | 16 | 16 | 100.0 | 1,261,270 | 234,066 | 30.90 | 5.73 |
| | | 10 c/mL | 16 | 16 | 100.0 | 1,010,323 | 412,156 | 24.75 | 10.10 |
| | *B. divergens* | 30 c/mL | 16 | 16 | 100.0 | 1,136,882 | 281,770 | 27.85 | 6.90 |
| | | 10 c/mL | 16 | 16 | 100.0 | 1,138,086 | 288,726 | 27.88 | 7.07 |
| | *B. venatorum* | 30 c/mL | 16 | 16 | 100.0 | 1,095,242 | 357,885 | 26.83 | 8.77 |
| | | 10 c/mL | 16 | 16 | 100.0 | 979,611 | 405,233 | 24.00 | 9.93 |
| | Negative Buffer | 0 c/mL | 16 | 0 | 0.0 | 0 | 0 | 0.00 | 0.00 |
| | Hamster Blood Lysate | 4 | 12 | 8 | 66.7 | 1,148,331 | 589,637 | 28.13 | 14.44 |
| | Hamster Blood Lysate | 0 | 12 | 0 | 0.0 | 220 | 763 | 0.01 | 0.02 |

TABLE 22-continued

Average Analyte Results for Conditions 1-8 testing.

| Condition # | Sample Description | c/mL | Valid | Reactive | % Reactive | Analyte RLUs | SD Analyte RLUs | Analyte S/CO | SD Analyte S/CO |
|---|---|---|---|---|---|---|---|---|---|
| 3 | Negative Calibrator | 0 | 3 | 0 | 0.0 | 0 | 0 | 0.00 | 0.00 |
| | Positive Calibrator | 500 | 3 | 3 | 100.0 | 1,247,077 | 16,587 | 33.33 | 0.44 |
| | *B. microti* | 30 c/mL | 16 | 16 | 100.0 | 996,284 | 147,903 | 26.63 | 3.95 |
| | | 10 c/mL | 16 | 14 | 87.5 | 733,412 | 225,774 | 19.60 | 6.03 |
| | *B. duncani* | 30 c/mL | 16 | 16 | 100.0 | 1,154,290 | 46,421 | 30.85 | 1.24 |
| | | 10 c/mL | 16 | 16 | 100.0 | 1,051,223 | 93,259 | 28.10 | 2.49 |
| | *B. divergens* | 30 c/mL | 16 | 16 | 100.0 | 1,160,454 | 42,968 | 31.02 | 1.15 |
| | | 10 c/mL | 16 | 16 | 100.0 | 1,067,057 | 104,387 | 28.52 | 2.79 |
| | *B. venatorum* | 30 c/mL | 16 | 16 | 100.0 | 1,120,866 | 52,999 | 29.96 | 1.42 |
| | | 10 c/mL | 16 | 16 | 100.0 | 988,682 | 127,271 | 26.43 | 3.40 |
| | Negative Buffer | 0 c/mL | 16 | 0 | 0.0 | 0 | 0 | 0.00 | 0.00 |
| | Hamster Blood Lysate | 4 | 12 | 12 | 100.0 | 1,153,646 | 24,699 | 30.84 | 0.66 |
| | Hamster Blood Lysate | 0 | 12 | 0 | 0.0 | 0 | 0 | 0.00 | 0.00 |
| 4 | Negative Calibrator | 0 | 3 | 0 | 0.0 | 0 | 0 | 0.00 | 0.00 |
| | Positive Calibrator | 500 | 3 | 3 | 100.0 | 689,988 | 39,272 | 33.33 | 1.90 |
| | *B. microti* | 30 c/mL | 16 | 16 | 100.0 | 236,235 | 167,806 | 11.41 | 8.11 |
| | | 10 c/mL | 16 | 11 | 68.8 | 142,663 | 122,889 | 6.89 | 5.94 |
| | *B. duncani* | 30 c/mL | 16 | 16 | 100.0 | 331,217 | 55,106 | 16.00 | 2.66 |
| | | 10 c/mL | 16 | 16 | 100.0 | 174,519 | 88,419 | 8.43 | 4.27 |
| | *B. divergens* | 30 c/mL | 16 | 16 | 100.0 | 589,500 | 20,005 | 28.48 | 0.97 |
| | | 10 c/mL | 16 | 16 | 100.0 | 482,888 | 106,825 | 23.33 | 5.16 |
| | *B. venatorum* | 30 c/mL | 16 | 16 | 100.0 | 560,636 | 66,993 | 27.09 | 3.24 |
| | | 10 c/mL | 16 | 16 | 100.0 | 406,685 | 129,080 | 19.65 | 6.24 |
| | Negative Buffer | 0 c/mL | 16 | 0 | 0.0 | 0 | 0 | 0.00 | 0.00 |
| | Hamster Blood Lysate | 4 | 12 | 12 | 100.0 | 870,137 | 62,684 | 42.04 | 3.03 |
| | Hamster Blood Lysate | 0 | 12 | 0 | 0.0 | 0 | 0 | 0.00 | 0.00 |
| 5 | Negative Calibrator | 0 | 3 | 0 | 0.0 | 0 | 0 | 0.00 | 0.00 |
| | Positive Calibrator | 500 | 3 | 3 | 100.0 | 1,041,315 | 125,263 | 33.33 | 4.01 |
| | *B. microti* | 30 c/mL | 16 | 15 | 93.8 | 306,912 | 218,362 | 9.82 | 6.99 |
| | | 10 c/mL | 16 | 11 | 68.8 | 243,155 | 159,289 | 7.78 | 5.10 |
| | *B. duncani* | 30 c/mL | 16 | 16 | 100.0 | 748,753 | 281,035 | 23.97 | 9.00 |
| | | 10 c/mL | 16 | 16 | 100.0 | 751,922 | 286,380 | 24.07 | 9.17 |
| | *B. divergens* | 30 c/mL | 16 | 16 | 100.0 | 807,915 | 258,741 | 25.86 | 8.28 |
| | | 10 c/mL | 16 | 16 | 100.0 | 643,482 | 256,352 | 20.60 | 8.21 |
| | *B. venatorum* | 30 c/mL | 16 | 16 | 100.0 | 792,659 | 264,484 | 25.37 | 8.47 |
| | | 10 c/mL | 16 | 16 | 100.0 | 747,633 | 243,096 | 23.93 | 7.78 |
| | Negative Buffer | 0 c/mL | 16 | 0 | 0.0 | 0 | 0 | 0.00 | 0.00 |
| | Hamster Blood Lysate | 4 | 12 | 12 | 100.0 | 1,410,648 | 33,678 | 45.16 | 1.08 |
| | Hamster Blood Lysate | 0 | 12 | 0 | 0.0 | 84 | 210 | 0.00 | 0.01 |
| 6 | Negative Calibrator | 0 c/mL | 3 | 0 | 0.0 | 0 | 0 | 0.00 | 0.00 |
| | Positive Calibrator | 500 c/mL | 3 | 3 | 100.0 | 524,314 | 5,119 | 33.33 | 0.33 |
| | *B. microti* | 30 c/mL | 16 | 16 | 100.0 | 507,560 | 25,719 | 32.26 | 1.64 |
| | *B. divergens* | 30 c/mL | 16 | 16 | 100.0 | 471,886 | 64,616 | 30.00 | 4.11 |
| | *B. duncani* | 30 c/mL | 16 | 16 | 100.0 | 502,786 | 46,565 | 31.96 | 2.96 |
| | *B. venatorum* | 30 c/mL | 16 | 16 | 100.0 | 495,758 | 19,503 | 31.51 | 1.24 |
| | Hamster Blood Lysate | 0.01 p/mL | 16 | 14 | 87.5 | 337,759 | 102,178 | 24.48 | 7.41 |
| | Negative Buffer | 0 c/mL | 16 | 0 | 0.0 | 145 | 387 | 0.00 | 0.00 |
| 7 | Negative Calibrator | 0 c/mL | 3 | 0 | 0.0 | 254 | 439 | 0.01 | 0.02 |
| | Positive Calibrator | 500 c/mL | 3 | 3 | 100.0 | 668,273 | 11,200 | 32.91 | 0.55 |
| | *B. microti* | 30 c/mL | 16 | 16 | 100.0 | 654,530 | 36,463 | 32.24 | 1.80 |
| | *B. divergens* | 30 c/mL | 16 | 16 | 100.0 | 652,634 | 44,688 | 32.14 | 2.20 |
| | *B. duncani* | 30 c/mL | 16 | 16 | 100.0 | 628,767 | 49,861 | 30.97 | 2.46 |
| | *B. venatorum* | 30 c/mL | 16 | 16 | 100.0 | 620,345 | 63,099 | 30.55 | 3.11 |

TABLE 22-continued

Average Analyte Results for Conditions 1-8 testing.

| Condition # | Sample Description | c/mL | Valid | Reactive | % Reactive | Analyte RLUs | SD Analyte RLUs | Analyte S/CO | SD Analyte S/CO |
|---|---|---|---|---|---|---|---|---|---|
| | Hamster Blood Lysate | 0.01 p/mL | 16 | 15 | 93.8 | 397,026 | 182,905 | 23.35 | 10.76 |
| | Negative Buffer | 0 c/mL | 16 | 0 | 0.0 | 91 | 151 | 0.00 | 0.00 |
| 8 | Negative Calibrator | 0 c/mL | 3 | 0 | 0.0 | 280 | 486 | 0.02 | 0.03 |
| | Positive Calibrator | 500 c/mL | 3 | 3 | 100.0 | 521,485 | 14,518 | 32.74 | 0.91 |
| | *B. microti* | 30 c/mL | 16 | 16 | 100.0 | 460,267 | 52,434 | 28.90 | 3.29 |
| | *B. divergens* | 30 c/mL | 16 | 16 | 100.0 | 423,530 | 61,700 | 26.59 | 3.87 |
| | *B. duncani* | 30 c/mL | 16 | 16 | 100.0 | 428,292 | 43,574 | 26.89 | 2.74 |
| | *B. venatorum* | 30 c/mL | 16 | 16 | 100.0 | 415,273 | 64,983 | 26.07 | 4.08 |
| | Hamster Blood Lysate | 0.01 p/mL | 16 | 14 | 87.5 | 198,996 | 127,811 | 13.96 | 8.97 |
| | Negative Buffer | 0 c/mL | 16 | 0 | 0.0 | 817 | 885 | 0.00 | 0.00 |

Conclusion:

Oligo combinations tested herein exemplify specific and sensitive capture, amplification, and detection of *Babesia* species including *B. microti, B. divergens, B. duncani*, and *B. ventorum* and demonstrated detection of *Babesia microti* parasite in whole blood.

SEQUENCES

| SEQ ID NO. | Sequence (5' to 3') | Comments |
|---|---|---|
| 1 | aatttaatacgactcactatagggagattcacctctgacagttaaatacgaa | T7 promoter primer |
| 2 | ttcacctctgacagttaaatacgaa | SEQ ID NO: 1 without promoter sequence |
| 3 | aatttaatacgactcactatagggagaacagttaaatacgaatgcccccaa | T7 promoter primer |
| 4 | acagttaaatacgaatgcccccaa | SEQ ID NO: 3 without promoter sequence |
| 5 | aatttaatacgactcactatagggagattcacctctgacagttaaatac | T7 promoter primer |
| 6 | ttcacctctgacagttaaatac | SEQ ID NO: 5 without promoter sequence |
| 7 | aatttaatacgactcactatagggagagctttcgcagtagttcgtcatttaacaaatc | T7 promoter primer |
| 8 | gctttcgcagtagttcgtctttaacaaatc | SEQ ID NO: 7 without promoter sequence |
| 9 | aatttaatacgactcactatagggagactttcgcagtagttcgtctttaac | T7 promoter primer |
| 10 | ctttcgcagtagttcgtctttaac | SEQ ID NO: 9 without promoter sequence |
| 11 | cttgaatactacagcatgga | Non-T7 primer |
| 12 | actacagcatggaataatga | Non-T7 primer |
| 13 | cttgaatactacagcatggaataa | Non-T7 primer |
| 14 | acttcagcatggaataatga | Non-T7 primer |
| 15 | cttgaatacttcagcatgga | Non-T7 primer |

-continued

| SEQ ID NO. | Sequence (5' to 3') | Comments |
|---|---|---|
| 16 | actncagcatggaataatga | Non-T7 primer, wherein "n" means a or g or c or t/u, or unknown, or other (WIPO Standard ST.25 (1998), Appendix 2, Table 1) |
| 17 | actwcagcatggaataatga | Non-T7 primer |
| 18 | cttgaatactncagcatgga | Non-T7 primer, wherein "n" means a or g or c or t/u, or unknown, or other (WIPO Standard ST.25 (1998), Appendix 2, Table 1) |
| 19 | cttgaatactwcagcatgga | Non-T7 primer |
| 20 | actttgagaaaactagagtg | Non-T7 primer |
| 21 | agaaaactagagtgtttcaa | Non-T7 primer |
| 22 | ataatgaagtaggactttgg | Non-T7 primer |
| 23 | aggactttggttctattttg | Non-T7 primer |
| 24 | ggttctattttgttggtt | Non-T7 primer |
| 25 | tggttctattttgttgg | Non-T7 primer |
| 26 | ggaataatgaagtaggacttt | Non-T7 primer |
| 27 | atggaataatgaagtaggac | Non-T7 primer |
| 28 | atggaataatgaagtagg | Non-T7 primer |
| 29 | gcatggaataatgaagtag | Non-T7 primer |
| 30 | tacagcatggaataatgaag | Non-T7 primer |
| 31 | tactacagcatggaataatg | Non-T7 primer |
| 32 | agaaaactagagtgtttca | Non-T7 primer |
| 33 | agaaaattagagtgtttcaa | Non-T7 primer |
| 34 | gagaaaactagagtgtttcaa | Non-T7 primer |
| 35 | gagaaaattagagtgtttcaa | Non-T7 primer |
| 36 | tgagaaaactagagtgtttc | Non-T7 primer |
| 37 | ugaaguaggacuuugguucu | Probe |
| 38 | uaaugguuaauaggagcaguug | Probe |
| 39 | aguaaugguuaauaggagca | Probe |
| 40 | ggacuuugguucuauuuuguugg | Probe |
| 41 | aaugguuaauaggagcaguuggggg | Probe |
| 42 | aguaggacuuugguucu | Probe |
| 43 | uaggccaauacccuaccgucctttaaaaaaaaaaaaaaaaaaaaaaaaaaaaaa | Target capture |
| 44 | uaggccaauacccuaccgucc | SEQ ID NO: 43, without capture tail sequence |

-continued

| SEQ ID NO. | Sequence (5' to 3') | Comments |
|---|---|---|
| 45 | atggaataatgaagtag | Same sequence in SEQ ID NOs: 27, 28, 29 and 31 |
| 46 | agaaaactagagtg | Same sequence in SEQ ID NOs: 20, 21, 32, 34 and 36 |
| 47 | agaaaattagagtg | Same sequence in SEQ ID NOs: 33 and 35. |
| 48 | agaaaaytagagtg | Substitutes y for c in SEQ ID NO: 46 and y for t in SEQ ID NO: 47, wherein "y" means c or t/u (WIPO Standard ST.25 (1998), Appendix 2, Table 1) |
| 49 | agaaaactagagtgtttc | Same sequence in SEQ ID NOs: 19, 20, 21, 32, 34 and 36. |
| 50 | agaaaattagagtgtttc | Same sequence in SEQ ID NOs: 33 and 35. |
| 51 | agaaaaytagagtgtttc | Substitutes y for c in SEQ ID NO: 49) and y for t in SEQ ID NO: 50, wherein "y" means c or t/u (WIPO Standard ST.25 (1998), Appendix 2, Table 1) |
| 52 | tactacagcatggaataa | Same sequence in SEQ ID NO: 13 and 31. |
| 53 | actncagcatgga | Residue "n" means a or g or c or t/u, or unknown, or other (WIPO Standard ST.25 (1998), Appendix 2, Table 1), and "other preferably means "i" or inosine |
| 54 | actwcagcatgga | |
| 55 | actacagcatgga | Same sequence as SEQ ID NO: 54, except that "n" is "a". |
| 56 | gtatttaactgt | Same sequence in SEQ ID NOs: 1, 3 and 5. |
| 57 | Gtatttaactgtcagaggtgaa | Same sequence in SEQ ID NOs: 1 and 5. |
| 58 | aatttaatacgactcactatagggaga | T7 promoter |
| 59 | aguaggacuuugguucu | Same sequence in SEQ ID NO: 42. |

-continued

| SEQ ID NO. | Sequence (5' to 3') | Comments |
|---|---|---|
| 60 | uaaugguuaauaggagca | Same sequence in SEQ ID NOs: 38 and 39. |
| 61 | gggcgaauuggguaccgggccccccucgaggucgacgcuuaguauaagcuuuua<br>uacagcgaaacugcgaauggcucauuaaaacaguuauaguuuauuugauguucgu<br>uuuacauggauaaccgugguaauucuagggcuaauacaugcucgaggcgcguuuu<br>cgcguggcguuuauuagacuuuaaccaacccuucggguaaucggugauucauaau<br>aaauuagcgaaucgcauggcuuugccggcgauguaucauucaaguuucugaccua<br>ucagcuuuggacgguaggguauuggccuaccggggcgacgacgggugacggggaa<br>uuggggguucgauuccggagagggagccugagaaacggcuaccacaucuaaggaag<br>gcagcaggcgcgcaaauuacccaauccugacacagggagguagugacaagaaauaa<br>caauacagggcuuaaagucuuguaauuggaaugaugggaaucuaaacccuuccca<br>gaguaucaauuggagggcaagucuggugccagcagccgcgguaauuccagcucca<br>auagcguauauuaaaguuguugcaguuaagaagcucguaguugaauuucugccuu<br>gucauuaaucucgcuuccgagcguuuuuuuauugacuuggcaucuucuggauuu<br>ggugccuucggguacuauuuuccaggauuuacuuugagaaaacuagaguguuuca<br>aacaggcauucgccuugaauacuacagcauggaauaaugaaguaggacuuugguu<br>cuauuuuguugguuauugagccagaguaaugguuaauaggagcaguuggggggca<br>uucguauuuaacugucagaggugaaauucuuagauuuguuaaagacgaacuacug<br>cgaaagcauuugccaaggauguuuucauuaaucaagaacgaaaguuaggggaucg<br>aagacgaucagauaccgucguaguccuaaccauaaacuaugccgacuagagauugg<br>aggucgucaguuuaaacgacuccuucagcaccuugagagaaaucaaagucuuugg<br>guucugggggggaguauggucgcaagucugaaacuuaaaggaauugacggaagggc<br>accaccaggcguggagccugcggcuuaauuugacucaacacgggaaaccucaccag<br>guccagacauagagaggauugacagauugauagcucuuucuugaugaauu | *B. microti* IVT Sequence |
| 62 | gggcgaauuggguaccgggccccccucgaggucgacgguaucgauaagcuugau<br>aucgaauuccugcagcccgggggauccaaccugguugauccugccaguagucaua<br>ugcuugucuuaaagauuaagccaugcaugucuaaguacaaacuuuuuacggugaa<br>acugcgaauggcucauuacaacaguuauaguuucuuugguauucguuuuccaugg<br>auaaccgugcuaauuguagggcuaauacaaguucgaggccuuuuggcggcguuua<br>uuaguucuaaaaccaucccuuuugguuuucggugauucauaauaaacuugcgaau<br>cgcaauuuuuugcgauggaccauucaaguuucugacccaucagcuugacgguagg<br>guauuggccuaccgaggcagcaacggguaacggggaauuaggguucgauuccgga<br>gagggagccugagaaacggcuaccacauccaaggaaggcagcaggcgcgcaaauua<br>cccaauccugacacagggagguagugacaagaaauaacaauacagggcaauugucu<br>uguaauuggaaugauggugaccuaaacccucaccagaguaacaauuggagggcaa<br>gucuggugccagcagccgcgguaauuccagcuccaauagcguauauuaaacuugu<br>ugcaguuaaaaagcucguaguugaauuuuugcgugguguuaauauugacuaaug<br>ucgagauugcacuucgcuuuugggauuuaucccuuuuuacuuugagaaaauuaga<br>guguuucaagcagacuuuugucuugaauacuucagcauggaauaauagaguagga<br>cuuugguucuauuuuguugguuugugaaccuuaguaaugguuaauaggaacggu<br>ugggggcauucguauuuaacugucagaggugaaauucuuagauuuguuaaagacg<br>aacuacugcgaaagcauuugccaaggacguuuucauuaaucaagaacgaaaguuag<br>gggaucgaagacgaucagauaccgucguaguccuaaccauaaacuaugccgacuag<br>ggauuggaggucgucauuuuuccgacuccuucagcaccuugagagaaaucaaagu<br>cuuuggguucugggggggaguauggucgcaaggcugaaacuuaaaggaauugacg<br>gaagggcaccaccaggcguggagccugcggcuuaauuugacucaacacggggaaac<br>ucaccagguccagacaauguuaggauugacagauugauagcucuuucuugauucu<br>uuggguggugcggcc | *B. divergens* IVT Sequence |
| 63 | gggcgaauuggguaccgggccccccucgaggucgacguugauccugccaguagu<br>cauaugcuugucuuaaagauuaagccaugcaugucuaaguauaaacuuuuauaug<br>gugaaacugcgaauggcucauuacaacaguuauaguuuauuugaaagucguuuuu<br>acauggauaaccgugcuaauuguagggcuaauacaugcucgaggccuuggcuccu<br>gucuuggcugcguuuauuagacucgaaaccuucccgcuugcgguacucggugauu<br>cauaauaaauuugcgaaucgcauggcuuuugccggcgaugguucauucaaguuuc<br>ugaccuaucagcuuuggacgguaggguauuggccuaccggggcagcgacggguaa<br>cggggaauuaggguucgauuccggagagggagccugagaaacggcuaccacaucu<br>aaggaaggcagcaggcgcgcaaauuacccaauacggacaccgugagguagugacaa<br>gaaauaacaauacagggcuuaaagcuuuguaauuggaaugaugggaauccaaaccc<br>cuuccagaguaucaauuggagggcaagucuggugccagcagccgcgguaauucca<br>gcuccaauagcguauauuaaacuuguugcaguuaaaaagcucguaguugaacuuc<br>ugccgcuuggccuuucguuccccuuggggguuucguucgccugguggcuuaccuc<br>uggcgguggaucuccauuugccaguuuuacuuugagaaaauuagaguguuucaa<br>gcaggcuuuugccuugaauacuucagcauggaauaauaaaguaggacuuugguuc<br>uauuuuguugguuucaggaccaaaguaaugguuaauaggaacaguuggggggcau<br>ucguauuuaacugucagaggugaaauucuuagauuuguuaaagacgaacuacugc<br>gaaagcauuugccaaggauguuuucauuaaucaagaacgaaaguuaggggcucga<br>agacgaucagauaccgucguaguccuaacuauaaacuaugccgacuagagauugga<br>ggucgucauuuuaaacgacuccuucagcaccuugagagaaaucaaagucuuuggg<br>uucugggggggaguauggucgcaaggcugaaacuuaaaggaauugacggaagggca<br>ccaccaggcguggagccugcggcuuaauuugacucaacacggggaaccucaccagg<br>uccagacauaguuaggauugacagauugauagcucgaauu | *B. duncani* IVT Sequence |

-continued

| SEQ ID NO. | Sequence (5' to 3') | Comments |
|---|---|---|
| 64 | gggcgaauuggguaccguagaaacugcgaacggcucauuaaaacaguuauagucu acuugacauuuuuauuauaaggauaacuacggaaaagcuguagcuaauacuugcu uuauuauccuuugauuuuuaucuuuggauaaguauuuguuaggccuuauaagaa aaaaguuauuaacuuaaggaauuauaacaaagaaguaacacguaauaaauuuauuu uauuuagugugguaucaaucgaguuucugaccuaucagcuuuugauguuagggua uuggccuaacauggcuaugacggguaacggggaauuagaguucgauuccggagag ggagccugagaaauagcuaccacaucuaaggaaggcagcaggcgcguaaauuaccc aauucuaaaaaagagagguagugacaagaaauaacaaugcaaggccaauuuuuggu uuuguaauuggaaugguggggaauuuaaaaccuucccagaguaacaauuggagggc aagucuggugccagcagccgcgguaauuccagcuccaauagcguauauuaaaauu guugcaguuaaaacgcucguaguugaauuucaaagaaucgauauuuuauuguaac uauucuaggggaacuauuuuagguuuucgcuuuaauacgcuuccucuauuauuau guucuuuaaauaacaaagauucuuuuuaaaauccccacuuuugcuuuuuuggga auuuguuacuuugaauaaauuagaggugucaaagcaaacaguuaaagcauuuacu guguuugaauacuauagcauggaauaacaaaauugaacaagcuaaaauuuuuugu ucuuuuuucuuauuuuggcuuaguuacgauuaauaggaguagcuuggggacauu cguauucagaugucagaggugaaauucuuagauuuucuggagacgaacaacugcg aaagcauuugucuaaaauacuuccauuaaucaagaacgaaaguuaagggagugaag acgaucagauaccgucguaaucuuaaccauaaacuaugccgacuagguguuggau gaaaguguuaaaaauaaaagucaucuuucuaggugacuuuuagauugcuuccuuc aguaccuuaugagaaaucaaagucuuugguucuggggcgaguauucgcgcaagc gagaaaguuaaaagaauugacggaagggcaccaccaggcguggagcuugcggcuu aauuugacucaacacggggaaacucacuaguuuaagacaagaguaggauugacaga uuaauagcucuuucuugauuucuuggauggugaugcauggccguuuuuaguucg ugaauaugauuugucugguuaauuccgauaacgaacgagaucggauccacuaguu cuagagcggcc | *P. falciparum* IVT Sequence |
| 65 | ugaaguaggacuuugguucuauuuuguugguuauugagccagaguaaugguuaa uaggagcaguuggggg | |
| 66 | ttcacctctgacagttaaatacgaatgcccccaa | Contains SEQ ID NOs: 56 and 57, which the target hybridising sequence can contain |
| 67 | tactncagcatggaataatgaagtaggactttgg | Contains SEQ ID NOs: 45 & 69, wherein "n" means a or g or c or t/u, or unknown, or other (WIPO Standard ST.25 (1998), Appendix 2, Table 1) |
| 68 | cttgaatactncagcatggaataatga | Contains SEQ ID NOs: 53, 54 or 55, which the target hybridising sequence can contain, wherein "n" means a or g or c or t/u, or unknown, or other (WIPO Standard ST.25 (1998), Appendix 2, Table 1) |
| 69 | atggaataatg | Contained in SEQ ID NO: 67 |
| 70 | actttgagaaaaytagagtgtttcaaa | Contains SEQ ID NOs: 46, 47, 48, 49, 50, and 51, wherein "y" means c or t/u (WIPO Standard ST.25 (1998), Appendix 2, Table 1) |

-continued

| SEQ ID NO. | Sequence (5' to 3') | Comments |
|---|---|---|
| 71 | aacctggttgatcctgccagtagtcatatgcttgtcttaaagattaagccatgcatgtcttagtat aagcttttatacagcgaaactgcgaatggctcattaaaacagttatagtttgatgttcgtttt acatggataaccgtggtaattctagggctaatacatgctcgaggcgcgttttcgcgtggcgttt attagactttaaccaacccttcgggtaatcggtgattcataataaattagcgaatcgcatggctt tgccggcgatgtatcattcaagtttctgacctatcagctttggacggtagggtattggcctacc ggggcgacgacgggtgacggggaattggggttcgattccggagagggagcctgagaaa cggctaccacatctaaggaaggcagcaggcgcgcaaattacccaatcctgacacagggag gtagtgacaagaaataacaatacagggcttaaagtcttgtaattggaatgatgggaatctaaa cccttcccagagtatcaattggagggcaagtctggtgccagcagccgcggtaattccagctc caatagcgtatattaaagttgttgcagttaagaagctcgtagttgaatttctgccttgtcattaatc tcgcttccgagcgtttttttattgacttggcatcttctggatttggtgccttcgggtactattttcca ggatttactttgagaaaactagagtgtttcaaacaggcattcgccttgaatactacagcatgga ataatgaagtaggactttggttctattttgttggttattgagccagagtaatggttaataggagca gttggggcattcgtatttaactgtcagaggtgaaattcttagatttgttaaagacgaactactg cgaaagcatttgccaaggatgttttcattaatcaagaacgaaagttaggggatcgaagacga tcagataccgtcgtagtcctaaccataaactatgccgactagagattggaggtcgtcagttta aacgactccttcagcaccttgagagaaatcaaagtctttgggttctgggggagtatggtcg caagtctgaaacttaaaggaattgacggaagggcaccaccaggcgtggagcctgcggctt aatttgactcaacacgggaaacctcaccaggtccagacatagagaggattgacagattgata gctctttcttgattctatgggtggtggtgcatggccgttcttagttggtggagtgatttgtctggtt aattccgttaacgaacgagaccttaacctgctaaattaggatctgggacaagctttgctgttcc agtatcgcttcttagagggactttgcgttcataaaacgcaaggaagtgtaaggcaataacag gtctgtgatgcccttagatgtcctgggctgcacgcgcgctacactgatgcattcaacgagtttt tccttggccgtcgggtccgggtaatcttacagtatgcatcgtgatggggatagattattgcaat tattaatcttgaacgaggaatgcctagtaggcgcgagtcatcagctcgtgccgactacgtcc ctgccctttgtacacaccgcccgtcgctcctaccgatcgagtgatccggtgaattattcggac caagaaacgtggattcgtccttcgtttttggaaagttttgtgaaccttatcacttaaaggaagg agaagtcgtaacaaggtttccgtaggtgaacctgcggaaggatcattc | GenBank Accession No: AY693840.1 *Babesia microti* isolate Gray 18S ribosomal RNA gene, partial sequence |
| 72 | aacctggttgatcctgccagtagtcatatgcttgtcttaaagattaagccatgcatgtctaagta caaactttttacggtgaaactgcgaatggctcattacaacagttatagtttctttggtattcgtttt ccatggataaccgtgctaattgtagggctaatacaagttcgaggccttttggcggcgtttatta gttctaaaaccatccctttttggttttcggtgattcataataaacttgcgaatcgcaatttttttgcgat ggaccattcaagtttctgacccatcagcttgacggtagggtattggcctaccgaggcagcaa cgggtaacggggaattagggttcgattccggagagggagcctgagaaacggctaccacat ccaaggaaggcagcaggcgcgcaaattacccaatcctgacacagggaggtagtgacaag aaataacaatacagggcaattgtcttgtaattggaatgatggtgacctaaaccctcaccagag taacaattggagggcaagtctggtgccagcagccgcggtaattccagctccaatagcgtata ttaaacttgttgcagttaaaaagctcgtagttgaatttttgcgtggtgttaatattgactaatgtcg agattgcacttcgcttttgggatttatcccttttttactttgagaaaattagagtgtttcaagcagac ttttgtcttgaatacttcagcatggaataatagagtaggactttggttctattttgttggtttgtgaa ccttagtaatggttaataggaacggdgggggcattcgtatttaactgtcagaggtgaaattctt agatttgttaaagacgaactactgcgaaagcatttgccaaggacgttttcattaatcaagaacg aaagttaggggatcgaagacgatcagataccgtcgtagtcctaaccataaactatgccgact agggattggaggtcgtcatttttccgactccttcagcaccttgagagaaatcaaagtctttggg ttctgggggagtatggtcgcaaggctgaaacttaaaggaattgacggaagggcaccacc aggcgtggagcctgcggcttaatttgactcaacacggggaaactcaccaggtccagacaat gttaggattgacagattgatagctctttcttgattctttgggtggtggtgcatggccgttcttagtt ggtggagtgatttgtctggttaattccgttaacgaacgagaccttaacctgctaactagtgtcc gtaaaaaggttcgtccgttacggtttgcttcttagagggactttgcggctctaagccgcaagg aagtttaaggcaataacaggtctgtgatgcccttagatgtcctgggctgcacgcgcgctaca ctgatgcattcatcgagttttatcccttcccgaaagggctgggtaatctttagtatgcatcgtga cggggattgatttttgcaattctaaatcatgaacgaggaatgcctagtatgcgcaagtcatcag cttgtgcagattacgtccctgccctttgtacacaccgcccgtcgctcctaccgatcgagtgatc cggtgaattattcggaccgtggccttttccgattcgtcggcttggcctagggaagtcttgtgaa ccttatcacttaaaggaaggagaagtcgtaacaaggtttccgtaggtgaacctgcggaagg atcattc | GenBank Accession No: AY789076.1 *Babesia divergens* 18S ribosomal RNA gene, partial sequence |
| 73 | ccttggttgatcctgccagtagtcatatgcttgtcttaaggattaagccatgcatgtctaagtata aacttttatatggtgaaactgcgaatggctcattacaacagttatagtttatttgaaagtcgttttt acatggataaccgtgctaattgtagggctaatacatgctcgaggccttggcttctgtcttggct gcgtttattagactcgaaaccttcccgcttgcggtactcggtgattcataataaatttgcgaatc gcatggcttttgccggcgatggttcattcaagtttctgacctatcagctttggacggtagggtat tggcctaccggggcagcgacgggtaacggggaattagggttcgattccggagagggagc ctgagaaacggctaccacatctaaggaaggcagcaggcgcgcaaattacccaatacggac accgtgaggtagtgacaagaaataacaatacagggctttaagctttgtaattggaatgatggg aatccaaaccccttccagagtatcaattggagggcaagtctggtgccagcagccgcggtaa ttccagctccaatagcgtatattaaacttgagcagttaaaaagctcgtagttgaacttctgccg cttggcctttcgttccccttggggtttcgttcgcctggtggcttacctctggcggtggttctccat ttgccagttttactttgagaaaattagagtgtttcaagcaggcttttgccttgaatacttcagcat ggaataataaagtaggactttggttctattttgttggtttcaggaccaaagtaatggttaatagg aacagttgggggcattcgtatttaactgtcagaggtgaaattcttagatttgttaaagacgaact actgcgaaagcatttgccaaggatgttttcattaatcaagaacgaaagttaggggctcgaag acgatcagataccgtcgtagtcctaactataaactatgccgactagagattggaggtcgtcat tttaaacgactccttcagcaccttgagagaaatcaaagtctttgggttctgggggagtatggt | GenBank Accession No: AY027815.1 *Babesia* sp. WA1 isolate CA5 18S ribosomal RNA gene, partial sequence |

-continued

| SEQ ID NO. | Sequence (5' to 3') | Comments |
|---|---|---|
| | cgcaaggctgaaacttaaaggaattgacggaagggcaccaccaggcgtggagcctgcgg<br>cttaatttgactcaacacggggaacctcaccaggtccagacatagttaggattgacagattga<br>tagctctttcttgattctatgggtagtggtgcatggccgttcttagttggtggagtgatttgtctgg<br>ttaattccgttaacgaacgagaccttaacctgctaaatagcagctgagaataatctcttgtttca<br>gttttgcttcttagagggactttgcggtcataaatcgcaaggaagtttaaggcaataacaggtc<br>tgtgatgcccttagatgtcctgggctgcacgcgcgctacactgatgcattcatcgagttttatc<br>cttgcccgaaagggtttggtaatctttagtatgcatcgtgatggggattgattattgcaattatta<br>atcatgaacgaggaatgcctagtaggcgcgagtcatcagctcgtgccgactacgtccctgc<br>cctttgtacacaccgcccgtcgctcctaccgatcgagtgatccggtgaattattcggaccgtg<br>acgcttctaattcgttagaaatgtctagggaagttttgtgaaccttatcacttaaaggaaggag<br>aagtcgtaacaaggtaccg | |
| 74 | tcaaagattaagccatgcaagtgaaagtatatatatattttatatgtagaaactgcgaacggctc<br>attaaaacagttatagtctacttgacatttttattataaggataactacggaaaagctgtagctaa<br>tacttgctttattatccttttgatttttatctttggataagtatttgttaggccttataagaaaaaagtta<br>ttaacttaaggaattataacaaagaagtaacacgtaataaatttattttatttagtgtgtatcaatc<br>gagtttctgacctatcagcttttgatgttagggtattggcctaacatggctatgacgggtaacg<br>gggaattagagttcgattccggagagggagcctgagaaatagctaccacatctaaggaag<br>gcagcaggcgcgtaaattacccaattctaaaaaagagaggtagtgacaagaaataacaatg<br>caaggccaatttttggttttgtaattggaatggtgggaatttaaaaccttcccagagtaacaatt<br>ggagggcaagtctggtgccagcagccgcggtaattccagctccaatagcgtatattaaaatt<br>gttgcagttaaaacgctcgtagttgaatttcaaagaatcgatattttattgtaactattctagggg<br>aactattttaggttttcgctttaatacgcttcctctattattatgttctttaaataacaaagattcttttt<br>aaaatccccacttttgcttttgctttttggggaatttgttactttgaataaattagaggtgtcaaag<br>caaacagttaaagcatttactgtgtttgaatactatagcatggaataacaaaattgaacaagct<br>aaaatttttgttcttttttcttattttggcttagttacgattaatagggagtagcttggggacattcgt<br>attcagatgtcagaggtgaaattcttagattttctggagacgaacaactgcgaaagcatttgtc<br>taaaatacttccattaatcaagaacgaaagttaagggagtgaagacgatcagataccgtcgta<br>atcttaaccataaactatgccgactaggtgttggatgaaagtgttaaaaataaaagtcatctttc<br>taggtgacttttagattgcttccttcagtaccttatgagaaatcaaagtctttgggttctggggcg<br>agtattcgcgcaagcgagaaagttaaaagaattgacggaagggcaccaccaggcgtgga<br>gcttgcggcttaatttgactcaacacggggaaactcactagtttaagacaagagtaggattga<br>cagattaatagctattcttgatttcttggatggtgatgcatggccgtttttagttcgtgaatatgat<br>ttgtctggttaattccgataacgaacgagatcttaacctgctaattagcggcgagtacactatat<br>tcttatttgaaattgaacataggtaactatacatttattcagtaatcaaattaggatatattattaaa<br>atatccttttccctgttctactaataatttgtttttactctatttctctcttcttttaagaatgtacttgct<br>tgattgaaaagcttcttagaggaacattgtgtgtctaacacaaggaagtttaaggcaacaaca<br>ggtctgtgatgtccttagatgaactaggctgcacgcgtgctacactgatatatataacgagtttt<br>taaaaat | GenBank Accession No: JQ627151.1 *Plasmodium falciparum* isolate SF3 18S ribosomal RNA gene, partial sequence |
| 75 | gaagtaggactttggttctattt | Non-T7 primer |
| 76 | atgaagtaggactttggttct | Non-T7 primer |
| 77 | aacctggttgatcctgccagtagtcatatgcttgtcttaaagattaagccatgcatgtctaagta<br>caaactttttacggtgaaactgcgaatggctcattacaacagttatagtttcttggtattcgtttt<br>ccatggataaccgtgctaattgtagggctaatacaagttcgaggccttttggcggcgtttatta<br>gttctataaccacccttttggttttcggtgattcataataaactcgcgaatcgcaatttattgcgat<br>ggaccattcaagtttctgacccatcagcttgacggtagggtattggcctaccgaggcagcaa<br>cgggtaacggggaattagggttcgattccggagagggagcctgagaaacggctaccacat<br>ccaaggaaggcagcaggcgcgcaaattacccaatcctgacacagggaggtagtgacaag<br>aaataacaatacagggcaattgtcttgtaattggaatgatggtgacctaaaccctcaccagag<br>taacaattggagggcaagtctggtgccagcagccgcggtaattccagctccaatagcgtata<br>ttaaacttgttgcagttaaaaagctcgtagttgaatttctgcgttatcgagttattgactcttgtctt<br>taatcgatttcgcttttgggatttatcccttttttactttgagaaaattagagtgtttcaagcagacttt<br>tgtcttgaatacttcagcatggaataatagagtaggactttggttctattttgttggtttttgaacct<br>tagtaatggttaataggaacggttgggggcattcgtatttaactgtcagaggtgaaattcttag<br>atttgttaaagacgaactactgcgaaagcatttgccaaggacgtttccattaatcaagaacga<br>aagttaggggatcgaagacgatcagataccgtcgtagtcctaaccataaactatgccgacta<br>gggattggaggtcgtcatttttccgactccttcagcaccttgagagaaatcaaagtctttgggtt<br>ctgggggagtatggtcgcaaggctgaaacttaaaggaattgacggaagggcaccacca<br>ggcgtggagcctgcggcttaatttgactcaacacggggaaactcaccaggtccagacaatg<br>ttaggattgacagattgatagctctttgattctttgggtggtggtgcatggccgttcttagttg<br>gtggagtgatttgtctggttaattccgttaacgaacgagaccttaacctgctaactagtacccg<br>taaaaaggttcgtccgttacggtttgcttcttagagggactttgcggctctaagccgcaagga<br>agtttaaggcaataacaggtctgtgatgcccttagatgtcctgggctgcacgcgcgctacact<br>gatgcattcatcgagtttaatcctgtcccgaaagggctgggtaatctttagtatgcatcgtgac<br>ggggattgatttttgcaattctaaatcatgaacgaggaatgcctagtatgcgcaagtcatcagc<br>ttgtgcagattacgtccctgccctttgtacacaccgcccgtcgctcctaccgatcgagtgatcc<br>ggtgaattattcggaccgtggcttttccgattcgtcggttttgcctagggaagtctcgtgaacct<br>tatcacttaaaggaaggagaagtcgtaacaaggtttccgtaggtgaacctgcagaaggatca<br>agc | GenBank Accession No: AY046575.1 *Babesia* sp. EU1 clone BAB20 18S ribosomal RNA gene, complete sequence |
| 78 | gyygccycgguaggccaauacccuaccguccaaagcugaur | |
| 79 | gyygccycggtaggccaataccctaccgtccaaagctgatr | |

-continued

| SEQ ID NO. | Sequence (5' to 3') | Comments |
|---|---|---|
| 80 | aatttaatacgactcactatagggagaggcaaatgctttcgcagtagttngtctttaaca | T7 promoter primer, wherein "n" means a or g or c or t/u, or unknown, or other (WIPO Standard ST.25 (1998), Appendix 2, Table 1) |
| 81 | ggcaaatgctttcgcagtagttngtctttaaca | SEQ ID NO: 80 without promoter sequence, wherein "n" means a or g or c or t/u, or unknown, or other (WIPO Standard ST.25 (1998), Appendix 2, Table 1) |
| 82 | aatttaatacgactcactatagggagaggcaaatgctttcgcagtagttigtcttaaca | T7 promoter primer. "i" means inosine. |
| 83 | ggcaaatgctttcgcagtagttigtctttaaca | SEQ ID NO: 82 without promoter sequence. "i" means inosine. |
| 84 | gcggtaattccagctccaatag | Non-T7 primer |
| 85 | cttgaatactncagca | Non-T7 primer, wherein "n" means a or g or c or t/u, or unknown, or other (WIPO Standard ST.25 (1998), Appendix 2, Table 1) |
| 86 | cttgaatacticagca | Non-T7 primer. "i" means inosine. |
| 87 | aaagacuuugauuucucucaaggtttaaaaaaaaaaaaaaaaaaaaaaaaaaaaaa | Target capture |
| 88 | aaagacuuugauuucucucaagg | SEQ ID NO: 87 without capture tail sequence |
| 89 | caagaaagagcuaucaaucugucaaucctttaaaaaaaaaaaaaaaaaaaaaaaaaaaaa aa | Target capture |
| 90 | caagaaagagcuaucaaucugucaaucc | SEQ ID NO: 89 without capture tail sequence |
| 91 | aguaggacuuugguuct | Probe |
| 92 | aguaggacuuugguuc | Probe |
| 93 | aguaggacuauugguuc | Probe |
| 94 | aguaggacxuugguuc | Probe, wherein "x" means (i) u; or (ii) ua |

-continued

| SEQ ID NO. | Sequence (5' to 3') | Comments |
|---|---|---|
| 95 | actttgagaaaaytagagtgtttcaaacaggccatttgccttgaatactncagcatggaataat<br>gaagtaggactttggttctattttgttggtt | "n" means a or g or c or t/u, or unknown, or other (WIPO Standard ST.25 (1998), Appendix 2, Table 1) |
| 96 | ggcaaatgctttcgcagtagttngtctttaacaaatctaagaatttcacctctgacagttaaata<br>cgaatgcccccaa | "n" means a or g or c or t/u, or unknown, or other (WIPO Standard ST.25 (1998), Appendix 2, Table 1) |
| 97 | ggcaaatgctttcgcagtagttngtctttaacaaatc | "n" means a or g or c or t/u, or unknown, or other (WIPO Standard ST.25 (1998), Appendix 2, Table 1) |
| 98 | aguaggacuauugguucu | Probe |
| 99 | aguaggacxuugguucu | Probe, wherein "x" means (i) u; or (ii) ua |
| 100 | GGGCGAAUUGGGUACCGGGCCCCCCCUCGAGGUCGAC<br>GGUAUCGAUAAGCUUGAUAUCGAAUUCCUGCAGCCCG<br>GGGGAUCCAACCUGGUUGAUCCUGCCAGUAGUCAUAU<br>GCUUGUCUUAAAGAUUAAGCCAUGCAUGUCUAAGUAC<br>AAACUUUUUACGGUGAAACUGCGAAUGGCUCAUUACA<br>ACAGUUAUAGUUUCUUUGGUAUUCGUUUUCCAUGGA<br>UAACCGUGCUAAUUGUAGGGCUAAUACAAGUUCGAG<br>GCCUUUUGGCGGCGUUUAUUAGUUCUAUAACCACCCU<br>UUUGGUUUUCGGUGAUUCAUAAUAAACUCGCGAAUC<br>GCAAUUUAUUGCGAUGGACCAUUCAAGUUUCUGACCC<br>AUCAGCUUGACGGUAGGGUAUUGGCCUACCGAGGCAG<br>CAACGGGUAACGGGGAAUUAGGGUUCGAUUCCGGAG<br>AGGGAGCCUGAGAAACGGCUACCACAUCCAAGGAAGG<br>CAGCAGGCGCGCAAAUUACCCAAUCCUGACACAGGGA<br>GGUAGUGACAAGAAAUAACAAUACAGGGCAAUUGUC<br>UUGUAAUUGGAAUGAUGGUGACCUAAACCCUCACCAG<br>AGUAACAAUUGGAGGGCAAGUCUGGUGCCAGCAGCCG<br>CGGUAAUUCCAGCUCCAAUAGCGUAUAUUAAACUUGU<br>UGCAGUUAAAAAGCUCGUAGUUGAAUUUCUGCGUUA<br>UCGAGUUAUUGACUCUUGUCUUUAAUCGAUUUCGCUU<br>UUGGGAUUUAUCCCUUUUUACUUUGAGAAAAUUAGA<br>GUGUUUCAAGCAGACUUUUGUCUUGAAUACUUCAGCA<br>UGGAAUAAUAGAGUAGGACUUUGGUUCUAUUUUGUU<br>GGUUUUUGAACCUUAGUAAUGGUUAAUAGGAACGGU<br>UGGGGGCAUUCGUAUUUAACUGUCAGAGGUGAAAUU<br>CUUAGAUUUGUUAAAGACGAACUACUGCGAAAGCAU<br>UUGCCAAGGACGUUUCCAUUAAUCAAGAACGAAAGUU<br>AGGGGAUCGAAGACGAUCAGAUACCGUCGUAGUCCUA<br>ACCAUAAACUAUGCCGACUAGGGAUUGGAGGUCGUCA<br>UUUUUCCGACUCCUUCAGCACCUUGAGAGAAAUCAAA<br>GUCUUUGGGUUCUGGGGGGAGUAUGGUCGCAAGGCU<br>GAAACUUAAAGGAAUUGACGGAAGGGCACCACCAGGC<br>GUGGAGCCUGCGGCUUAAUUUGACUCAACACGGGGAA<br>ACUCACCAGGUCCAGACAAUGUUAGGAUUGACAGAUU<br>GAUAGCUCUUUCUUGAUUCUUUGGGUGGUGCGGCC | *B. venatorum* IVT |
| 101 | ctttcgcagtagttngtctttaac | Wherein "n" means a or g or c or t/u, or unknown, or other (WIPO Standard ST.25 (1998), Appendix 2, Table 1). |

The invention claimed is:

1. A method for specifically detecting *Babesia* species nucleic acid in a sample, said method comprising:

(1) contacting a sample, said sample suspected of containing *Babesia* species nucleic acid, with at least two oligomers for amplifying a target region of a *Babesia* species target nucleic acid, wherein the at least two amplification oligomers comprise:

(a) a first amplification oligomer comprising a first target-hybridizing sequence that consists of SEQ ID NO:8; and (b) a second amplification oligomer comprising a second target-hybridizing sequence that consists of SEQ ID NO:34;

(2) performing an in vitro nucleic acid amplification reaction, wherein any *Babesia* target nucleic acid present in said sample is used as a template for generating an amplification product; and, (3) detecting the presence or absence of the amplification product, thereby indicating the presence or absence of *Babesia* species target nucleic acid in said sample.

2. The method of claim 1, wherein the first amplification oligomer is a promoter primer or promoter provider further comprising a promoter sequence located 5' to the first target-hybridizing sequence.

3. The method of claim 2, wherein the promoter sequence is a T7 promoter sequence.

4. The method of claim 3, wherein the first amplification oligomer nucleotide sequence consists of SEQ ID NO:7.

5. The method of claim 1, further comprising purifying the target nucleic acid from other components in the sample before step (1), wherein the purifying step comprises contacting the sample with at least one capture probe oligomer, wherein the at least one capture probe oligomer comprises a target-hybridizing sequence covalently attached to a sequence or moiety that binds to an immobilized probe, wherein said target-hybridizing sequence consists of SEQ ID NO:44, SEQ ID NO:88, or SEQ ID NO:90.

6. The method of claim 5, wherein the capture probe oligomer sequence comprises or consists of SEQ ID NO:43, SEQ ID NO:87, or SEQ ID NO:89.

7. The method of claim 1, wherein the detecting step (3) comprises contacting said in vitro nucleic acid amplification reaction with a detection probe oligomer configured to specifically hybridize to the amplification product under conditions whereby the presence or absence of the amplification product is determined, thereby indicating the presence or absence of *Babesia* species in said sample.

8. The method of claim 7, wherein the detection probe oligomer comprises a detection probe target-hybridizing sequence consisting of the sequence selected from the group consisting of: SEQ ID NO:37, SEQ ID NO:42, SEQ ID NO:91, SEQ ID NO:92, SEQ ID NO:93, and combinations thereof.

9. The method of claim 8, wherein the detection probe oligomer comprises a 2' methoxy modification on at least one nucleotide residue member of the nucleotide sequence.

10. The method of claim 8, wherein the detection probe comprises a chemiluminescent label or a fluorescent label.

11. The method of claim 8, wherein the detection probe comprises a fluorescent label and a quencher.

12. The method of claim 1, wherein the at least two amplification oligomers further comprise:

(a) a third amplification oligomer comprising a third target-hybridizing sequence that consists of SEQ ID NO:83;

(b) a fourth amplification oligomer comprising a fourth target-hybridizing sequence that consists of SEQ ID NO:84; and, (c) a fifth amplification oligomer comprising a fifth target-hybridizing sequence that consists of SEQ ID NO:86.

13. The method of claim 12, further comprising purifying the target nucleic acid from other components in the sample before step (1), wherein the purifying step comprises contacting the sample with at least one capture probe oligomer, wherein the at least one capture probe oligomer comprises a target-hybridizing sequence covalently attached to a sequence or moiety that binds to an immobilized probe, wherein said target-hybridizing sequence consists of SEQ ID NO:44, SEQ ID NO:88, or SEQ ID NO:90.

14. The method of claim 1, wherein the detecting step (3) comprises contacting said in vitro nucleic acid amplification reaction with a detection probe oligomer configured to specifically hybridize to the amplification product under conditions whereby the presence or absence of the amplification product is determined, thereby indicating the presence or absence of *Babesia* species in said sample, wherein the detection probe oligomer comprises a detection probe target-hybridizing sequence consisting of a sequence selected from the group consisting of SEQ ID NO:91, SEQ ID NO:92, and SEQ ID NO:93.

* * * * *

UNITED STATES PATENT AND TRADEMARK OFFICE

CERTIFICATE OF CORRECTION

PATENT NO. : 11,667,978 B2
APPLICATION NO. : 16/611806
DATED : June 6, 2023
INVENTOR(S) : Vanessa Bres et al.

It is certified that error appears in the above-identified patent and that said Letters Patent is hereby corrected as shown below:

In the Specification

1. In Column 5, Line 61, delete "(1)" and insert -- (f) --, therefor.
2. In Column 9, Line 4, delete "(1)" and insert -- (f) --, therefor.
3. In Column 12, Line 50, delete "deoxygaunosine," and insert -- deoxyguanosine, --, therefor.
4. In Column 15, Line 29, delete "refer" and insert -- to refer --, therefor.
5. In Column 16, Line 64, delete "that the" and insert -- the --, therefor.
6. In Column 22, Line 45, delete "used" and insert -- used as --, therefor.
7. In Column 23, Line 45, delete "(1)" and insert -- (f) --, therefor.
8. In Column 24, Line 50, delete "(1)" and insert -- (f) --, therefor.
9. In Column 41, Line 21, delete "change" and insert -- change. --, therefor.
10. In Column 41, Line 24, delete "(e.g." and insert -- (e.g., --, therefor.
11. In Column 43, Line 19, delete "Chim" and insert -- Chim. --, therefor.
12. In Column 45, Line 40, delete "probe]" and insert -- probe]: --, therefor.
13. In Column 45, Line 66, delete "a the" and insert -- a --, therefor.
14. In Column 46, Line 5, delete "sequence]" and insert -- sequence]: --, therefor.
15. In Column 48, Line 47, delete "mM at 37C" and insert -- min at 37° C. --, therefor.
16. In Column 48, Line 50, delete "37C" and insert -- 37° C. --, therefor.
17. In Column 49, Line 9, delete "specifically" and insert -- specific --, therefor.
18. In Column 49, Line 53, delete "completed," and insert -- was completed, --, therefor.
19. In Column 50, Line 7, delete "on to" and insert -- onto --, therefor.
20. In Column 50, Line 23, delete "NO" and insert -- NO: --, therefor.
21. In Column 52, Line 45, delete "1a." and insert -- 1a --, therefor.
22. In Column 53, Line 2, delete "1a." and insert -- 1a --, therefor.
23. In Column 53, Line 6, delete "3,223" and insert -- 3,228 --, therefor.
24. In Column 53, Line 38, delete "1,842,523" and insert -- 1,842,528 --, therefor.
25. In Column 54, Table 5, Line 6, delete "2,273,506" and insert -- 2,272,506 --, therefor.
26. In Column 55, Line 12, delete "3,298" and insert -- 1,298 --, therefor.
27. In Column 55, Line 19, delete "543,761" and insert -- 548,761 --, therefor.
28. In Column 55, Line 24, delete "1,724" and insert -- 1,734 --, therefor.

Signed and Sealed this
Seventeenth Day of October, 2023

Katherine Kelly Vidal

Katherine Kelly Vidal
*Director of the United States Patent and Trademark Office*

29. In Column 57, Line 37, delete “1,7459” and insert -- 1,759 --, therefor.
30. In Column 57, Line 37, delete “1,830” and insert -- 1,630 --, therefor.
31. In Column 57, Line 37, delete “3,258” and insert -- 3,256 --, therefor.
32. In Column 57, Line 52, delete “397,486” and insert -- 397,466 --, therefor.
33. In Column 57, Line 53, delete “88,246” and insert -- 63,246 --, therefor.
34. In Column 58, Line 64, delete “and were” and insert -- were --, therefor.
35. In Column 63, Line 3, delete “Non T7” and insert -- Non-T7 --, therefor.
36. In Column 67, Line 60, delete “Others” and insert -- Other --, therefor.
37. In Column 67, Line 62, delete “(Condition” and insert -- (Conditions --, therefor.
38. In Column 82, Line 25, delete “B. ventorum” and insert -- B. venatorum --, therefor.
39. In Column 86, Line 8, delete “49)” and insert -- 49 --, therefor.

In the Claims

40. In Column 147, Line 18, in Claim 1, delete “and,” and insert -- and --, therefor.
41. In Column 148, Line 23, in Claim 12, delete “and,” and insert -- and --, therefor.

SEQUENCE LISTING

<160> NUMBER OF SEQ ID NOS: 101

<210> SEQ ID NO 1
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 1
aatttaatac gactcactat agggagattc acctctgaca gttaaatacg aa        52

<210> SEQ ID NO 2
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 2
ttcacctctg acagttaaat acgaa                                      25

<210> SEQ ID NO 3
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 3
aatttaatac gactcactat agggagaaca gttaaatacg aatgccccca a         51

<210> SEQ ID NO 4
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 4
acagttaaat acgaatgccc ccaa                                       24

<210> SEQ ID NO 5
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 5
aatttaatac gactcactat agggagattc acctctgaca gttaaatac            49

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
ttcacctctg acagttaaat ac 22

<210> SEQ ID NO 7
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 7
aatttaatac gactcactat agggagagct ttcgcagtag ttcgtcttta acaaatc 57

<210> SEQ ID NO 8
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 8
gctttcgcag tagttcgtct ttaacaaatc 30

<210> SEQ ID NO 9
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 9
aatttaatac gactcactat agggagactt tcgcagtagt tcgtctttaa c 51

<210> SEQ ID NO 10
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 10
ctttcgcagt agttcgtctt taac 24

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
cttgaatact acagcatgga 20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
actacagcat ggaataatga 20

<210> SEQ ID NO 13
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 13
cttgaatact acagcatgga ataa 24

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
acttcagcat ggaataatga 20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
cttgaatact tcagcatgga 20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: variation
<222> LOCATION: (4)..(4)
<223> OTHER INFORMATION: "n" means a or g or c or t/u, or unknown, or
other (WIPO Standard ST.25 (1998), Appendix 2, Table 1)
<220> FEATURE:
<221> NAME/KEY: misc_feature
<222> LOCATION: (4)..(4)
<223> OTHER INFORMATION: n is a, c, g, or t

<400> SEQUENCE: 16
actncagcat ggaataatga 20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
actwcagcat ggaataatga 20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: variation
<222> LOCATION: (11)..(11)

<223> OTHER INFORMATION: "n" means a or g or c or t/u, or unknown, or
      other (WIPO Standard ST.25 (1998), Appendix 2, Table 1)
<220> FEATURE:
<221> NAME/KEY: misc_feature
<222> LOCATION: (11)..(11)
<223> OTHER INFORMATION: n is a, c, g, or t

<400> SEQUENCE: 18
cttgaatact ncagcatgga 20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
cttgaatact wcagcatgga 20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
actttgagaa aactagagtg 20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
agaaaactag agtgtttcaa 20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
ataatgaagt aggactttgg 20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
aggactttgg ttctattttg 20

<210> SEQ ID NO 24
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 24
ggttctattt tgttggtt 18

<210> SEQ ID NO 25
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 25
tggttctatt ttgttgg 17

<210> SEQ ID NO 26
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 26
ggaataatga agtaggactt t 21

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
atggaataat gaagtaggac 20

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 28
atggaataat gaagtagg 18

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 29
gcatggaata atgaagtag 19

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
tacagcatgg aataatgaag 20

<210> SEQ ID NO 31
<211> LENGTH: 20

<212> TYPE: DNA
<213> ORGANISM: Artificial Sequence
<220> FEATURE:
<223> OTHER INFORMATION: Synthetic Oligonucleotide

<400> SEQUENCE: 31
tactacagca tggaataatg 20

<210> SEQ ID NO 32
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 32
agaaaactag agtgtttca 19

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
agaaaattag agtgtttcaa 20

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 34
gagaaaacta gagtgtttca a 21

<210> SEQ ID NO 35
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 35
gagaaaatta gagtgtttca a 21

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tgagaaaact agagtgtttc 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
ugaaguagga cuuugguucu 20

<210> SEQ ID NO 38
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 38
uaaugguuaa uaggagcagu ug 22

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
aguaaugguu aauaggagca 20

<210> SEQ ID NO 40
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 40
ggacuuuggu ucuauuuugu ugg 23

<210> SEQ ID NO 41
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 41
aaugguuaau aggagcaguu ggggg 25

<210> SEQ ID NO 42
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 42
aguaggacuu ugguucu 17

<210> SEQ ID NO 43
<211> LENGTH: 54
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (22)..(54)
<223> OTHER INFORMATION: capture sequence

<400> SEQUENCE: 43
uaggccaaua cccuaccguc ctttaaaaaa aaaaaaaaaa aaaaaaaaaa aaaa 54

<210> SEQ ID NO 44
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 44
uaggccaaua cccuaccguc c 21

<210> SEQ ID NO 45
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 45
atggaataat gaagtag 17

<210> SEQ ID NO 46
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 46
agaaaactag agtg 14

<210> SEQ ID NO 47
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 47
agaaaattag agtg 14

<210> SEQ ID NO 48
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 48
agaaaaytag agtg 14

<210> SEQ ID NO 49
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 49
agaaaactag agtgtttc 18

<210> SEQ ID NO 50
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 50
agaaaattag agtgtttc 18

<210> SEQ ID NO 51
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 51
agaaaaytag agtgtttc 18

<210> SEQ ID NO 52
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 52
tactacagca tggaataa 18

<210> SEQ ID NO 53
<211> LENGTH: 13
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: variation
<222> LOCATION: (4)..(4)
<223> OTHER INFORMATION: "n" means a or g or c or t/u, or unknown, or other (WIPO Standard ST.25 (1998), Appendix 2, Table 1)
<220> FEATURE:
<221> NAME/KEY: misc_feature
<222> LOCATION: (4)..(4)
<223> OTHER INFORMATION: n is a, c, g, or t

<400> SEQUENCE: 53
actncagcat gga 13

<210> SEQ ID NO 54
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 54
actwcagcat gga 13

<210> SEQ ID NO 55
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 55
actacagcat gga 13

<210> SEQ ID NO 56
<211> LENGTH: 12
<212> TYPE: DNA
<213> ORGANISM: Artificial Sequence
<220> FEATURE:

<223> OTHER INFORMATION: Synthetic Oligonucleotide

<400> SEQUENCE: 56
gtatttaact gt 12

<210> SEQ ID NO 57
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 57
gtatttaact gtcagaggtg aa 22

<210> SEQ ID NO 58
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 58
aatttaatac gactcactat agggaga 27

<210> SEQ ID NO 59
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 59
aguaggacuu ugguucu 17

<210> SEQ ID NO 60
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 60
uaaugguuaa uaggagca 18

<210> SEQ ID NO 61
<211> LENGTH: 1206
<212> TYPE: DNA
<213> ORGANISM: Artificial Sequence
<220> FEATURE:
<223> OTHER INFORMATION: B. microti In Vitro Transcript

<400> SEQUENCE: 61
gggcgaauug gguaccgggc ccccccucga ggucgacgcu uaguauaagc uuuuauacag 60
cgaaacugcg aauggcucau uaaaacaguu auaguuuauu ugauguucgu uuuacaugga 120
uaaccguggu aauucuaggg cuaauacaug cucgaggcgc guuuucgcgu ggcguuuauu 180
agacuuuaac caacccuucg gguaaucggu gauucauaau aaauuagcga aucgcauggc 240
uuugccggcg auguaucauu caaguuucug accuaucagc uuuggacggu aggguauugg 300
ccuaccgggg cgacgacggg ugacggggaa uuggggguucg auuccggaga gggagccuga 360
gaaacggcua ccacaucuaa ggaaggcagc aggcgcgcaa auuacccaau ccugacacag 420
ggagguagug acaagaaaua acaauacagg gcuuaaaguc uuguaauugg aaugauggga 480
aucuaaaccc uucccagagu aucaauugga gggcaagucu ggugccagca gccgcgguaa 540
uuccagcucc aauagcguau auuaaaguug uugcaguuaa gaagcucgua guugaauuuc 600
ugccuuguca uuaaucucgc uuccgagcgu uuuuuuauug acuuggcauc uucuggauuu 660
ggugccuucg gguacuauuu uccaggauuu acuuugagaa aacuagagug uuucaaacag 720
gcauucgccu ugaauacuac agcauggaau aaugaaguag gacuuugguu cuauuuuguu 780
gguuauugag ccagaguaau gguuaauagg agcaguuggg ggcauucgua uuuaacuguc 840
agaggugaaa uucuuagauu uguuaaagac gaacuacugc gaaagcauuu gccaaggaug 900
uuuucauuaa ucaagaacga aaguuagggg aucgaagacg aucagauacc gucguagucc 960
uaaccauaaa cuaugccgac uagagauugg aggucgucag uuuaaacgac uccuucagca 1020
ccuugagaga aaucaaaguc uuuggguucu ggggggagua uggucgcaag ucugaaacuu 1080
aaaggaauug acggaagggc accaccaggc guggagccug cggcuuaauu ugacucaaca 1140
cgggaaaccu caccaggucc agacauagag aggauugaca gauugauagc ucuuucuuga 1200
ugaauu 1206

<210> SEQ ID NO 62
<211> LENGTH: 1282
<212> TYPE: DNA
<213> ORGANISM: Artificial Sequence
<220> FEATURE:
<223> OTHER INFORMATION: B. divergens In Vitro Transcript

<400> SEQUENCE: 62
gggcgaauug gguaccgggc ccccccucga ggucgacggu aucgauaagc uugauaucga 60
auuccugcag cccgggggau ccaaccuggu ugauccugcc aguagucaua ugcuugucuu 120
aaagauuaag ccaugcaugu cuaaguacaa acuuuuuacg gugaaacugc gaauggcuca 180
uuacaacagu uauaguuucu uugguauucg uuuuccaugg auaaccgugc uaauuguagg 240
gcuaauacaa guucgaggcc uuuuggcggc guuuauuagu ucuaaaacca ucccuuuugg 300
uuuucgguga uucauaauaa acuugcgaau cgcaauuuuu ugcgauggac cauucaaguu 360
ucugacccau cagcuugacg guaggguauu ggccuaccga ggcagcaacg gguaacgggg 420
aauuaggguu cgauuccgga gagggagccu gagaaacggc uaccacaucc aaggaaggca 480
gcaggcgcgc aaauuaccca auccugacac agggagguag ugacaagaaa uaacaauaca 540
gggcaauugu cuuguaauug gaaugauggu gaccuaaacc cucaccagag uaacaauugg 600
agggcaaguc uggugccagc agccgcggua auuccagcuc caauagcgua uauuaaacuu 660
guugcaguua aaaagcucgu aguugaauuu uugcguggug uuaauauuga cuaaugucga 720
gauugcacuu cgcuuuuggg auuuaucccu uuuuacuuug agaaaauuag aguguuucaa 780
gcagacuuuu gucuugaaua cuucagcaug gaauaauaga guaggacuuu gguucuauuu 840
uguugguuug ugaaccuuag uaaugguuaa uaggaacggu ugggggcauu cguauuuaac 900
ugucagaggu gaaauucuua gauuuguuaa agacgaacua cugcgaaagc auuugccaag 960
gacguuuuca uuaaucaaga acgaaaguua ggggaucgaa gacgaucaga uaccgucgua 1020
guccuaacca uaaacuaugc cgacuaggga uuggaggucg ucauuuuucc gacuccuuca 1080
gcaccuugag agaaaucaaa gucuuugggu ucuggggggga guauggucgc aaggcugaaa 1140
cuuaaaggaa uugacggaag ggcaccacca ggcguggagc cugcggcuua auuugacuca 1200
acacggggaa acucaccagg uccagacaau guuaggauug acagauugau agcucuuucu 1260
ugauucuuug gguggugcgg cc 1282

<210> SEQ ID NO 63
<211> LENGTH: 1251
<212> TYPE: DNA
<213> ORGANISM: Artificial Sequence
<220> FEATURE:
<223> OTHER INFORMATION: B. duncani In Vitro Transcript

<400> SEQUENCE: 63
gggcgaauug gguaccgggc ccccccucga ggucgacguu gauccugcca guagucauau 60
gcuugucuua aagauuaagc caugcauguc uaaguauaaa cuuuuauaug gugaaacugc 120
gaauggcuca uuacaacagu uauaguuuau uugaaagucg uuuuuacaug gauaaccgug 180
cuaauuguag ggcuaauaca ugcucgaggc cuuggcuccu gucuuggcug cguuuauuag 240
acucgaaacc uucccgcuug cgguacucgg ugauucauaa uaaauuugcg aaucgcaugg 300
cuuuugccgg cgaugguuca uucaaguuuc ugaccuauca gcuuuggacg guaggguauu 360
ggccuaccgg ggcagcgacg gguaacgggg aauuaggguu cgauuccgga gagggagccu 420
gagaaacggc uaccacaucu aaggaaggca gcaggcgcgc aaauuaccca auacggacac 480
cgugagguag ugacaagaaa uaacaauaca gggcuuaaag cuuuguaauu ggaaugaugg 540
gaauccaaac cccuuccaga guaucaauug gagggcaagu cuggugccag cagccgcggu 600
aauuccagcu ccaauagcgu auauuaaacu uguugcaguu aaaaagcucg uaguugaacu 660
ucugccgcuu ggccuuucgu uccccuuggg guuucguucg ccugguggcu uaccucuggc 720
ggugguucuc cauuugccag uuuuacuuug agaaaauuag aguguuucaa gcaggcuuuu 780
gccuugaaua cuucagcaug gaauaauaaa guaggacuuu gguucuauuu uguugguuuc 840
aggaccaaag uaaugguuaa uaggaacagu ugggggcauu cguauuuaac ugucagaggu 900
gaaauucuua gauuuguuaa agacgaacua cugcgaaagc auuugccaag gauguuuuca 960
uuaaucaaga acgaaaguua ggggcucgaa gacgaucaga uaccgucgua guccuaacua 1020
uaaacuaugc cgacuagaga uuggaggucg ucauuuuaaa cgacuccuuc agcaccuuga 1080
gagaaaucaa agucuuuggg uucugggggg aguauggucg caaggcugaa acuuaaagga 1140
auugacggaa gggcaccacc aggcguggag ccugcggcuu aauuugacuc aacacgggga 1200
accucaccag guccagacau aguuaggauu gacagauuga uagcucgaau u 1251

<210> SEQ ID NO 64
<211> LENGTH: 1387
<212> TYPE: DNA
<213> ORGANISM: Artificial Sequence
<220> FEATURE:
<223> OTHER INFORMATION: P. falciparum In Vitro Transcript

<400> SEQUENCE: 64
gggcgaauug gguaccguag aaacugcgaa cggcucauua aaacaguuau agucuacuug 60
acauuuuuau uauaaggaua acuacggaaa agcuguagcu aauacuugcu uuauuauccu 120
uugauuuuua ucuuuggaua aguauuuguu aggccuuaua agaaaaaagu uauuaacuua 180
aggaauuaua acaaagaagu aacacguaau aaauuuauuu uauuuagugu guaucaaucg 240
aguuucugac cuaucagcuu uugauguuag gguauuggcc uaacauggcu augacgggua 300
acggggaauu agaguucgau uccggagagg gagccugaga aauagcuacc acaucuaagg 360
aaggcagcag gcgcguaaau uacccaauuc uaaaaaagag agguagugac aagaaauaac 420
aaugcaaggc caauuuuugg uuuuguaauu ggaauggugg gaauuuaaaa ccuucccaga 480
guaacaauug gagggcaagu cuggugccag cagccgcggu aauuccagcu ccaauagcgu 540
auauuaaaau uguugcaguu aaaacgcucg uaguugaauu ucaaagaauc gauauuuuau 600
uguaacuauu cuaggggaac uauuuuaggu uuucgcuuua auacgcuucc ucuauuauua 660
uguucuuuaa auaacaaaga uucuuuuuaa aaucccccacu uuugcuuuuu uggggaauuu 720
guuacuuuga auaaaauuaga ggugucaaag caaacaguua aagcauuuac uguguuugaa 780
uacuauagca uggaauaaca aaauugaaca agcuaaaauu uuuuguucuu uuuucuuauu 840
uuggcuuagu uacgauuaau aggaguagcu uggggacauu cguauucaga ugucagaggu 900
gaaauucuua gauuuucugg agacgaacaa cugcgaaagc auuugucuaa aauacuucca 960
uuaaucaaga acgaaaguua agggagugaa gacgaucaga uaccgucgua aucuuaacca 1020
uaaacuaugc cgacuaggug uuggaugaaa guguuaaaaa uaaaagucau cuuucuaggu 1080
gacuuuuaga uugcuuccuu caguaccuua ugagaaauca aagucuuugg guucuggggc 1140
gaguauucgc gcaagcgaga aaguuaaaag aauugacgga agggcaccac caggcgugga 1200
gcuugcggcu uaauuugacu caacacgggg aaacucacua guuuaagaca agaguaggau 1260
ugacagauua auagcucuuu cuugauuucu uggaugguga ugcauggccg uuuuuaguuc 1320
gugaauauga uuugucuggu uaauuccgau aacgaacgag aucggaucca cuaguucuag 1380
agcggcc 1387

<210> SEQ ID NO 65
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 65
ugaaguagga cuuugguucu auuuuguugg uuauugagcc agaguaaugg uuaauaggag 60
caguuggggg 70

<210> SEQ ID NO 66
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 66
ttcacctctg acagttaaat acgaatgccc ccaa 34

<210> SEQ ID NO 67
<211> LENGTH: 34
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: variation
<222> LOCATION: (5)..(5)
<223> OTHER INFORMATION: "n" means a or g or c or t/u, or unknown, or other (WIPO Standard ST.25 (1998), Appendix 2, Table 1)
<220> FEATURE:
<221> NAME/KEY: misc_feature
<222> LOCATION: (5)..(5)
<223> OTHER INFORMATION: n is a, c, g, or t

<400> SEQUENCE: 67
tactncagca tggaataatg aagtaggact ttgg 34

<210> SEQ ID NO 68
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: variation
<222> LOCATION: (11)..(11)
<223> OTHER INFORMATION: "n" means a or g or c or t/u, or unknown, or other (WIPO Standard ST.25 (1998), Appendix 2, Table 1)
<220> FEATURE:
<221> NAME/KEY: misc_feature
<222> LOCATION: (11)..(11)
<223> OTHER INFORMATION: n is a, c, g, or t

<400> SEQUENCE: 68
cttgaatact ncagcatgga ataatga 27

<210> SEQ ID NO 69
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 69
atggaataat g 11

<210> SEQ ID NO 70
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 70
actttgagaa aaytagagtg tttcaaa 27

<210> SEQ ID NO 71
<211> LENGTH: 1767
<212> TYPE: DNA
<213> ORGANISM: Babesia microti
<300> PUBLICATION INFORMATION:
<308> DATABASE ACCESSION NUMBER: AY693840.1
<309> DATABASE ENTRY DATE: 2004-09-05
<313> RELEVANT RESIDUES IN SEQ ID NO: (1)..(1767)

<400> SEQUENCE: 71
aacctggttg atcctgccag tagtcatatg cttgtcttaa agattaagcc atgcatgtct 60
tagtataagc ttttatacag cgaaactgcg aatggctcat taaaacagtt atagtttatt 120
tgatgttcgt tttacatgga taaccgtggt aattctaggg ctaatacatg ctcgaggcgc 180
gttttcgcgt ggcgtttatt agactttaac caacccttcg ggtaatcggt gattcataat 240
aaattagcga atcgcatggc tttgccggcg atgtatcatt caagtttctg acctatcagc 300
tttggacggt agggtattgg cctaccgggg cgacgacggg tgacggggaa ttggggttcg 360
attccggaga gggagcctga gaaacggcta ccacatctaa ggaaggcagc aggcgcgcaa 420
attacccaat cctgacacag ggaggtagtg acaagaaata acaatacagg gcttaaagtc 480
ttgtaattgg aatgatggga atctaaaccc ttcccagagt atcaattgga gggcaagtct 540
ggtgccagca gccgcggtaa ttccagctcc aatagcgtat attaaagttg ttgcagttaa 600
gaagctcgta gttgaatttc tgccttgtca ttaatctcgc ttccgagcgt ttttttattg 660
acttggcatc ttctggattt ggtgccttcg ggtactattt tccaggattt actttgagaa 720
aactagagtg tttcaaacag gcattcgcct tgaatactac agcatggaat aatgaagtag 780
gactttggtt ctattttgtt ggttattgag ccagagtaat ggttaatagg agcagttggg 840
ggcattcgta tttaactgtc agaggtgaaa ttcttagatt tgttaaagac gaactactgc 900
gaaagcattt gccaaggatg ttttcattaa tcaagaacga aagttagggg atcgaagacg 960
atcagatacc gtcgtagtcc taaccataaa ctatgccgac tagagattgg aggtcgtcag 1020
tttaaacgac tccttcagca ccttgagaga aatcaaagtc tttgggttct ggggggagta 1080
tggtcgcaag tctgaaactt aaaggaattg acggaagggc accaccaggc gtggagcctg 1140
cggcttaatt tgactcaaca cgggaaacct caccaggtcc agacatagag aggattgaca 1200
gattgatagc tctttcttga ttctatgggt ggtggtgcat ggccgttctt agttggtgga 1260
gtgatttgtc tggttaattc cgttaacgaa cgagacctta acctgctaaa ttaggatctg 1320
ggacaagctt tgctgttcca gtatcgcttc ttagagggac tttgcgttca taaaacgcaa 1380
ggaagtgtaa ggcaataaca ggtctgtgat gcccttagat gtcctgggct gcacgcgcgc 1440
tacactgatg cattcaacga gtttttcctt ggccgtcggg tccgggtaat cttacagtat 1500
gcatcgtgat ggggatagat tattgcaatt attaatcttg aacgaggaat gcctagtagg 1560
cgcgagtcat cagctcgtgc cgactacgtc cctgcccttt gtacacaccg cccgtcgctc 1620
ctaccgatcg agtgatccgg tgaattattc ggaccaagaa acgtggattc gtccttcgtt 1680
ttttggaaag ttttgtgaac cttatcactt aaaggaagga gaagtcgtaa caaggtttcc 1740
gtaggtgaac ctgcggaagg atcattc 1767

<210> SEQ ID NO 72
<211> LENGTH: 1728
<212> TYPE: DNA
<213> ORGANISM: Babesia divergens
<300> PUBLICATION INFORMATION:
<308> DATABASE ACCESSION NUMBER: AY789076.1
<309> DATABASE ENTRY DATE: 2004-11-17
<313> RELEVANT RESIDUES IN SEQ ID NO: (1)..(1728)

<400> SEQUENCE: 72
aacctggttg atcctgccag tagtcatatg cttgtcttaa agattaagcc atgcatgtct 60
aagtacaaac tttttacggt gaaactgcga atggctcatt acaacagtta tagtttcttt 120
ggtattcgtt ttccatggat aaccgtgcta attgtagggc taatacaagt tcgaggcctt 180
ttggcggcgt ttattagttc taaaaccatc ccttttggtt ttcggtgatt cataataaac 240
ttgcgaatcg caattttttg cgatggacca ttcaagtttc tgacccatca gcttgacggt 300
agggtattgg cctaccgagg cagcaacggg taacggggaa ttagggttcg attccggaga 360
gggagcctga gaaacggcta ccacatccaa ggaaggcagc aggcgcgcaa attacccaat 420
cctgacacag ggaggtagtg acaagaaata acaatacagg gcaattgtct tgtaattgga 480
atgatggtga cctaaaccct caccagagta acaattggag ggcaagtctg gtgccagcag 540
ccgcggtaat tccagctcca atagcgtata ttaaacttgt tgcagttaaa aagctcgtag 600
ttgaattttt gcgtggtgtt aatattgact aatgtcgaga ttgcacttcg cttttgggat 660
ttatcccttt ttactttgag aaaattagag tgtttcaagc agacttttgt cttgaatact 720
tcagcatgga ataatagagt aggactttgg ttctattttg ttggtttgtg aaccttagta 780
atggttaata ggaacggttg ggggcattcg tatttaactg tcagaggtga aattcttaga 840

```
tttgttaaag acgaactact gcgaaagcat ttgccaagga cgttttcatt aatcaagaac    900

gaaagttagg ggatcgaaga cgatcagata ccgtcgtagt cctaaccata aactatgccg    960

actagggatt ggaggtcgtc atttttccga ctccttcagc accttgagag aaatcaaagt   1020

ctttgggttc tgggggagt atggtcgcaa ggctgaaact taaaggaatt gacggaaggg   1080

caccaccagg cgtggagcct gcggcttaat ttgactcaac acggggaaac tcaccaggtc   1140

cagacaatgt taggattgac agattgatag ctctttcttg attctttggg tggtggtgca   1200

tggccgttct tagttggtgg agtgatttgt ctggttaatt ccgttaacga acgagacctt   1260

aacctgctaa ctagtgtccg taaaaaggtt cgtccgttac ggtttgcttc ttagagggac   1320

tttgcggctc taagccgcaa ggaagtttaa ggcaataaca ggtctgtgat gcccttagat   1380

gtcctgggct gcacgcgcgc tacactgatg cattcatcga gttttatccc ttcccgaaag   1440

ggctgggtaa tctttagtat gcatcgtgac ggggattgat tttgcaatt ctaaatcatg   1500

aacgaggaat gcctagtatg cgcaagtcat cagcttgtgc agattacgtc cctgcccttt   1560

gtacacaccg cccgtcgctc ctaccgatcg agtgatccgg tgaattattc ggaccgtggc   1620

ctttccgatt cgtcggcttg gcctagggaa gtcttgtgaa ccttatcact taaaggaagg   1680

agaagtcgta acaaggtttc cgtaggtgaa cctgcggaag gatcattc               1728
```

<210> SEQ ID NO 73
<211> LENGTH: 1742
<212> TYPE: DNA
<213> ORGANISM: Babesia strain WA1
<300> PUBLICATION INFORMATION:
<308> DATABASE ACCESSION NUMBER: AY027815.1
<309> DATABASE ENTRY DATE: 2001-03-02
<313> RELEVANT RESIDUES IN SEQ ID NO: (1)..(1742)

<400> SEQUENCE: 73

```
ccttggttga tcctgccagt agtcatatgc ttgtcttaag gattaagcca tgcatgtcta     60

agtataaact tttatatggt gaaactgcga atggctcatt acaacagtta tagtttattt    120

gaaagtcgtt tttacatgga taaccgtgct aattgtaggg ctaatacatg ctcgaggcct    180

tggcttctgt cttggctgcg tttattagac tcgaaacctt cccgcttgcg gtactcggtg    240

attcataata aatttgcgaa tcgcatggct tttgccggcg atggttcatt caagtttctg    300

acctatcagc tttggacggt agggtattgg cctaccgggg cagcgacggg taacggggaa    360

ttagggttcg attccggaga gggagcctga gaaacggcta ccacatctaa ggaaggcagc    420

aggcgcgcaa attacccaat acggacaccg tgaggtagtg acaagaaata acaatacagg    480

gctttaagct ttgtaattgg aatgatggga atccaaaccc cttccagagt atcaattgga    540

gggcaagtct ggtgccagca gccgcggtaa ttccagctcc aatagcgtat attaaacttg    600

ttgcagttaa aaagctcgta gttgaacttc tgccgcttgg cctttcgttc cccttggggt    660

ttcgttcgcc tggtggctta cctctggcgg tggttctcca tttgccagtt ttactttgag    720

aaaattagag tgtttcaagc aggcttttgc cttgaatact tcagcatgga ataataaagt    780

aggactttgg ttctattttg ttggtttcag gaccaaagta atggttaata ggaacagttg    840

ggggcattcg tatttaactg tcagaggtga aattcttaga tttgttaaag acgaactact    900

gcgaaagcat ttgccaagga tgttttcatt aatcaagaac gaaagttagg ggctcgaaga    960

cgatcagata ccgtcgtagt cctaactata aactatgccg actagagatt ggaggtcgtc   1020

attttaaacg actccttcag caccttgaga gaaatcaaag tctttgggtt ctgggggag   1080

tatggtcgca aggctgaaac ttaaaggaat tgacggaagg gcaccaccag gcgtggagcc   1140
```

tgcggcttaa tttgactcaa cacggggaac ctcaccaggt ccagacatag ttaggattga 1200
cagattgata gctctttctt gattctatgg gtagtggtgc atggccgttc ttagttggtg 1260
gagtgatttg tctggttaat tccgttaacg aacgagacct taacctgcta aatagcagct 1320
gagaataatc tcttgtttca gttttgcttc ttagagggac tttgcggtca taaatcgcaa 1380
ggaagtttaa ggcaataaca ggtctgtgat gcccttagat gtcctgggct gcacgcgcgc 1440
tacactgatg cattcatcga gttttatcct tgcccgaaag ggtttggtaa tctttagtat 1500
gcatcgtgat ggggattgat tattgcaatt attaatcatg aacgaggaat gcctagtagg 1560
cgcgagtcat cagctcgtgc cgactacgtc cctgcccttt gtacacaccg cccgtcgctc 1620
ctaccgatcg agtgatccgg tgaattattc ggaccgtgac gcttctaatt cgttagaaat 1680
gtctagggaa gttttgtgaa ccttatcact taaaggaagg agaagtcgta acaaggtttc 1740
cg 1742

<210> SEQ ID NO 74
<211> LENGTH: 1708
<212> TYPE: DNA
<213> ORGANISM: Plasmodium falciparum
<300> PUBLICATION INFORMATION:
<308> DATABASE ACCESSION NUMBER: JQ627151.1
<309> DATABASE ENTRY DATE: 2012-08-14
<313> RELEVANT RESIDUES IN SEQ ID NO: (1)..(1708)

<400> SEQUENCE: 74
tcaaagatta agccatgcaa gtgaaagtat atatatattt tatatgtaga aactgcgaac 60
ggctcattaa aacagttata gtctacttga catttttatt ataaggataa ctacggaaaa 120
gctgtagcta atacttgctt tattatcctt tgatttttat ctttggataa gtatttgtta 180
ggccttataa gaaaaaagtt attaacttaa ggaattataa caaagaagta acacgtaata 240
aatttatttt atttagtgtg tatcaatcga gtttctgacc tatcagcttt tgatgttagg 300
gtattggcct aacatggcta tgacgggtaa cggggaatta gagttcgatt ccggagaggg 360
agcctgagaa atagctacca catctaagga aggcagcagg cgcgtaaatt acccaattct 420
aaaaaagaga ggtagtgaca agaaataaca atgcaaggcc aatttttggt tttgtaattg 480
gaatggtggg aatttaaaac cttcccagag taacaattgg agggcaagtc tggtgccagc 540
agccgcggta attccagctc caatagcgta tattaaaatt gttgcagtta aaacgctcgt 600
agttgaattt caaagaatcg atattttatt gtaactattc taggggaact attttaggtt 660
ttcgctttaa tacgcttcct ctattattat gttctttaaa taacaaagat tctttttaaa 720
atccccactt ttgcttttgc ttttttgggg aatttgttac tttgaataaa ttagaggtgt 780
caaagcaaac agttaaagca tttactgtgt ttgaatacta tagcatggaa taacaaaatt 840
gaacaagcta aaatttttg ttcttttttc ttattttggc ttagttacga ttaataggag 900
tagcttgggg acattcgtat tcagatgtca gaggtgaaat tcttagattt tctggagacg 960
aacaactgcg aaagcatttg tctaaaatac ttccattaat caagaacgaa agttaaggga 1020
gtgaagacga tcagataccg tcgtaatctt aaccataaac tatgccgact aggtgttgga 1080
tgaaagtgtt aaaaataaaa gtcatctttc taggtgactt ttagattgct tccttcagta 1140
ccttatgaga aatcaaagtc tttgggttct ggggcgagta ttcgcgcaag cgagaaagtt 1200
aaaagaattg acggaagggc accaccaggc gtggagcttg cggcttaatt tgactcaaca 1260
cggggaaact cactagttta agacaagagt aggattgaca gattaatagc tctttcttga 1320

-continued

```
tttcttggat ggtgatgcat ggccgttttt agttcgtgaa tatgatttgt ctggttaatt   1380

ccgataacga acgagatctt aacctgctaa ttagcggcga gtacactata ttcttatttg   1440

aaattgaaca taggtaacta tacatttatt cagtaatcaa attaggatat ttttattaaa   1500

atatcctttt ccctgttcta ctaataattt gtttttttact ctatttctct cttcttttaa   1560

gaatgtactt gcttgattga aaagcttctt agaggaacat tgtgtgtcta acacaaggaa   1620

gtttaaggca acaacaggtc tgtgatgtcc ttagatgaac taggctgcac gcgtgctaca   1680

ctgatatata taacgagttt ttaaaaat                                        1708
```

<210> SEQ ID NO 75
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 75

```
gaagtaggac tttggttcta ttt                                              23
```

<210> SEQ ID NO 76
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 76

```
atgaagtagg actttggttc t                                                21
```

<210> SEQ ID NO 77
<211> LENGTH: 1727
<212> TYPE: DNA
<213> ORGANISM: Babesia sp. EU1 venatorum
<300> PUBLICATION INFORMATION:
<308> DATABASE ACCESSION NUMBER: AY046575.1
<309> DATABASE ENTRY DATE: 2003-07-09
<313> RELEVANT RESIDUES IN SEQ ID NO: (1)..(1727)

<400> SEQUENCE: 77

```
aacctggttg atcctgccag tagtcatatg cttgtcttaa agattaagcc atgcatgtct     60

aagtacaaac tttttacggt gaaactgcga atggctcatt acaacagtta tagtttcttt    120

ggtattcgtt ttccatggat aaccgtgcta attgtagggc taatacaagt tcgaggcctt    180

ttggcggcgt ttattagttc tataaccacc cttttggttt tcggtgattc ataataaact    240

cgcgaatcgc aatttattgc gatggaccat tcaagtttct gacccatcag cttgacggta    300

gggtattggc ctaccgaggc agcaacgggt aacggggaat tagggttcga ttccggagag    360

ggagcctgag aaacggctac cacatccaag gaaggcagca ggcgcgcaaa ttacccaatc    420

ctgacacagg gaggtagtga caagaaataa caatacaggg caattgtctt gtaattggaa    480

tgatggtgac ctaaaccctc accagagtaa caattggagg gcaagtctgg tgccagcagc    540

cgcggtaatt ccagctccaa tagcgtatat taaacttgtt gcagttaaaa agctcgtagt    600

tgaatttctg cgttatcgag ttattgactc ttgtctttaa tcgatttcgc ttttgggatt    660

tatccctttt tactttgaga aaattagagt gtttcaagca gacttttgtc ttgaatactt    720

cagcatggaa taatagagta ggactttggt tctattttgt tggtttttga accttagtaa    780

tggttaatag gaacggttgg gggcattcgt atttaactgt cagaggtgaa attcttagat    840

ttgttaaaga cgaactactg cgaaagcatt tgccaaggac gtttccatta atcaagaacg    900
```

aaagttaggg gatcgaagac gatcagatac cgtcgtagtc ctaaccataa actatgccga 960
ctagggattg gaggtcgtca tttttccgac tccttcagca ccttgagaga aatcaaagtc 1020
tttgggttct ggggggagta tggtcgcaag gctgaaactt aaaggaattg acggaagggc 1080
accaccaggc gtggagcctg cggcttaatt tgactcaaca cggggaaact caccaggtcc 1140
agacaatgtt aggattgaca gattgatagc tctttcttga ttctttgggt ggtggtgcat 1200
ggccgttctt agttggtgga gtgatttgtc tggttaattc cgttaacgaa cgagacctta 1260
acctgctaac tagtacccgt aaaaaggttc gtccgttacg gtttgcttct tagagggact 1320
ttgcggctct aagccgcaag gaagtttaag gcaataacag gtctgtgatg cccttagatg 1380
tcctgggctg cacgcgcgct acactgatgc attcatcgag tttaatcctg tcccgaaagg 1440
gctgggtaat ctttagtatg catcgtgacg ggattgatt tttgcaattc taaatcatga 1500
acgaggaatg cctagtatgc gcaagtcatc agcttgtgca gattacgtcc ctgccctttg 1560
tacacaccgc ccgtcgctcc taccgatcga gtgatccggt gaattattcg gaccgtggct 1620
tttccgattc gtcggttttg cctagggaag tctcgtgaac cttatcactt aaaggaagga 1680
gaagtcgtaa caaggtttcc gtaggtgaac ctgcagaagg atcaagc 1727

<210> SEQ ID NO 78
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 78
gyygccycgg uaggccaaua cccuaccguc caaagcugau r 41

<210> SEQ ID NO 79
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 79
gyygccycgg taggccaata ccctaccgtc caaagctgat r 41

<210> SEQ ID NO 80
<211> LENGTH: 60
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)
<220> FEATURE:
<221> NAME/KEY: variation
<222> LOCATION: (50)..(50)
<223> OTHER INFORMATION: "n" means a or g or c or t/u, or unknown, or other (WIPO Standard ST.25 (1998), Appendix 2, Table 1)
<220> FEATURE:
<221> NAME/KEY: misc_feature
<222> LOCATION: (50)..(50)
<223> OTHER INFORMATION: n is a, c, g, or t

<400> SEQUENCE: 80
aatttaatac gactcactat agggagaggc aaatgctttc gcagtagttn gtctttaaca 60

<210> SEQ ID NO 81

<211> LENGTH: 33
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: variation
<222> LOCATION: (23)..(23)
<223> OTHER INFORMATION: "n" means a or g or c or t/u, or unknown, or other (WIPO Standard ST.25 (1998), Appendix 2, Table 1)
<220> FEATURE:
<221> NAME/KEY: misc_feature
<222> LOCATION: (23)..(23)
<223> OTHER INFORMATION: n is a, c, g, or t

<400> SEQUENCE: 81
ggcaaatgct ttcgcagtag ttngtcttta aca 33

<210> SEQ ID NO 82
<211> LENGTH: 60
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)
<220> FEATURE:
<221> NAME/KEY: misc_feature
<222> LOCATION: (50)..(50)
<223> OTHER INFORMATION: n is inosine

<400> SEQUENCE: 82
aatttaatac gactcactat agggagaggc aaatgctttc gcagtagttn gtctttaaca 60

<210> SEQ ID NO 83
<211> LENGTH: 33
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (23)..(23)
<223> OTHER INFORMATION: n is inosine

<400> SEQUENCE: 83
ggcaaatgct ttcgcagtag ttngtcttta aca 33

<210> SEQ ID NO 84
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 84
gcggtaattc cagctccaat ag 22

<210> SEQ ID NO 85
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: variation
<222> LOCATION: (11)..(11)
<223> OTHER INFORMATION: "n" means a or g or c or t/u, or unknown, or other (WIPO Standard ST.25 (1998), Appendix 2, Table 1)
<220> FEATURE:

<221> NAME/KEY: misc_feature
<222> LOCATION: (11)..(11)
<223> OTHER INFORMATION: n is a, c, g, or t

<400> SEQUENCE: 85
cttgaatact ncagca 16

<210> SEQ ID NO 86
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (11)..(11)
<223> OTHER INFORMATION: n is inosine

<400> SEQUENCE: 86
cttgaatact ncagca 16

<210> SEQ ID NO 87
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(56)
<223> OTHER INFORMATION: capture tail

<400> SEQUENCE: 87
aaagacuuug auuucucuca aggtttaaaa aaaaaaaaaa aaaaaaaaaa aaaaaa 56

<210> SEQ ID NO 88
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 88
aaagacuuug auuucucuca agg 23

<210> SEQ ID NO 89
<211> LENGTH: 61
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (29)..(61)
<223> OTHER INFORMATION: capture tail

<400> SEQUENCE: 89
caagaaagag cuaucaaucu gucaaucctt taaaaaaaaa aaaaaaaaaa aaaaaaaaaa 60
a 61

<210> SEQ ID NO 90
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 90
caagaaagag cuaucaaucu gucaaucc 28

<210> SEQ ID NO 91
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 91
aguaggacuu ugguuct 17

<210> SEQ ID NO 92
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 92
aguaggacuu ugguuc 16

<210> SEQ ID NO 93
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 93
aguaggacua uugguuc 17

<210> SEQ ID NO 94
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is u or ua

<400> SEQUENCE: 94
aguaggacnu ugguuc 16

<210> SEQ ID NO 95
<211> LENGTH: 95
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: variation
<222> LOCATION: (50)..(50)
<223> OTHER INFORMATION: "n" means a or g or c or t/u, or unknown, or other (WIPO Standard ST.25 (1998), Appendix 2, Table 1)
<220> FEATURE:
<221> NAME/KEY: misc_feature
<222> LOCATION: (50)..(50)
<223> OTHER INFORMATION: n is a, c, g, t or u

<400> SEQUENCE: 95
actttgagaa aaytagagtg tttcaaacag gccatttgcc ttgaatactn cagcatggaa 60
taatgaagta ggactttggt tctattttgt tggtt 95

<210> SEQ ID NO 96
<211> LENGTH: 78
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: variation
<222> LOCATION: (23)..(23)
<223> OTHER INFORMATION: "n" means a or g or c or t/u, or unknown, or other (WIPO Standard ST.25 (1998), Appendix 2, Table 1)
<220> FEATURE:
<221> NAME/KEY: misc_feature
<222> LOCATION: (23)..(23)
<223> OTHER INFORMATION: n is a, c, g, t or u

<400> SEQUENCE: 96
ggcaaatgct ttcgcagtag ttngtcttta acaaatctaa gaatttcacc tctgacagtt 60
aaatacgaat gcccccaa 78

<210> SEQ ID NO 97
<211> LENGTH: 37
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: variation
<222> LOCATION: (23)..(23)
<223> OTHER INFORMATION: "n" means a or g or c or t/u, or unknown, or other (WIPO Standard ST.25 (1998), Appendix 2, Table 1)
<220> FEATURE:
<221> NAME/KEY: misc_feature
<222> LOCATION: (23)..(23)
<223> OTHER INFORMATION: n is a, c, g, t or u

<400> SEQUENCE: 97
ggcaaatgct ttcgcagtag ttngtcttta acaaatc 37

<210> SEQ ID NO 98
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 98
aguaggacua uugguucu 18

<210> SEQ ID NO 99
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is u or ua

<400> SEQUENCE: 99
aguaggacnu ugguucu 17

<210> SEQ ID NO 100
<211> LENGTH: 1281
<212> TYPE: RNA
<213> ORGANISM: Artificial Sequence
<220> FEATURE:
<223> OTHER INFORMATION: B. venatorum In Vitro Transcript

<400> SEQUENCE: 100
gggcgaauug gguaccgggc ccccccucga ggucgacggu aucgauaagc uugauaucga 60
auuccugcag cccgggggau ccaaccuggu ugauccugcc aguagucaua ugcuugucuu 120
aaagauuaag ccaugcaugu cuaaguacaa acuuuuuacg gugaaacugc gaauggcuca 180
uuacaacagu uauaguuucu uugguauucg uuuuccaugg auaaccgugc uaauuguagg 240
gcuaauacaa guucgaggcc uuuuggcggc guuuauuagu ucuauaacca cccuuuuggu 300
uuucggugau ucauaauaaa cucgcgaauc gcaauuuauu gcgauggacc auucaaguuu 360
cugacccauc agcuugacgg uaggguauug gccuaccgag gcagcaacgg guaacgggga 420
auuaggguuc gauuccggag agggagccug agaaacggcu accacaucca aggaaggcag 480
caggcgcgca aauuacccaa uccugacaca gggagguagu gacaagaaau aacaauacag 540
ggcaauuguc uuguaauugg aaugauggug accuaaaccc ucaccagagu aacaauugga 600
gggcaagucu ggugccagca gccgcgguaa uuccagcucc aauagcguau auuaaacuug 660
uugcaguuaa aaagcucgua guugaauuuc ugcguuaucg aguuauugac ucuugucuuu 720
aaucgauuuc gcuuuuggga uuuaucccuu uuuacuuuga gaaaauuaga guguuucaag 780
cagacuuuug ucuugaauac uucagcaugg aauaauagag uaggacuuug guucuauuuu 840
guugguuuuu gaaccuuagu aaugguuaau aggaacgguu gggggcauuc guauuuaacu 900
gucagaggug aaauucuuag auuuguuaaa gacgaacuac ugcgaaagca uuugccaagg 960
acguuuccau uaaucaagaa cgaaaguuag ggaucgaag acgaucagau accgucguag 1020
uccuaaccau aaacuaugcc gacuagggau uggaggucgu cauuuuuccg acuccuucag 1080
caccuugaga gaaaucaaag ucuuuggguu cugggggggag uauggucgca aggcugaaac 1140
uuaaaggaau ugacggaagg gcaccaccag gcguggagcc ugcggcuuaa uuugacucaa 1200
cacggggaaa cucaccaggu ccagacaaug uuaggauuga cagauugaua gcucuuucuu 1260
gauucuuugg guggugcggc c 1281

<210> SEQ ID NO 101
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: variation
<222> LOCATION: (15)..(15)
<223> OTHER INFORMATION: "n" means a or g or c or t/u, or unknown, or other (WIPO Standard ST.25 (1998), Appendix 2, Table 1)
<220> FEATURE:
<221> NAME/KEY: misc_feature
<222> LOCATION: (15)..(15)
<223> OTHER INFORMATION: n is a, c, g, or t

<400> SEQUENCE: 101
ctttcgcagt agttngtctt taac 24